US012625139B2

(12) United States Patent　(10) Patent No.: US 12,625,139 B2

Gruber et al.　(45) Date of Patent:　May 12, 2026

(54) METHODS FOR MODULATION OF ACETYLTRANSFERASE ACTIVITY AND APPLICATIONS THEREOF INCLUDING TREATMENTS

(71) Applicant: The Board of Trustees of the Leland Stanford Junior University, Stanford, CA (US)

(72) Inventors: Joshua James Gruber, Palo Alto, CA (US); Benjamin Geller, Stanford, CA (US); Andrew Lipchik, Stanford, CA (US); Michael P. Snyder, Stanford, CA (US)

(73) Assignee: The Board of Trustees of the Leland Stanford Junior University

( * ) Notice: Subject to any disclaimer, the term of this patent is extended or adjusted under 35 U.S.C. 154(b) by 1231 days.

(21) Appl. No.: 17/594,598

(22) PCT Filed: Apr. 22, 2020

(86) PCT No.: PCT/US2020/029395

§ 371 (c)(1),
(2) Date: Oct. 22, 2021

(87) PCT Pub. No.: WO2020/219598

PCT Pub. Date: Oct. 29, 2020

(65) Prior Publication Data

US 2022/0196660 A1　Jun. 23, 2022

Related U.S. Application Data

(60) Provisional application No. 62/837,086, filed on Apr. 22, 2019.

(51) Int. Cl.
G01N 33/573　(2006.01)

(52) U.S. Cl.
CPC . G01N 33/573 (2013.01); G01N 2333/91057 (2013.01)

(58) Field of Classification Search
CPC .................. A61P 35/00; C12N 9/1029; G01N 2333/91057; G01N 33/573
See application file for complete search history.

(56) References Cited

U.S. PATENT DOCUMENTS

| | | | | |
|---|---|---|---|---|
| 6,974,681 | B1 * | 12/2005 | McGrew | C12N 5/0018 514/8.4 |
| 2007/0065923 | A1 * | 3/2007 | Zheng | G01N 33/54313 435/6.18 |
| 2007/0254830 | A1 * | 11/2007 | Nakamura | A61P 35/00 435/7.1 |
| 2008/0293081 | A1 * | 11/2008 | Milne | G01N 33/582 435/7.72 |
| 2010/0203647 | A1 * | 8/2010 | Hang | C09B 29/12 534/752 |
| 2018/0338899 | A1 | 11/2018 | Miura | |
| 2025/0188083 | A1 | 6/2025 | Gruber et al. | |

FOREIGN PATENT DOCUMENTS

| | | |
|---|---|---|
| WO | 1992005200 A1 | 4/1992 |
| WO | 2020080979 A1 | 4/2020 |
| WO | 2020083856 A1 | 4/2020 |
| WO | 2020219598 A1 | 10/2020 |
| WO | 2020242857 A1 | 12/2020 |
| WO | 2022272313 A1 | 12/2022 |

OTHER PUBLICATIONS

Gruber et al., "An acetyl-click screening platform identifies a small molecule inhibitor of Histone Acetyltransferase 1 (HAT1) with anti-tumor activity," bioRxiv, 2021, 449993, pp. 1-19.*
Yang et al., "Identification of lysine acetyltransferase p300 substrates using 4-pentynoyl-coenzyme A and bioorthogonal proteomics," Bioorg. Med. Chem. Lett., 2011, vol. 21, pp. 4976-4979; Erratum in: Bioorg. Med. Chem. Lett., Nov. 1, 2011;21(21):6613.*
Garner et al., "cat-ELCCA: A Robust Method to Monitor the Fatty Acid Acyltransferase Activity of Ghrelin O-Acyltransferase (GOAT)," Angew. Chem. Int. Ed., 2010, vol. 49, No. 50, pp. 9630-9634.*
Zhang et al., "Human histone acetyltransferase 1 protein preferentially acetylates H4 histone molecules in H3.1-H4 over H3.3-H4," J. Biol. Chem., 2012, vol. 287, No. 9, pp. 6573-6581.*
International Preliminary Report on Patentability for International Application No. PCT/US2020/029395 issued Sep. 28, 2021, Mailed on Nov. 4, 2021, 9 pgs.
International Preliminary Report on Patentability for International Application No. PCT/US2022/073191, Report issued Dec. 14, 2023, Mailed on Jan. 4, 2024, 8 pgs.
International Search Report and Written Opinion for International Application No. PCT/US2020/029395, Search completed Jul. 27, 2020, Mailed Aug. 17, 2020, 16 pgs.
International Search Report and Written Opinion for International Application No. PCT/US2022/073191, Search completed Oct. 5, 2022, Mailed Oct. 28, 2022, 13 pgs.
Baell et al., "Histone acetyltransferase inhibitors: where art thou?", Future Medicinal Chemistry, vol. 8, No. 13, Sep. 2016, published online Aug. 24, 2016, pp. 1525-1528, doi: 10.4155/fmc-2016-0151.
Baell et al., "Inhibitors of histone acetyltransferases KAT6A/B induce senescence and arrest tumour growth", Nature, vol. 560, No. 7717, Aug. 2018, pp. 253-257, doi: 10.1038/s41586-018-0387-5.
Barile et al., "Riboflavin transport and metabolism in humans", Journal of Inherited Metabolic Disease, vol. 39, No. 4, Jul. 2016, pp. 545-557, published online Jun. 6, 2016, doi: 10.1007/s10545-016-9950-0.

(Continued)

*Primary Examiner* — Galina M. Yakovleva
(74) *Attorney, Agent, or Firm* — KPPB LLP

(57) ABSTRACT

Methods to identify modulators of histone acetyltransferases are described. Modulators of histone acetyltransferases can be used to treat individuals. In some instances, modulators of histone acetyltransferases are utilized to treat individuals having a neoplasm.

17 Claims, 36 Drawing Sheets

Specification includes a Sequence Listing.

(56) References Cited

OTHER PUBLICATIONS

Bulusu et al., "Acetate Recapturing by Nuclear Acetyl-CoA Synthetase 2 Prevents Loss of Histone Acetylation during Oxygen and Serum Limitation", Cell Reports, vol. 18, No. 3, Jan. 17, 2017, pp. 647-658, doi: 10.1016/j.celrep.2016.12.055.

Cai et al., "Acetyl-CoA Induces Cell Growth and Proliferation by Promoting the Acetylation of Histones at Growth Genes", Molecular Cell, vol. 42, No. 4, May 20, 2011, pp. 426-437, doi: 10.1016/j.molcel.2011.05.004.

Campos et al., "The program for processing newly synthesized histones H3.1 and H4", Nature Structural & Molecular Biology, vol. 17, No. 11, Nov. 2010, pp. 1343-1351, doi: 10.1038/nsmb.1911.

Comerford et al., "Acetate Dependence of Tumors", Cell, vol. 159, No. 7, Dec. 18, 2014, pp. 1591-1602, doi: 10.1016/j.cell.2014.11.020.

Dahlin et al., "Assay interference and off-target liabilities of reported histone acetyltransferase inhibitors", Nature Communications, vol. 8, No. 1527, Nov. 15, 2017, 14 pgs., doi: 10.1038/s41467-017-01657-3.

Eriksson et al., "Global Regulation by the Yeast Spt10 Protein Is Mediated through Chromatin Structure and the Histone Upstream Activating Sequence Elements", Molecular and Cell Biology, vol. 25. No. 20, Oct. 2005, pp. 9127-9137, doi: 10.1128/MCB.25.20.9127-9137.2005.

Evertts et al., "Quantitative Dynamics of the Link between Cellular Metabolism and Histone Acetylation", Journal of Biological Chemistry, vol. 288, No. 17, Apr. 26, 2013, pp. 12142-12151, doi: 10.1074/jbc.M112.428318.

Falk et al., "An Efficient High-Throughput Screening Method for MYST Family Acetyltransferases, a New Class of Epigenetic Drug Targets", Journal of Biomolecular Screening, vol. 16, No. 10, Dec. 2011, published online Nov. 14, 2011, pp. 1196-1205, doi: 10.1177/1087057111421631.

Fan et al., "Overexpressed histone acetyltransferase 1 regulates cancer immunity by increasing programmed death-ligand 1 expression in pancreatic cancer", Journal of Experimental & Clinical Cancer Research, vol. 38, No. 47, Feb. 2019, pp. 1-12, doi: 10.1186/s13046-019-1044-z.

Fujimura et al., "Functional Characteristics of the Human Ortholog of Riboflavin Transporter 2 and Riboflavin-Responsive Expression of Its Rat Ortholog in the Small Intestine Indicate Its Involvement in Riboflavin Absorption", The Journal of Nutrition, vol. 140, No. 10, Oct. 2010, first published Aug. 19, 2010, pp. 1722-1727, doi: 10.3945/jn.110.128330.

Gaddameedi et al., "Acetyl-Click Screening Platform Identifies Small-Molecule Inhibitors of Histone Acetyltransferase 1 (HAT1)", Journal of Medicinal Chemistry, vol. 66, No. 8, Apr. 7, 2023, pp. 5774-5801, doi: 10.1021/acs.jmedchem.3c00039.

Garcia et al., "Identification of multiple roles for histone acetyltransferase 1 in replication-coupled chromatin assembly", Nucleic Acids Research, vol. 45, No. 16, Sep. 19, 2017, first published Jun. 28, 2017, pp. 9319-9335, doi: 10.1093/nar/gkx545.

Gruber et al., "HAT1 Coordinates Histone Production and Acetylation via H4 Promoter Binding", Molecular Cell, vol. 75, No. 4, Aug. 22, 2019, published online Jul. 2, 2019, pp. 711-724.e1-e5, doi: 10.1016/j.molcel.2019.05.034.

Hale, "Celgene inks $1B deal for a preclinical epigenetic blood cancer drug from Canada", Fierce Biotech, Jan. 29, 2019, 4 pgs.

Hammond et al., "Histone chaperone networks shaping chromatin function", Nature Reviews Molecular Cell Biology, vol. 18, No. 3, Mar. 2017, published online Jan. 5, 2017, pp. 141-158, doi: 10.1038/nrm.2016.159.

Kamphorst et al., "Quantitative analysis of acetyl-CoA production in hypoxic cancer cells reveals substantial contribution from acetate", Cancer & Metabolism, vol. 2, No. 23, Dec. 11, 2014, pp. 1-8, doi: 10.1186/2049-3002-2-23.

Keck et al., "Histone chaperones link histone nuclear import and chromatin assembly", Biochimica et Biophysica Acta (BBA)—

Gene Regulatory Mechanisms, vol. 1819, No. 3-4, Mar.-Apr. 2012, pp. 277-289, doi: 10.1016/j.bbagrm.2011.09.007.

Kharchenko et al., "Design and analysis of ChIP-seq experiments for DNA-binding proteins", Nature Biotechnology, vol. 26, No. 12, Dec. 2008, pp. 1351-1359, doi: 10.1038/nbt.1508.

Kurat et al, "Cell cycle-regulated oscillator coordinates core histone gene transcription through histone acetylation", PNAS, vol. 111, No. 39, Sep. 30, 2014, first published Sep. 16, 2014, p. 14124-14129, doi: 10.1073/pnas.1414024111.

Kurat et al., "Regulation of histone gene transcription in yeast", Cellular and Molecular Life Sciences, vol. 71, No. 4, Feb. 2014, published online Aug. 23, 2013, pp. 599-613, doi: 10.1007/s00018-013-1443-9.

Lasko et al., "Discovery of a selective catalytic p300/CBP inhibitor that targets lineage-specific tumours", Nature, vol. 550, No. 7674, Oct. 5, 2017, published online Sep. 27, 2017, pp. 128-132, doi: 10.1038/nature24028.

Lau et al., "HATs off: Selective Synthetic Inhibitors of the Histone Acetyltransferases p300 and PCAF", Molecular Cell, vol. 5, No. 3, Mar. 2000, pp. 589-595, doi: 10.1016/S1097-2765(00)80452-9.

Lipchik et al., "KINATEST-ID: A Pipeline To Develop Phosphorylation-Dependent Terbium Sensitizing Kinase Assays", Journal of the American Chemical Society, vol. 137, No. 7, Feb. 17, 2015, pp. 2484-2494, doi: 10.1021/ja507164a.

Ma et al., "Deposition-related sites K5/K12 in histone H4 are not required for nucleosome deposition in yeast", Proceedings of the National Academy of Sciences of the United States of America, vol. 95, No. 12, Jun. 9, 1998, pp. 6693-6698, doi: 10.1073/pnas.95.12.6693.

Marin et al., "AMPK promotes mitochondrial biogenesis and function by phosphorylating the epigenetic factors DNMT1, RBBP7, and HAT1", Science Signaling, vol. 10, No. 464, Jan. 31, 2017, pp. 1-21, doi: 0.1126/scisignal.aaf7478.

Marzluff et al., "The Human and Mouse Replication-Dependent Histone Genes", Genomics, vol. 80, No. 5, Nov. 2002, pp. 487-498, doi: 10.1006/geno.2002.6850.

Medina et al., "The Histone Gene Cell Cycle Regulator HiNF-P Is a Unique Zinc Finger Transcription Factor with a Novel Conserved Auxiliary DNA-Binding Motif", Biochemistry, vol. 47, No. 44, Nov. 4, 2008, published online Oct. 14, 2008, pp. 11415-11423, doi: 10.1021/bi800961d.

Megee et al., "Genetic Analysis of Histone H4: Essential Role of Lysines Subject to Reversible Acetylation", Science, vol. 247, No. 4944, Feb. 16, 1990, pp. 841-845, doi: 10.1126/science.2106160.

Mitra et al., "Identification of HiNF-P a Key Activator of Cell Cycle-Controlled Histone H4 Genes at the Onset of S Phase", Molecular and Cellular Biology, vol. 23, No. 22, Nov. 1, 2003, pp. 8110-8123, doi: 10.1128/mcb.23.22.8110-8123.2003.

Murzina et al., "Structural Basis for the Recognition of Histone H4 by the Histone-Chaperone RbAp46", Structure, vol. 16, No. 7, Jul. 9, 2008, pp. 1077-1085, doi: 10.1016/j.str.2008.05.006.

Nagarajan et al., "Histone Acetyl Transferase 1 Is Essential for Mammalian Development, Genome Stability, and the Processing of Newly Synthesized Histones H3 and H4", PLOS Genetics, vol. 9, No. 6, e1003518, Jun. 1, 2013, 16 pgs., doi: 10.1371/journal.pgen.1003518.

Ngo et al., "Bisubstrate inhibitors to target histone acetyltransferase 1", Chemical Biology & Drug Design, vol. 93, No. 5, May 2019, first published Jan. 14, 2019, pp. 865-873, doi: 10.1111/cbdd.13476.

Parthun, "Histone acetyltransferase 1: More than just an enzyme?", Biochimica et Biophysica Acta (BBA)—Gene Regulatory Mechanisms, vol. 1819, No. 3-4, Mar.-Apr. 2012, published online Jul. 18, 2011, pp. 256-263, doi: 10.1016/j.bbagrm.2011.07.006.

Parthun et al., "The Major Cytoplasmic Histone Acetyltransferase in Yeast: Links to Chromatin Replication and Histone Metabolism", Cell, vol. 87, No. 1, Oct. 4, 1996, pp. 85-94, doi: 10.1016/s0092-8674(00)81325-2.

Qin et al., "Histone H3 and the Histone Acetyltransferase Hat1p Contribute to DNA Double-Strand Break Repair", Molecular and Cellular Biology, vol. 22, No. 23, Dec. 2002, pp. 8353-8365, doi: 10.1128/MCB.22.23.8353-8365.2002.

(56)        References Cited

OTHER PUBLICATIONS

Schug et al., "Acetyl-CoA Synthetase 2 Promotes Acetate Utilization and Maintains Cancer Cell Growth under Metabolic Stress", Cancer Cell, vol. 27, Jan. 12, 2015, pp. 57-71, doi: 10.1016/j.ccell.2014.12.002.

Shibahara et al., "The N-terminal domains of histones H3 and H4 are not necessary for chromatin assembly factor-1-mediated nucleosome assembly onto replicated DNA in vitro", PNAS, vol. 97, No. 14, Jul. 5, 2000, pp. 7766-7771, doi: 10.1073/pnas.97.14.7766.

Tutino et al., "The Expression of Riboflavin Transporters in Human Colorectal Cancer", Anticancer Research, vol. 38, No. 5, May 2018, pp. 2659-2667, doi: 10.21873/anticanres.12508.

Wellen et al., "ATP-Citrate Lyase Links Cellular Metabolism to Histone Acetylation", Science, vol. 324, No. 5930, May 22, 2009, pp. 1076-1080, doi: 10.1126/science.1164097.

Wu et al., "Structural basis for substrate specificity and catalysis of human histone acetyltransferase 1", PNAS, vol. 109, No. 23, Jun. 5, 2012, pp. 8925-8930, doi: 10.1073/pnas.1114117109.

Xia et al., "Folate-targeted therapies for cancer", Journal of Medicinal Chemistry, vol. 53, No. 19, Jul. 28, 2010, pp. 6811-6824, doi: 10.1021/jm100509v.

Xia et al., "MicroRNA-377 exerts a potent suppressive role in osteosarcoma through the involvement of the histone acetyltransferase 1-mediated Wnt axis", Journal of Cellular Physiology, vol. 234, No. 12, published online May 31, 2019, pp. 22787-22798, doi: 10.1002/jcp.28843.

Xu et al., "Acetylation in Histone H3 Globular Domain Regulates Gene Expression in Yeast", Cell, vol. 121, No. 3, May 6, 2005, pp. 375-385, doi: 10.1016/j.cell.2005.03.011.

Xue et al., "RNAi screening identifies HAT1 as a potential drug target in esophageal squamous cell carcinoma", International Journal of Clinical and Experimental Pathology, vol. 7, No. 7, Jun. 15, 2014, pp. 3898-3907.

Yang et al., "Histone acetyltransferase 1 is a succinyltransferase for histones and non-histones and promotes tumorigenesis", EMBO Reports, vol. 22, No. 2, e50967, Feb. 3, 2021, published online Dec. 29, 2020, 18 pgs., doi: 10.15252/embr.202050967.

Yang et al., "Histone Acetyltransferase 1 Promotes Homologous Recombination in DNA Repair by Facilitating Histone Turnover", Journal of Biological Chemistry, vol. 288, No. 25, Jun. 21, 2013, pp. 18271-18282, doi: 10.1074/jbc.M113.473199.

Zaidi et al., "ATP-Citrate Lyase: A Key Player in Cancer Metabolism", Cancer Research, vol. 72, No. 15, Aug. 2012, pp. 3709-3714, doi: 10.1158/0008-5472.CAN-11-4112.

Zhang et al., "Essential and redundant functions of histone acetylation revealed by mutation of target lysines and loss of the Gcn5p acetyltransferase", The EMBO Journal, vol. 17, 1998, pp. 3155-3167, doi: 10.1093/emboj/17.11.3155.

Zhao et al., "ATP-Citrate Lyase Controls a Glucose-to-Acetate Metabolic Switch", Cell Reports, vol. 17, No. 4, Oct. 18, 2016, pp. 1037-1052, doi: 10.1016/j.celrep.2016.09.069.

Zhao et al., "NPAT links cyclin E-Cdk2 to the regulation of replication-dependent histone gene transcription", Genes & Development, vol. 14, No. 18, Sep. 15, 2000, pp. 2283-2297, doi: 10.1101/gad.827700.

Zheng et al., "S Phase Activation of the Histone H2B Promoter by OCA-S, a Coactivator Complex that Contains GAPDH as a Key Component", Cell, vol. 114. No. 2, Jul. 25, 2003, pp. 255-266, doi: 10.1016/s0092-8674(03)00552-x.

* cited by examiner

Fig. 2

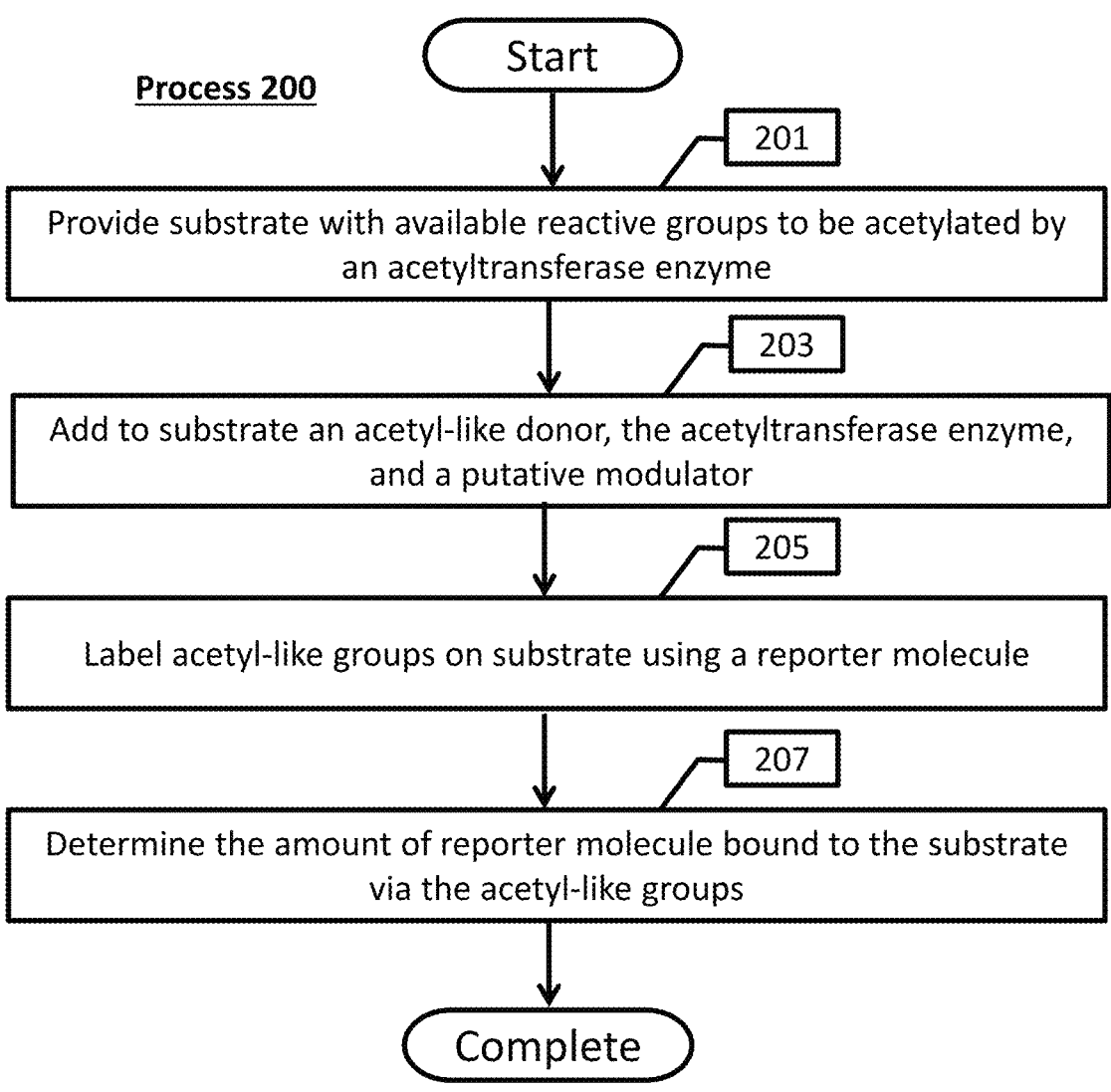

Process 200

Start

201

Provide substrate with available reactive groups to be acetylated by an acetyltransferase enzyme

203

Add to substrate an acetyl-like donor, the acetyltransferase enzyme, and a putative modulator

205

Label acetyl-like groups on substrate using a reporter molecule

207

Determine the amount of reporter molecule bound to the substrate via the acetyl-like groups Complete

Fig. 3A

CAS: 6988-61-0
NSC 405936

CAS: 7249-98-1
NSC 56094

Fig. 3B

CAS: 11052-70-3
NSC 86005

NSC 309109

Fig. 3C

CAS: 34610-60-1
NSC 143491

CAS: 23666-50-4
NSC 136044

CAS: 57576-44-0
NSC 208734

CAS: 35906-51-5
NSC 243023

Fig. 3D

CAS: 63710-10-1
NSC 265211

NSC 265450

CAS: 70878-51-2
NSC 268242

CAS: 668-17-7
NSC 267229

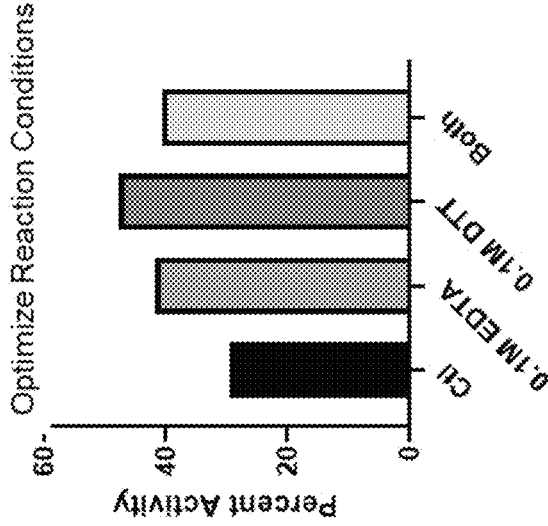
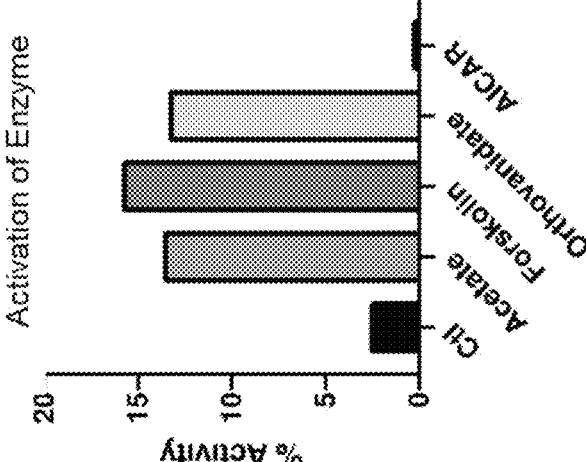
Fig. 5
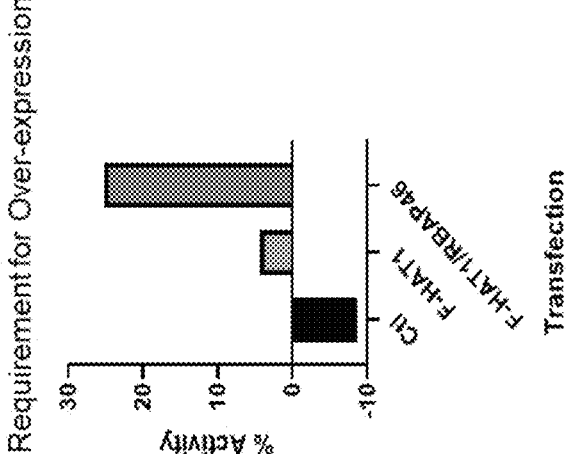

Fig. 7A
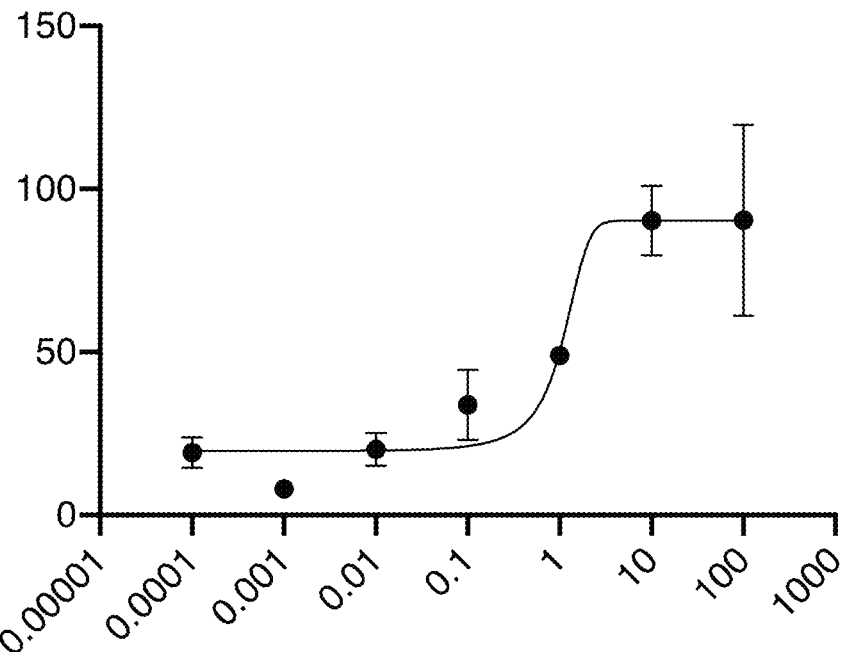
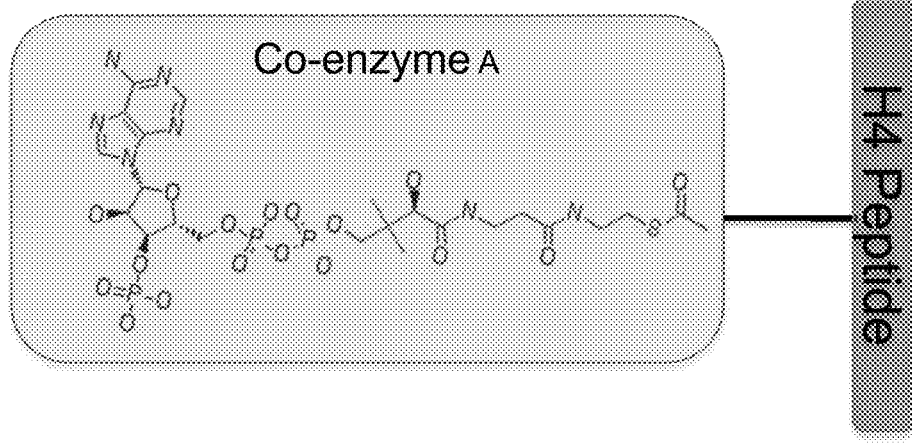

Fig. 7B
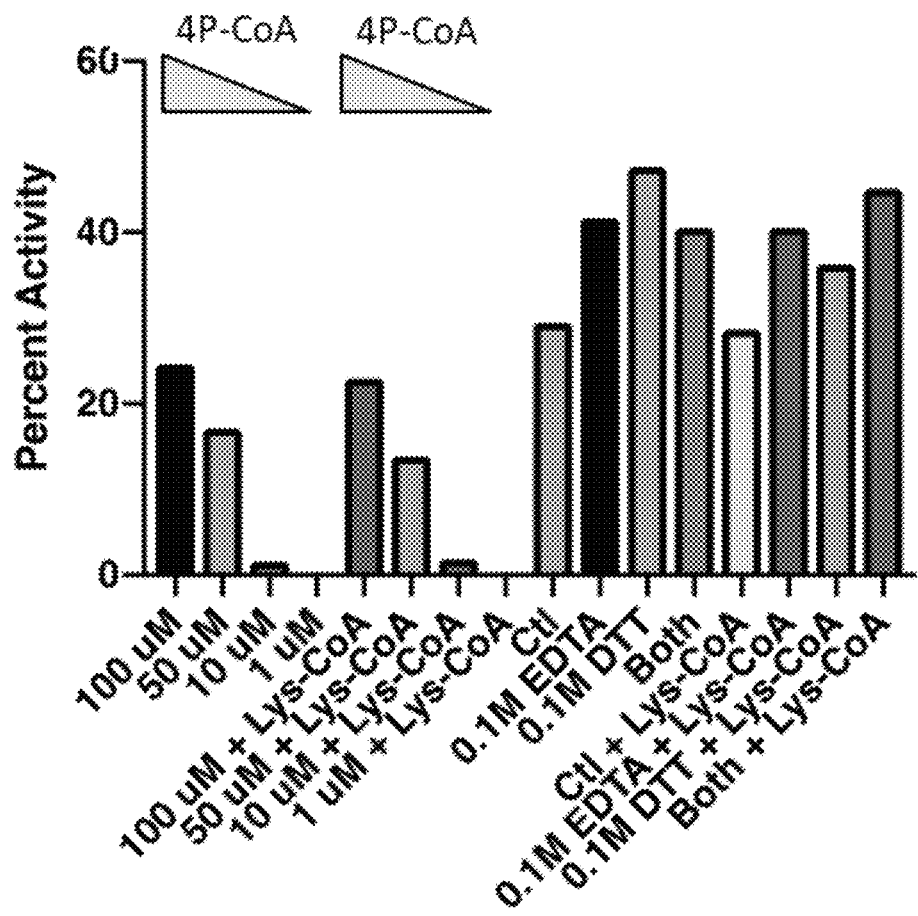
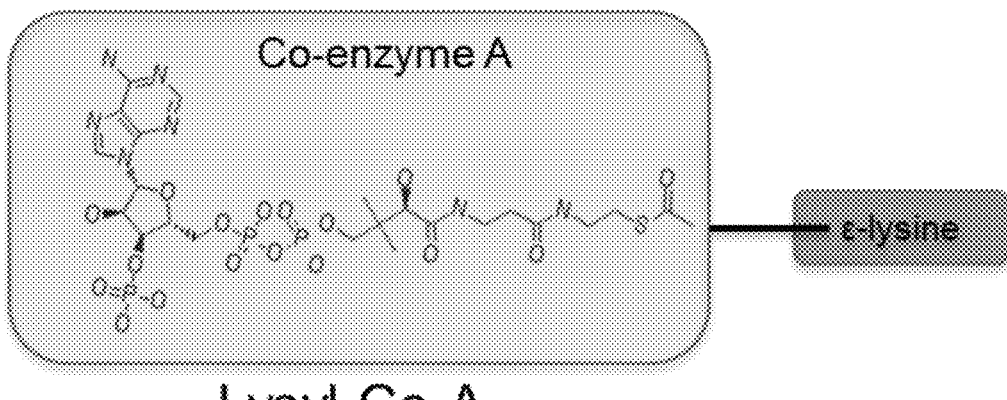
Lysyl-Co-A

Enriched Gene Sets
-EGF/+EGF (FDR < 0.01)

Fig. 17

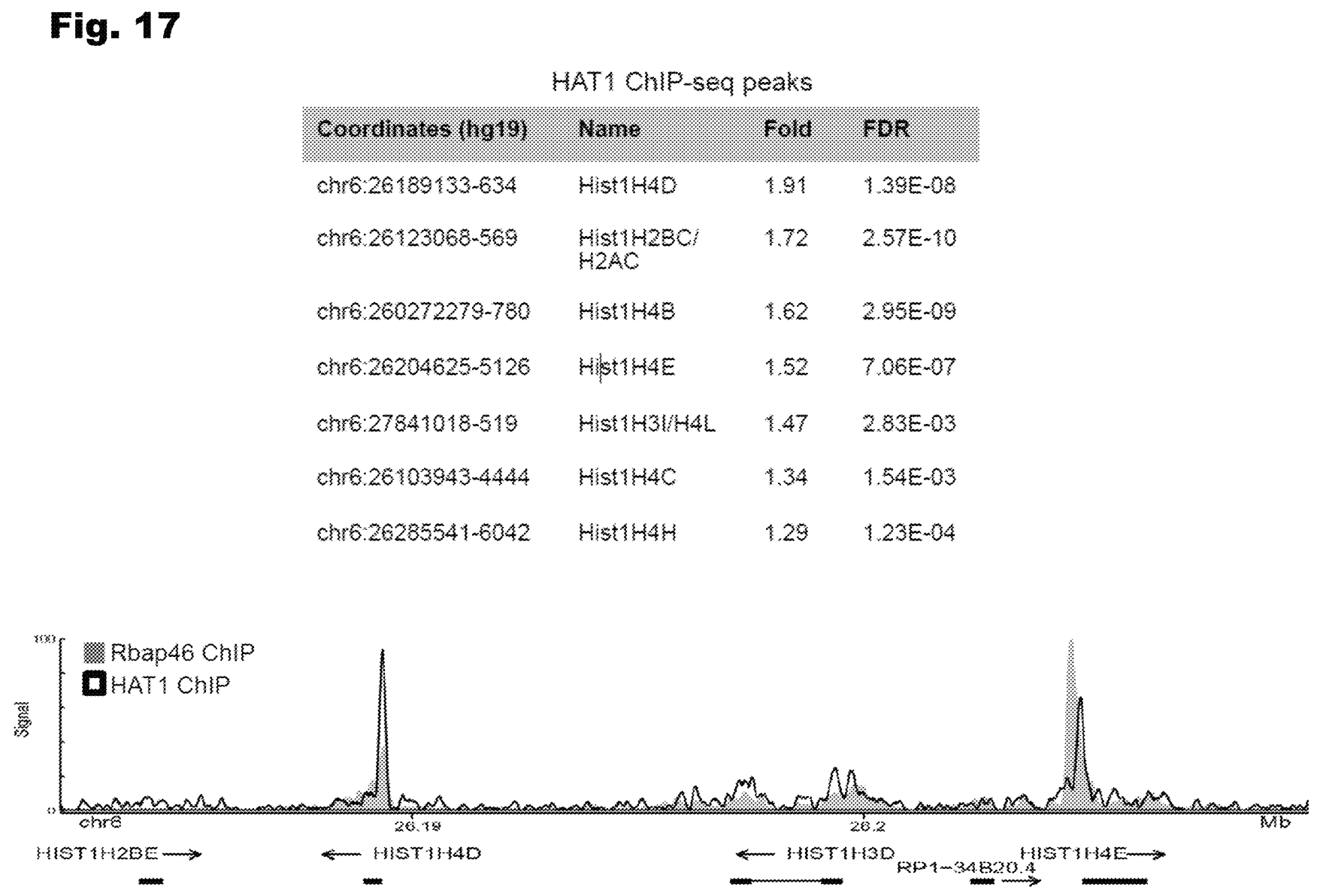

HAT1 ChIP-seq peaks

| Coordinates (hg19) | Name | Fold | FDR |
|---|---|---|---|
| chr6:26189133-634 | Hist1H4D | 1.91 | 1.39E-08 |
| chr6:26123068-569 | Hist1H2BC/H2AC | 1.72 | 2.57E-10 |
| chr6:260272279-780 | Hist1H4B | 1.62 | 2.95E-09 |
| chr6:26204625-5126 | Hist1H4E | 1.52 | 7.06E-07 |
| chr6:278410118-519 | Hist1H3I/H4L | 1.47 | 2.83E-03 |
| chr6:261103943-4444 | Hist1H4C | 1.34 | 1.54E-03 |
| chr6:26285541-6042 | Hist1H4H | 1.29 | 1.23E-04 |

(SEQ. ID No. 20)

|        | siCont | siHAT1 |
|--------|--------|--------|
| G0/G1  | 56.6%  | 61.8%  |
| S      | 22.6%  | 21.3%  |
| G2/M   | 18.6%  | 15.1%  |

Time after release from double thymidine block (h)

Fig. 30
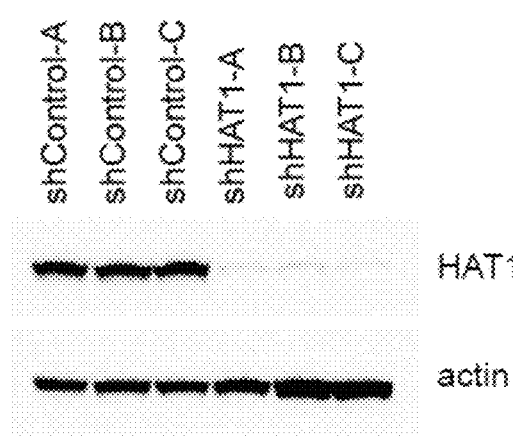
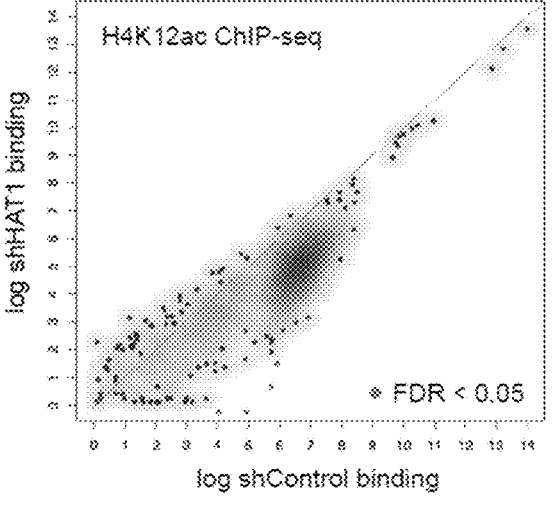
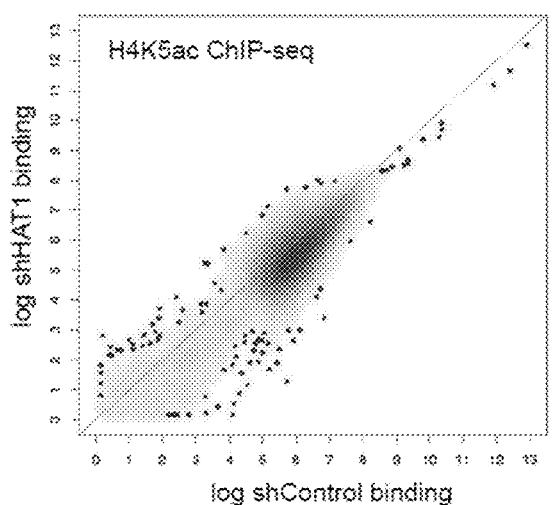
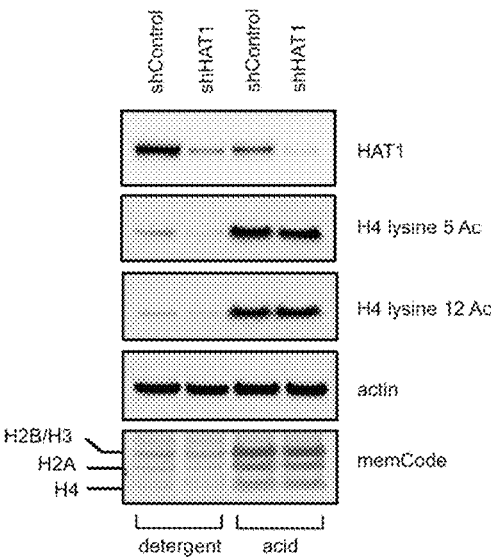

Fig. 31

Fig. 32
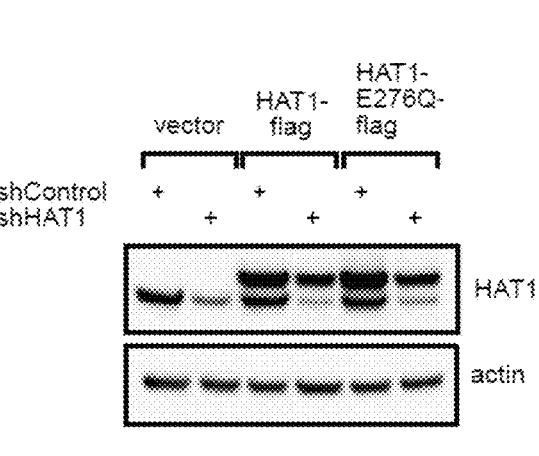
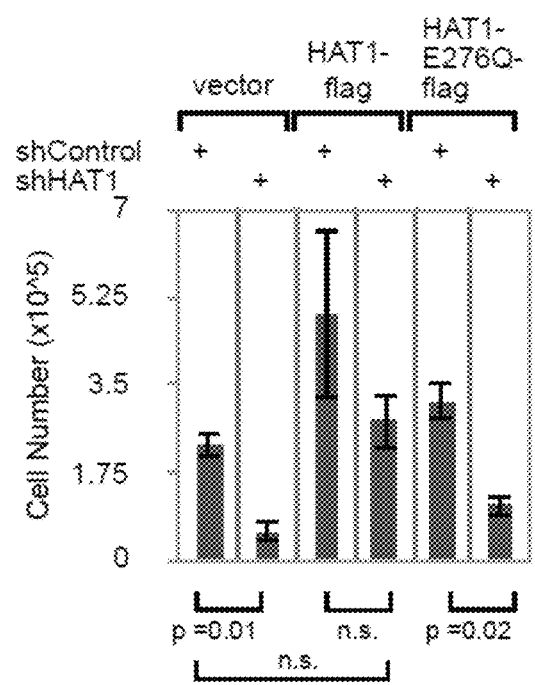
Fig. 33
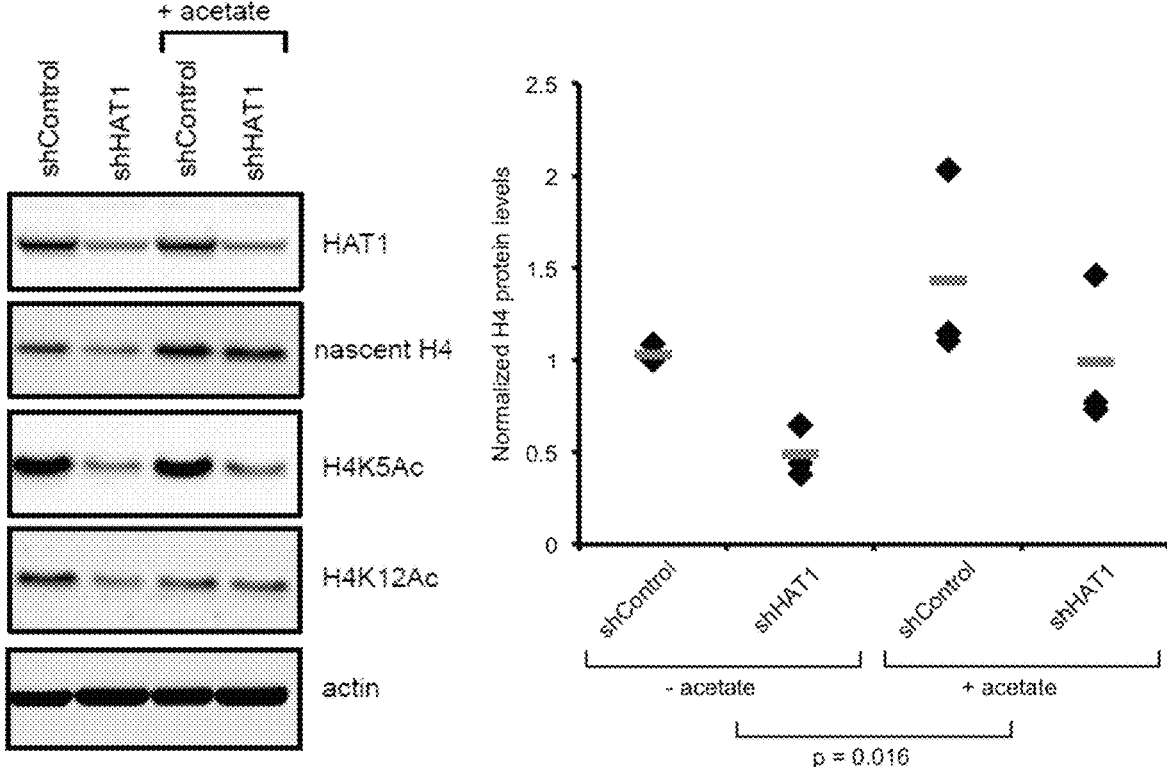

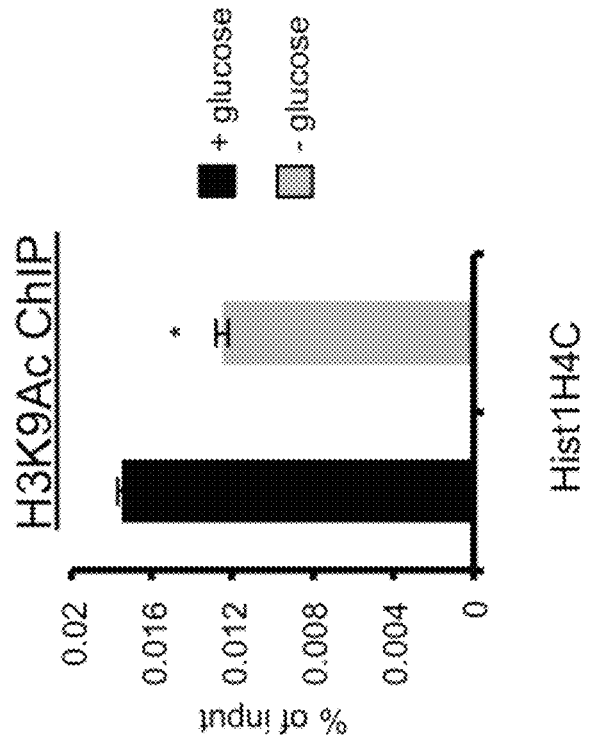
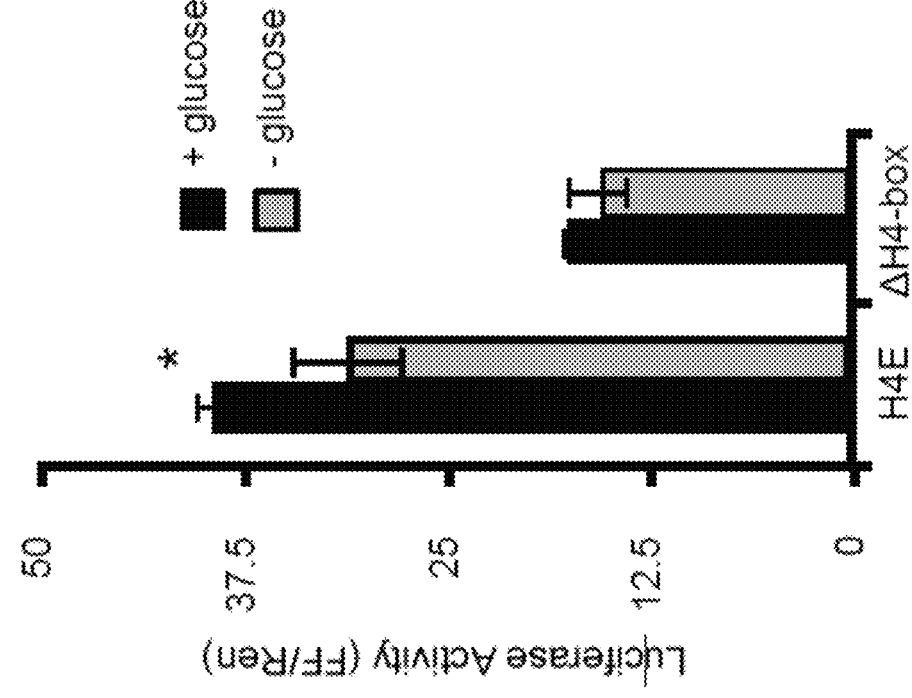
Fig. 44

SEQUENCE LISTING

<160> NUMBER OF SEQ ID NOS: 20

<210> SEQ ID NO 1
<211> LENGTH: 23
<212> TYPE: PRT
<213> ORGANISM: Homo sapiens

<400> SEQUENCE: 1

Ser Gly Arg Gly Lys Gly Gly Lys Gly Leu Gly Lys Gly Gly Ala Lys

-continued

```
1               5               10              15

Arg His Arg Lys Val Leu Arg
            20

<210> SEQ ID NO 2
<211> LENGTH: 20
<212> TYPE: PRT
<213> ORGANISM: Homo sapiens

<400> SEQUENCE: 2

Ser Gly Arg Gly Lys Gly Gly Lys Gly Leu Gly Lys Gly Gly Ala Lys
1               5               10              15

Arg His Arg Lys
            20

<210> SEQ ID NO 3
<211> LENGTH: 29
<212> TYPE: DNA
<213> ORGANISM: Homo sapiens

<400> SEQUENCE: 3
gatggcacta ctttctagta tttgagaag                                      29

<210> SEQ ID NO 4
<211> LENGTH: 29
<212> TYPE: DNA
<213> ORGANISM: Homo sapiens

<400> SEQUENCE: 4
aaggatggag ctacgctctt tgcgaccgt                                      29

<210> SEQ ID NO 5
<211> LENGTH: 29
<212> TYPE: DNA
<213> ORGANISM: Homo sapiens

<400> SEQUENCE: 5
tcctacagtt cttgatatta cagcggaag                                      29

<210> SEQ ID NO 6
<211> LENGTH: 41
<212> TYPE: DNA
<213> ORGANISM: Homo sapiens

<400> SEQUENCE: 6
cagttcttga tattacagcg caagatccat ccaaaagcta t                        41

<210> SEQ ID NO 7
<211> LENGTH: 41
<212> TYPE: DNA
<213> ORGANISM: Homo sapiens

<400> SEQUENCE: 7
atagcttttg gatggatctt gcgctgtaat atcaagaact g                        41

<210> SEQ ID NO 8
<211> LENGTH: 69
<212> TYPE: DNA
<213> ORGANISM: Homo sapiens

<400> SEQUENCE: 8
ggtcgcaaag agcgtagctc cgtctttgtt gtatttctca aatactagaa agtagtgcca    60
```

-continued

```
tctttcatc                                                             69

<210> SEQ ID NO 9
<211> LENGTH: 69
<212> TYPE: DNA
<213> ORGANISM: Homo sapiens

<400> SEQUENCE: 9
gatgaaagat ggcactactt tctagtattt gagaaataca acaaagacgg agctacgctc   60
tttgcgacc                                                             69

<210> SEQ ID NO 10
<211> LENGTH: 21
<212> TYPE: DNA
<213> ORGANISM: Homo sapiens

<400> SEQUENCE: 10
gguacuacgu gucuaagaat t                                               21

<210> SEQ ID NO 11
<211> LENGTH: 21
<212> TYPE: DNA
<213> ORGANISM: Homo sapiens

<400> SEQUENCE: 11
ggugguaucu guuuccguat t                                               21

<210> SEQ ID NO 12
<211> LENGTH: 21
<212> TYPE: DNA
<213> ORGANISM: Homo sapiens

<400> SEQUENCE: 12
ccauuugaga aaccuaauat t                                               21

<210> SEQ ID NO 13
<211> LENGTH: 21
<212> TYPE: DNA
<213> ORGANISM: Homo sapiens

<400> SEQUENCE: 13
aauggaaccu guaaguguat t                                               21

<210> SEQ ID NO 14
<211> LENGTH: 21
<212> TYPE: DNA
<213> ORGANISM: Homo sapiens

<400> SEQUENCE: 14
gcaacacgcu agaaggguut t                                               21

<210> SEQ ID NO 15
<211> LENGTH: 21
<212> TYPE: DNA
<213> ORGANISM: Mus musculus

<400> SEQUENCE: 15
gaagctacag actggatatt a                                               21

<210> SEQ ID NO 16
<211> LENGTH: 21
<212> TYPE: DNA
<213> ORGANISM: Mus musculus
```

```
<400> SEQUENCE: 16
gaagatcttg ctgtactata t                                                    21

<210> SEQ ID NO 17
<211> LENGTH: 22
<212> TYPE: DNA
<213> ORGANISM: Homo sapiens

<400> SEQUENCE: 17
caacacacca acgaaaatag cc                                                   22

<210> SEQ ID NO 18
<211> LENGTH: 22
<212> TYPE: DNA
<213> ORGANISM: Homo sapiens

<400> SEQUENCE: 18
cgctcgttgt agatgtcgtt ag                                                   22

<210> SEQ ID NO 19
<211> LENGTH: 34
<212> TYPE: DNA
<213> ORGANISM: Homo sapiens

<400> SEQUENCE: 19
ctgtctctta tacacatctc cgagcccacg agac                                      34

<210> SEQ ID NO 20
<211> LENGTH: 33
<212> TYPE: DNA
<213> ORGANISM: Homo sapiens

<400> SEQUENCE: 20
ctgtctctta tacacatctg acgctgccga cga                                       33
```

METHODS FOR MODULATION OF ACETYLTRANSFERASE ACTIVITY AND APPLICATIONS THEREOF INCLUDING TREATMENTS

CROSS-REFERENCE TO RELATED APPLICATIONS

This application is a national stage of PCT Patent Application No. PCT/US2020/029395, entitled "Methods for Modulation of Acetyltransferase Activity and Applications Thereof Including Treatments" to Joshua James Gruber et al., filed on Apr. 22, 2020, which claims priority to U.S. Provisional Patent Application No. 62/837,086, entitled "Methods for Modulation of Histone Acetyltransferase Activity and Applications Thereof Including Treatments" to Joshua James Gruber et al., filed on Apr. 22, 2019, the disclosures of which are incorporated herein by reference in their entireties.

REFERENCE TO A SEQUENCE LISTING SUBMITTED ELECTRONICALLY VIA EFS-WEB

The instant application contains a Sequence Listing which has been filed electronically in ASCII format and is hereby incorporated by reference in its entirety. Said ASCII copy, created on Apr. 22, 2020, is named "06132PCT_ST25.txt" and is 3612 bytes in size.

FIELD OF THE INVENTION

The invention is generally directed to processes to modulate acetyltransferases and applications thereof, and more specifically to methods for identifying modulators of acetyltransferase activity including activity of histone acetyltransferase 1 (HAT1) and treatments utilizing histone acetyltransferase modulators.

BACKGROUND

Acetyltransferases are enzymes that transfer an acetyl functional group from a donor molecule onto a biomolecule. Acetyltransferase enzymes include (but are not limited to) histone acetyltransferases, choline acetyltransferase, chloramphenicol acetyltransferase, serotonin N-acetyltransferase, and N-terminal acetyltransferases.

A common acetylation reaction performed by acetyltransferases is the transfer of the acetyl group from acetyl coenzyme A onto its substrate. For example, choline acetyltransferase (ChAT) transfers an acetyl group from the donor acetyl CoA onto a choline molecule yielding acetylcholine, a functional molecule for neural signaling.

Another common example is the class of histone acetyltransferases (HATs), which transfer an acetyl group from acetyl CoA onto histones, which are a class of proteins that help facilitate DNA chromatin formation and regulation of gene expression. Four histones (H2A, H2B, H3 and H4) are combined to form a histone core. Each of these four histone proteins can be acetylated.

Acetylation of histones occurs on particular lysines of the protein. This reaction is portrayed in FIG. 1. The acetyl group of acetyl-CoA is transferred onto the amino group of lysine. Histone deacetylases (HDACs) remove acetyl groups from histones and back onto acetyl CoA. HAT and HDAC enzymatic activity results in particular acetylation patterns, conferring gene expression regulation. Generally, histone cores with high acetylation yields higher levels of gene expression and vice versa. Histone acetyltransferase 1 (HAT1) is an enzyme that acetylates the histone H4, and particularly on lysines 5 and 12. However, the role of di-acetylation of H4 remains enigmatic.

SUMMARY OF THE INVENTION

Many embodiments are directed to methods of assaying for acetyltransferase modulators and treatments of neoplasms based upon discovery of modulators of acetyltransferase activity. In many of these embodiments, an assay is performed with putative modulators to determine their ability to modulate acetyltransferase activity. Various embodiments are also directed towards utilizing histone acetyltransferase 1 (HAT1) antagonists for cancer treatment.

In an embodiment to identify modulators of acetyltransferase activity, a substrate is provided. The substrate has available functional groups for acetylation. An acetyltransferase, a donor molecule having an acetyl-like group with an alkyne handle, and a modulator is added to the substrate such that the acetyltransferase is capable of transferring the acetyl-like group with the alkyne handle of the donor molecule onto the available functional groups of the substrate. The modulator is a compound being assessed for its ability to modulate the transfer of the acetyl-like group onto the available functional groups of the substrate. Biotin-azide is added to the substrate such that the azide group is capable of conjugating to the acetyl-like groups with alkyne handle that have been transferred onto the substrate such that the biotin from the biotin-azide is extended from the acetyl-like groups. A reporter molecule conjugated with streptavidin is added to the substrate such that the reporter molecule binds to the biotin that is extended from the acetyl-like groups. The reporter molecule enables a measurement of the transfer of the acetyl-like group with the alkyne handle of the donor molecule onto the available functional groups of the substrate.

In another embodiment, the acetyltransferase is a histone acetyltransferase, a choline acetyltransferase, a chloramphenicol acetyltransferase, a serotonin N-acetyltransferase, or a N-terminal acetyltransferase.

In yet another embodiment, the acetyltransferase is a recombinant histone acetyltransferase 1 (HAT1).

In a further embodiment, the substrate is a peptide, a nucleic acid, a metabolite, a hormone, or a neurotransmitter.

In still yet another embodiment, the substrate is an n-terminal peptide of histone H4.

In yet a further embodiment, the n-terminal peptide of histone H4 has a sequence inclusive of SEQ ID No. 1.

In an even further embodiment, the n-terminal peptide of histone H4 is provided at 15 $\mu$M.

In yet an even further embodiment, the donor molecule is 4-pentynoyl Co-A.

In still yet an even further embodiment, the reporter molecule is a fluorophore, a radioisotope, an enzyme, or an antigen binding molecule.

In still yet an even further embodiment, the reporter molecule is horse radish peroxidase (HRP) and a HRP substrate is utilized to visualize HRP activity.

In still yet an even further embodiment, the HRP substrate is 10-Acetyl-3,7-dihydroxyphenoxazine.

In still yet an even further embodiment, the acetyltransferase is a recombinant histone acetyltransferase 1 (HAT1), the substrate is an n-terminal peptide of histone H4, the donor molecule is 4-pentynoyl Co-A, the reporter molecule is horse radish peroxidase (HRP) and 10-Acetyl-3,7-dihydroxyphenoxazine is used as a HRP substrate to visualize HRP activity.

In still yet an even further embodiment, the acetyltransferase is a recombinant histone acetyltransferase 1 (HAT1) that is produced in a human cell line.

In still yet an even further embodiment, the human cell line is HEK-293f.

In still yet an even further embodiment, RBAP46 is co-expressed with HAT1 within the human cell line.

In still yet an even further embodiment, the human cells are grown in the presence of acetate, forskolin, orthovanadate, or AICAR.

In still yet an even further embodiment, the acetyltransferase transfer reaction occurs in a solution with EDTA, DTT, or both.

In an embodiment for agonizing a histone acetyltransferase 1 reaction, a H4 histone, a histone acetyltransferase 1 (HAT1), and an acetyl CoA is provided. An agonist is added to the HAT1. The agonist is 2-(Hydroxymethyl)-6-[1,3,4-trihydroxy-1-(2-phenyltriazol-4-yl)butan-2-yl]oxyoxane-3,4,5-triol or 1-(1H-Benzimidazol-2-yl)hexane-1,2,3,4,5,6-hexol; 2,3-dihydroxybutanedioic acid.

In an embodiment for antagonizing a histone acetyltransferase 1 reaction, a H4 histone, a histone acetyltransferase 1 (HAT1), and an acetyl CoA is provided. An antagonist is added to the HAT1. The antagonist is nogalarol, 3-[3,4-Dihydroxy-5-(hydroxymethyl)oxolan-2-yl]-6,7-dihydroxy-6-methyl-5,7-dihydroimidazo[1,2-a]purin-9-one, daunomycin 3-oxime hydrochloride, rhodomycin A, aclacinomycin A1, cinerubin B, Methyl (1R,2R,4S)-4-[5-[5-(4,5-dihydroxy-6-methyloxan-2-yl)oxy-4-hydroxy-6-methyloxan-2-yl]oxy-4-(dimethylamino)-6-methyloxan-2-yl]oxy-2-ethyl-2,5,7,10-tetrahydroxy-6,11-dioxo-3,4-dihydro-1H-tetracene-1-carboxylate, nagalomycin C, N, N-Dibenzyldaunorubicin, or pyrromycin.

In an embodiment to treat an individual having a neoplasm, an individual having a neoplasm is administered an antagonist of HAT1.

In another embodiment, the antagonist is nogalarol, 3-[3,4-Dihydroxy-5-(hydroxymethyl)oxolan-2-yl]-6,7-dihydroxy-6-methyl-5,7-dihydroimidazo[1,2-a]purin-9-one, daunomycin 3-oxime hydrochloride, rhodomycin A, aclacinomycin A1, cinerubin B, Methyl (1R,2R,4S)-4-[5-[5-(4,5-dihydroxy-6-methyloxan-2-yl)oxy-4-hydroxy-6-methyloxan-2-yl]oxy-4-(dimethylamino)-6-methyloxan-2-yl]oxy-2-ethyl-2,5,7,10-tetrahydroxy-6,11-dioxo-3,4-dihydro-1H-tetracene-1-carboxylate, nagalomycin C, N, N-Dibenzyldaunorubicin, or pyrromycin.

In yet another embodiment, the antagonist is nogalarol.

In a further embodiment, the antagonist is 3-[3,4-Dihydroxy-5-(hydroxymethyl)oxolan-2-yl]-6,7-dihydroxy-6-methyl-5,7-dihydroimidazo[1,2-a]purin-9-one.

BRIEF DESCRIPTION OF THE DRAWINGS

The description and claims will be more fully understood with reference to the following figures and data graphs, which are presented as exemplary embodiments of the invention and should not be construed as a complete recitation of the scope of the invention.

FIG. 2 provides an embodiment of a method to assay modulators of acetyltransferase enzymes.

FIG. 3A provides various embodiments of HAT1 agonists.

FIGS. 3B to 3D provide various embodiments of HAT1 antagonists.

FIG. 5 provides data graphs of optimizing activity of recombinant HAT1 enzyme for use in assay, utilized in various embodiments.

FIGS. 7A and 7B provide data of inhibitors with varying modulation of HAT1 activity, utilized in various embodiments.

FIG. 17 provides the genomic coordinate of chromatin peaks identified in a HAT1 and Rbap46 ChIP-seq assays, utilized in various embodiments.

FIG. 30 provides immunoblots and data graphs of histone expression and ChIP-seq binding of histones in hTert-HME1 cells transduced with shRNAs for HAT1, utilized in various embodiments.

FIG. 31 provides ChIP-seq binding and ATAC-seq profiles of the HIST1H4E and RBBP4 loci in hTert-HME1 cells transduced with shRNAs for HAT1, utilized in various embodiments.

FIG. 32 provides data graphs on cell proliferation of hTert-HME1 cells transduced with shRNAs for HAT1 and with either an active or mutated-inactive HAT1 expression constructs, utilized in various embodiments.

FIG. 33 provides immunoblots and data graphs of hTert-HME1 cells transduced with shRNAs for HAT1 and treated with acetate, utilized in various embodiments.

FIG. 34 provides luciferase expression results of the H4E promoter with and without the H4-box and treated with acetate, utilized in various embodiments.

FIG. 39 provides H3K9ac ChIP-seq data of synchronized hTert-HME1 cells transduced with shRNAs for HAT1, utilized in various embodiments.

FIG. 44 provides luciferase expression results of the H4E promoter with and without the H4-box and treated with glucose, utilized in various embodiments.

DETAILED DESCRIPTION

Figure 1:
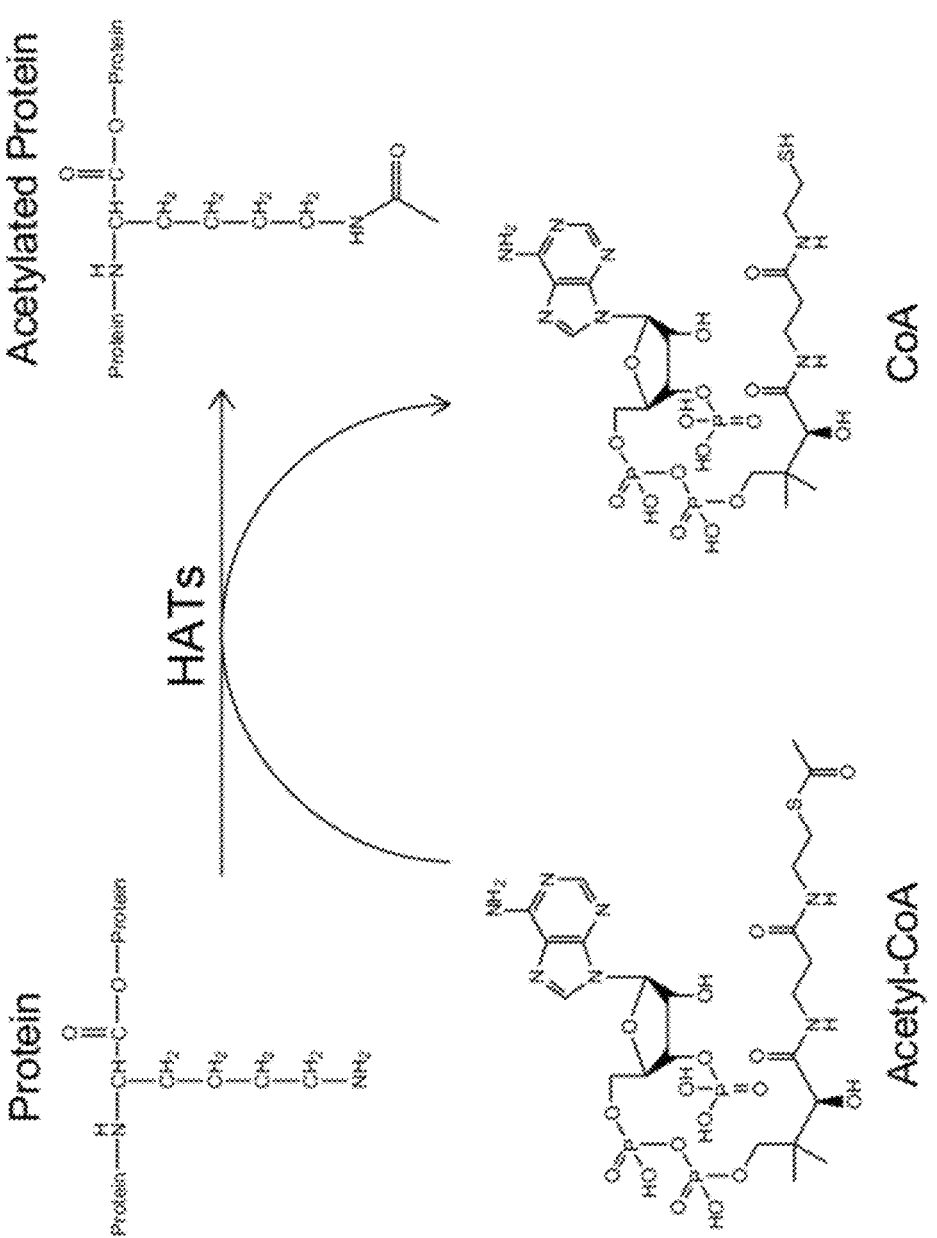
FIG. 1 provides a reaction schematic of histone acetyltransferases.

Turning now to the drawings and data, methods and processes to identify modulators of histone acetyltransferase 1 (HAT1) and applications thereof are described, in accordance with various embodiments of the invention. This current application is built upon the observation that HAT1 is a growth factor-regulated HAT, and is required for epithelial growth factor (EGF) and glucose-stimulated proliferation. Furthermore, HAT1 is shown herein that it is associated with poor outcome in malignancies. Inhibition of HAT1 would yield great benefit to neoplastic growth related to HAT1-stimulated proliferation.

Currently, chemical inhibitors of the HAT1 enzyme (and other acetyltransferases) are unknown or not in the public domain. As described herein, several embodiments are directed towards high-throughput enzymatic assays of acetyltransferase (e.g., HAT1) enzymatic activity and compound screens to identify chemical modulators of the acetyltransferase. In many embodiments, a substrate capable of being acetylated is provided. Substrates can be any appropriate biomolecule that is acetylated by an acetyltransferase, including (but not limited to) peptides, nucleic acids, metabolites, hormones, and neurotransmitters. In several embodiments, a substrate is mixed with acetyl donor, an acetyltransferase enzyme, and a putative modulator such that the acetyltransferase enzyme utilizes the acetyl donor to acetylate the substrate and the modulator can agonize or antagonize the reaction. Further, in many embodiments, acetylation is measured by labeling the acetyl groups that transferred onto the substrate with a reporter molecule. In some embodiments, Cu (I)-catalyzed alkyne-azide cycloaddition click chemistry is utilized to label acetyl groups with a reporter molecule.

In one embodiment to assay activity of HAT1, an n-terminal peptide of histone H4 is utilized. In its natural setting, HAT1 acetylates lysines 5 and 12 of H4 and thus the n-terminus of the protein can be utilized as a substrate. The peptide is conjugated to biotin. In vitro acetylation reactions are performed with recombinant HAT1 and 4-pentynoyl Co-A, an acetyl-Co-A substrate mimetic with an alkyne click handle for Cu (I)-catalyzed alkyne-azide cycloaddition click chemistry. The biotinylated peptide is captured on neutravidin-coated wells of a 96-well plate. Click chemistry is used to conjugate biotin-azide to the alkyne-containing lysine residues. Then streptavidin-HRP is added, which leads to a redox-dependent generation of a fluorescent molecule from the substrate 10-Acetyl-3,7-dihydroxyphenoxazine. Fluorescence is measured in 96-well plate reader.

A number of embodiments are also drawn to virtual screening of HAT (e.g., HAT1) enzymatic activity. In several of these embodiments, X-ray crystallography of a HAT enzyme is utilized to find chemical compounds that can modulate activity.

Compounds have been identified as putative candidates to modulate HAT1 activity. Agonists include 2-(Hydroxymethyl)-6-[1,3,4-trihydroxy-1-(2-phenyltriazol-4-yl)butan-2-yl]oxyoxane-3,4,5-triol and 1-(1H-Benzimidazol-2-yl)hexane-1,2,3,4,5,6-hexol; 2,3-dihydroxybutanedioic acid. Antagonists include nogalarol, 3-[3,4-Dihydroxy-5-(hydroxymethyl)oxolan-2-yl]-6,7-dihydroxy-6-methyl-5,7-dihydroimidazo[1,2-a]purin-9-one, daunomycin 3-oxime hydrochloride, rhodomycin A, aclacinomycin A1, cinerubin B, Methyl (1R,2R, 4S)-4-[5-[5-(4,5-dihydroxy-6-methyl-oxan-2-yl)oxy-4-hydroxy-6-methyloxan-2-yl]oxy-4-(dimethylamino)-6-methyloxan-2-yl]oxy-2-ethyl-2,5,7,10-tetrahydroxy-6,11-dioxo-3,4-dihydro-1H-tetracene-1-carboxylate, nagalomycin C, N, N-Dibenzyldaunorubicin, and pyrromycin.

In numerous embodiments, identified modulators of HAT1 are utilized in various medical treatments. In some embodiments, HAT1 antagonists are utilized in treatments of neoplasia, such as cancer and especially in treatments of cancer with high epithelial growth factor (EGF) activity. In a number of embodiments, individuals with cancer are administered a HAT1 antagonist.

Assays to Identify Modulators of Acetyltransferase Activity

Several embodiments are directed towards methods and reagents to identify modulators of acetyltransferase activity. In many embodiments, small molecules, biomolecules, and the like are analyzed for their ability to modulate (i.e., increase or decrease) acetyltransferase activity. Accordingly, in a number of embodiments, an assay is utilized in which acetyltransferase activity can be measured and the ability of a modulator to alter acetyltransferase activity can be determined. In many embodiments, an assay measures the ability of a particular acetyltransferase enzyme to transfer acetyl groups from one biomolecule to another. Acetyltransferase enzymes include (but are not limited to) histone acetyltransferases, choline acetyltransferase, chloramphenicol acetyltransferase, serotonin N-acetyltransferase, NatA acetyltransferase, and NatB acetyltransferase. It is to be understood that various acetyltransferases will transfer acetyl groups from a particular set of donor molecules onto particular biomolecule substrates. Donor molecules include (but are not limited to) acetyl coenzyme A and 4-pentynoyl Co-A. Biomolecule substrates include peptides, nucleic acids, metabolites, hormones, and neurotransmitters. Typically, substrate biomolecules have available amino groups or hydroxyl groups that can be acetylated.

In a number of embodiments, a computational method can be utilized to identify potential compounds that can modulate acetyltransferase activity. Generally, utilizing a published structure of the acetyltransferase, a library of putative compounds can be virtually screened to determine their ability dock within the active site or an allosteric site. For example, in some embodiments, Schrodinger software can be utilized for virtual screening (Schrodinger of New York, NY www.schrodinger.com). Additionally, conformational isomers of a library can also be analyzed of their ability to dock in various poses. For example, in some embodiments, the GLIDE docking program of Schrodinger software can be utilized to analyze conformational isomers. Various filters can be utilized to screen the conformational isomers. In addition, conformational isomers undergo energy minimalizing with an optimized potentials for liquid simulations (OPLS) force field model. Based on the virtual screen, compounds can be scored and ranked. It is to be understood that any appropriate method for virtual screening of compounds can be utilized within various embodiments of the invention.

Provided in FIG. 2 is an embodiment of a method to perform an acetyltransferase activity assay. In this embodiment, an acetyltransferase, acetyl donor molecule, and a substrate are combined such that the acetyltransferase is capable of transferring the acetyl group from the donor to the substrate. Putative modulators are added to the reaction and their ability to modulate acetyltransferase activity is measured.

The method of FIG. 2 can begin by providing (201) a substrate with available reactive groups to be acetylated by an acetyltransferase enzyme. Typically, the substrate is a biomolecule that mimics the natural substrate that the acetyltransferase enzyme recognizes in vivo. Any appropriate biomolecule can be utilized as appropriate to the acetyltransferase enzyme being assessed, including (but not limited to) peptides, nucleic acids, metabolites, hormones, and neurotransmitters. The substrate should include available functional groups that can be acetylated, such as amine or hydroxyl groups. If the substrate is a protein, a peptide inclusive of the amino acids to be acetylated can be utilized. The substrate can be fixed to a surface such that it is held in place. For example, the substrate can include a biotin molecule and be fixed to a surface of streptavidin (or similar) molecules.

For example, in some embodiments, the acetyltransferase enzyme to be assessed is HAT1 and the substrate is a mimic of H4. The substrate should mimic lysine 5 (K5), lysine 8 (K8), lysine 12 (K12), lysine 16 (K16) or any combination thereof of H4, as these amino acids have been reported acetylated in vivo. In some embodiments, the substrate is a peptide of H4 inclusive of K5 and K12. In some embodiments, the substrate is a peptide of H4 having 10 to 50 amino acids. In some embodiments, the substrate is a peptide of H4 having the following sequence: SGRGKGGKGLGKG-GAKRHRKVLR (SEQ. ID No. 1). In some embodiments, the substrate is a peptide derived from H2A, H2B or H3 (eg., n-terminal peptide of H3). Other peptides inclusive of lysine residues derived from other peptides can be utilized as well.

As shown in FIG. 2, an acetyl-like donor and the acetyltransferase enzyme are mixed (203) with the substrate. In addition, a putative modulator is added to the mixture to assess its ability modulate the activity of the acetyltransferase enzyme. The activity of any appropriate acetyltransferase enzyme can be assessed, including (but not limited to) histone acetyltransferases, choline acetyltransferase, chloramphinocol acetyltransferase, serotonin N-acetyltransferase, NatA acetyltransferase, and NatB acetyltransferase. The appropriate donor molecule should be utilized. Typically, an acetyltransferase enzyme is produced and concentrated to be utilized in an extracellular reaction. One mechanism for producing an enzyme is to express the enzyme in a recombinant system and then purifying the protein via immunoprecipitation. For many acetyltransferase enzymes, the appropriate donor molecule is an acetyl coA or a mimic of acetyl coA.

Modulators to be assessed include (but are not limited to) small molecules and biomolecules (e.g., peptides, nucleic acids, etc.). Libraries of modulators can be virtually screened, which may help reduce the number of modulators to be assessed.

Some embodiments assess the ability of modulators on the activity of HAT1 on H4. Accordingly, a H4 substrate is provided and mixed with a donor (e.g., acetyl CoA or 4-pentynoyl CoA), HAT1 enzyme, and putative modulators in an appropriate buffer. The HAT1 enzyme will acetylate the H4 substrate utilizing the donor, resulting in acetylated H4. Modulation of acetylation activity by a modulator can be assessed.

The acetyl-like groups that have been transferred onto the substrate by the acetyltransferase enzyme are labeled (205) such that a reporter molecule is conjugated onto the acetyl-like groups. In many instances, click chemistry is performed via azide-alkyne cycloaddition on acetyl-like groups to label these groups with a reporter molecule. Accordingly, when azide-alkyne cycloaddition is utilized, an azide or alkyne is an appendage on the acetyl-like group and the reporter molecule has an appendage of the other. For instance, an acetyl-like group can have an alkyne appendage and the reporter molecule can have an azide appendage, and vice versa. For example, the donor molecule 4-pentynoyl CoA is a mimic of acetyl CoA with an alkyne appendage extending from the acetyl group. When the acetylation is performed on the substrate with 4-pentynoyl CoA, the alkyne appendage is transferred as part of the acetyl group onto the substrate. The alkyne can then act as a substrate for a click chemistry reaction to add a reporter molecule.

By conjugating a reporter molecule to the acetyl-like groups, the amount of acetyl-like groups transferred onto the substrate can be determined (207). Any appropriate reporter molecule can be conjugated to the acetyl-like groups, including (but not limited to) fluorophores, radioisotopes, biotin/streptavidin-conjugated enzyme, and antigen binding molecules (e.g., antibody). In some instances, horse radish peroxidase (HRP) is utilized as a conjugated enzyme in a biotin/streptavidin reporter system. Accordingly, biotin can be conjugated to an azide/alkyne and HRP can be conjugated to streptavidin. Utilizing click chemistry, biotin is conjugated to the acetyl-like group and then HRP-streptavidin is added thereupon. The HRP that binds to the acetyl-like group can be utilized to perform an oxidation reaction on a substrate to elicit a chromophore that can be detected.

While specific examples of processes for assessing modulators of acetyltransferases are described above, one of ordinary skill in the art can appreciate that various steps of the process can be performed in different orders and that certain steps may be optional according to some embodiments of the invention. As such, it should be clear that the various steps of the process could be used as appropriate to the requirements of specific applications. Furthermore, any of a variety of processes for assessing modulators of acetyltransferases appropriate to the requirements of a given application can be utilized in accordance with various embodiments of the invention.

Modulators of Histone Acetyltransferase 1

Figures 3A, 3B:
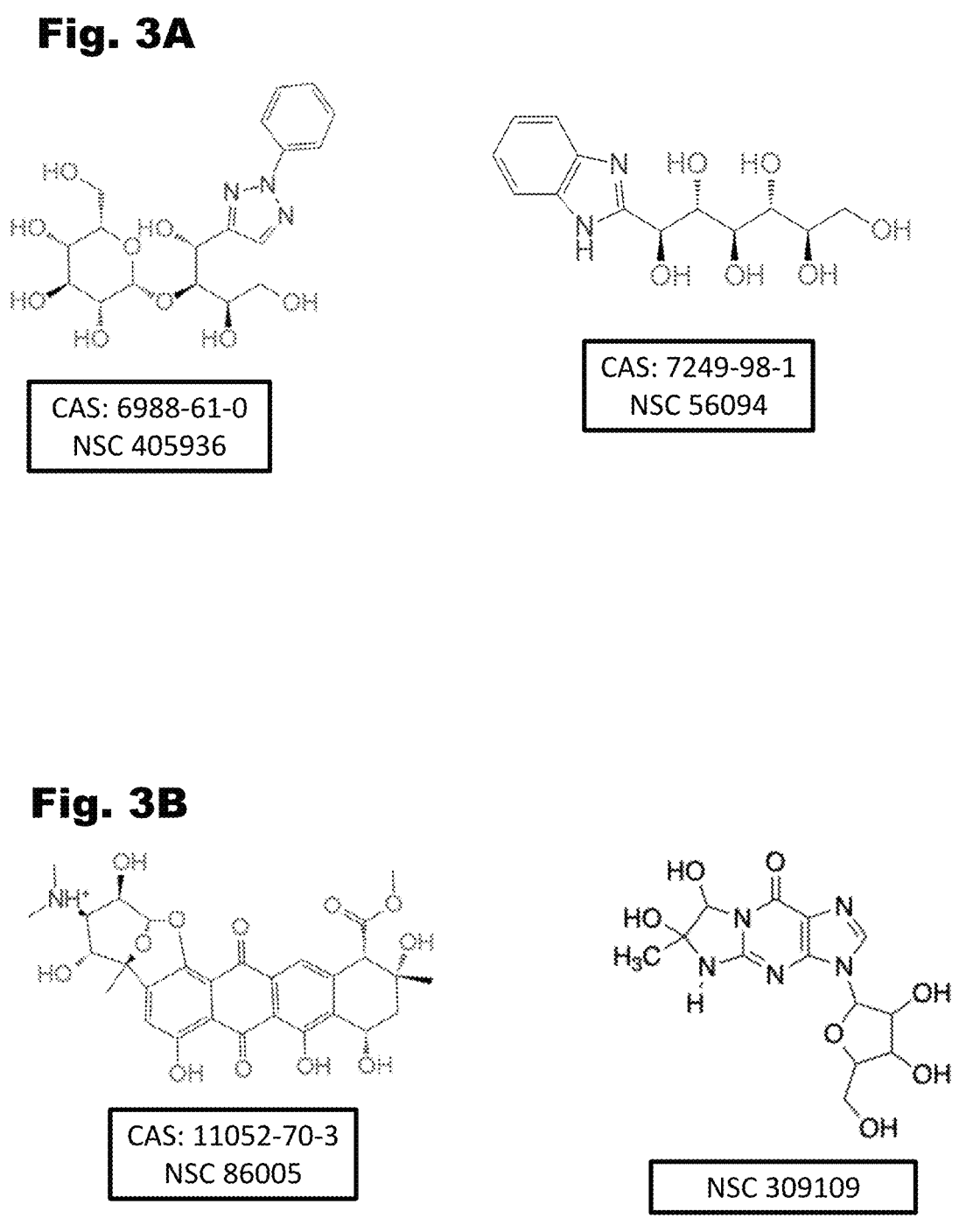
Figure 3C:
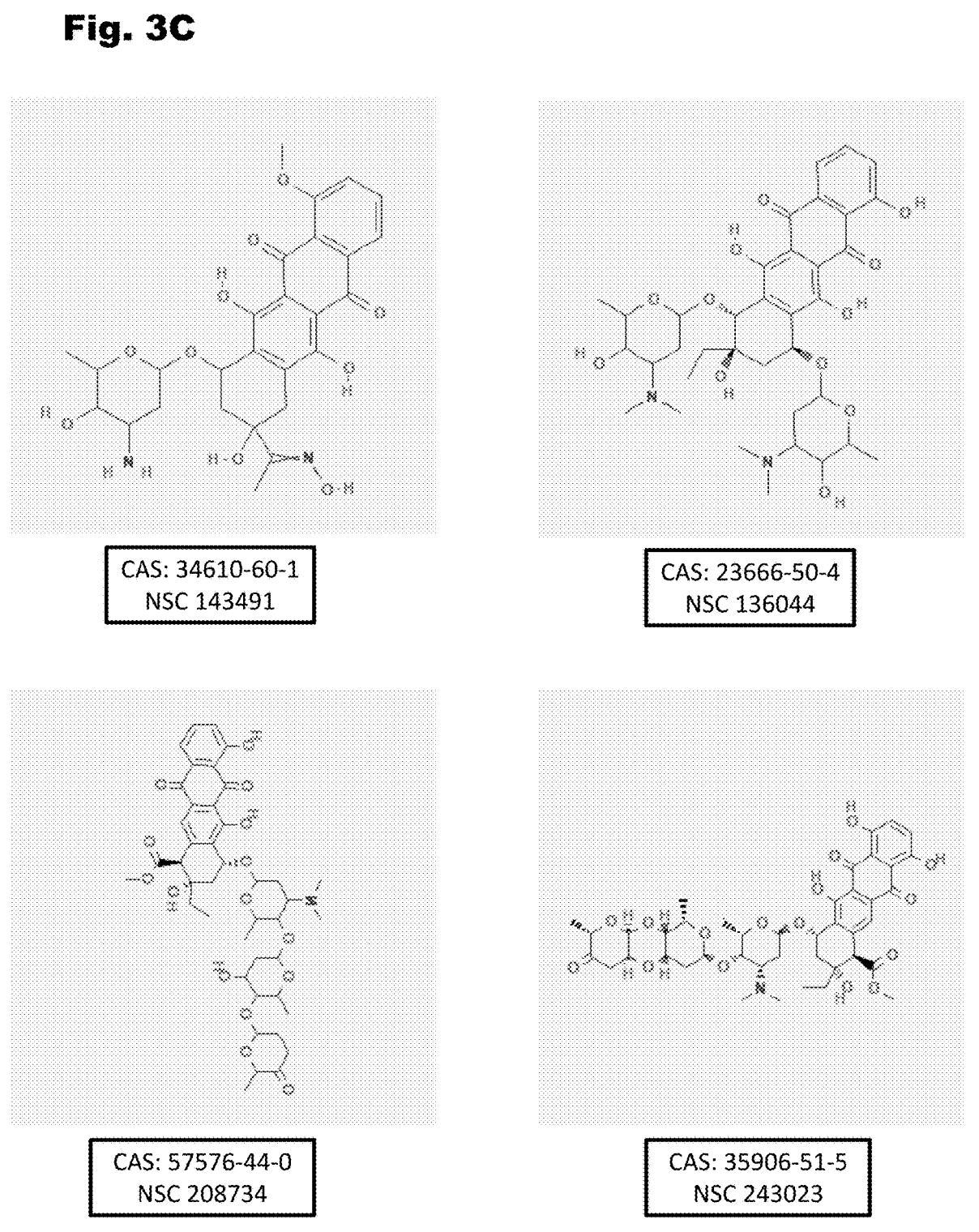
Figure 3D:
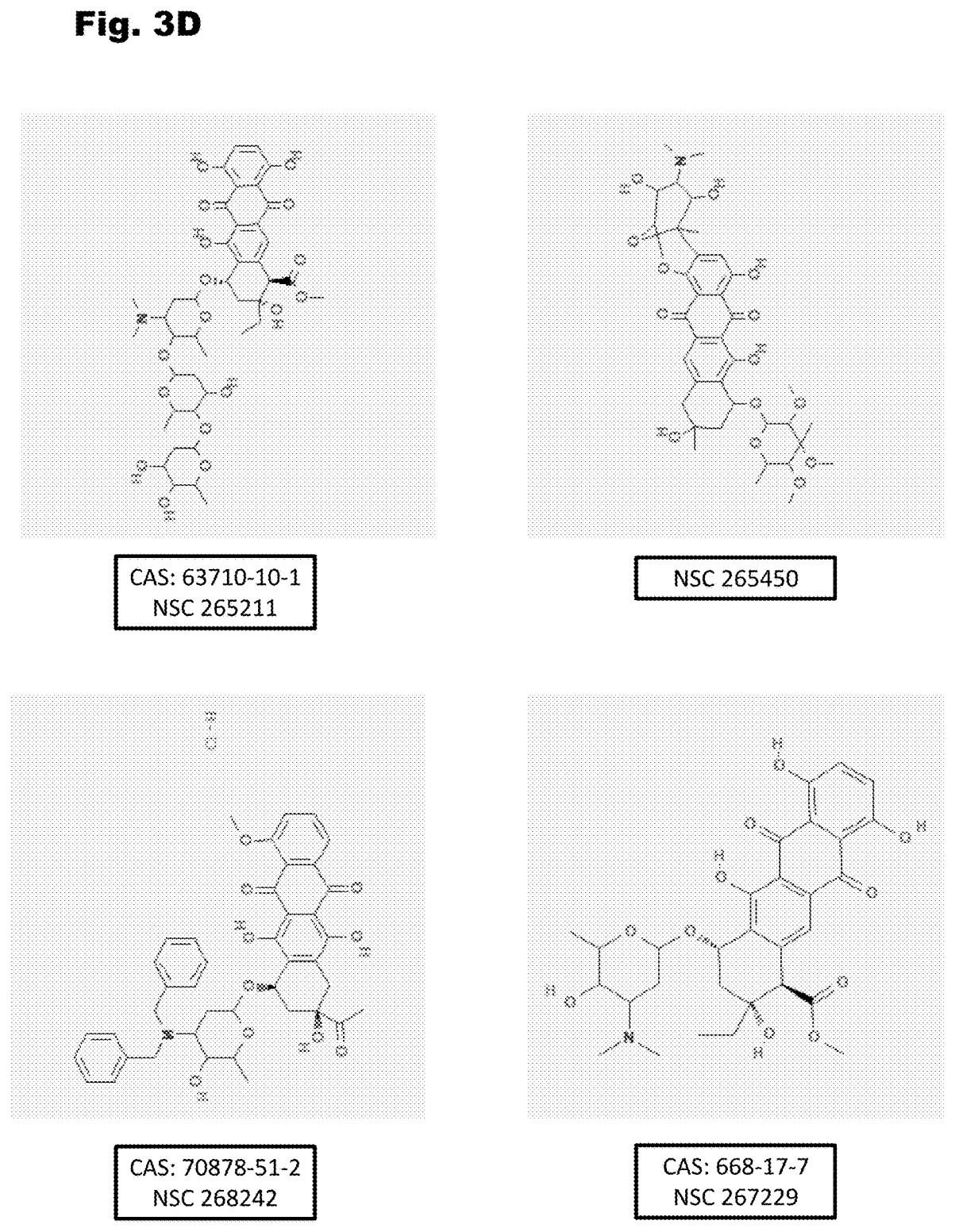

A number of modulators of HAT1 have been identified (FIGS. 3A-3D). Two agonists identified include 2-(Hydroxymethyl)-6-[1,3,4-trihydroxy-1-(2-phenyltriazol-4-yl)butan-2-yl]oxyoxane-3,4,5-triol (CAS: 6988-61-0 and NSC 405936) and 1-(1H-Benzimidazol-2-yl)hexane-1,2,3,4,5,6-hexol; 2,3-dihydroxybutanedioic acid (CAS: 7249-98-1 and NSC 56094) (FIG. 3A). Antagonists identified include nogalarol (CAS: 11052-70-3 and NSC 86005) and 3-[3,4-Dihydroxy-5-(hydroxymethyl)oxolan-2-yl]-6,7-dihydroxy-6-methyl-5,7-dihydroimidazo[1,2-a]purin-9-one (NSC 309109) (FIG. 3B). Several nogalarol analogs also inhibit HAT1 activity, including daunomycin 3-oxime hydrochloride (CAS: 34610-60-1 and NSC 143491), rhodomycin A (CAS: 23666-50-4 and NSC 136044), aclacinomycin A1 (CAS: 57576-44-0 and NSC 208734), cinerubin B (CAS: 35906-51-5 and NSC 243023), Methyl (1R,2R,4S)-4-[5-[5-(4,5-dihydroxy-6-methyloxan-2-yl)oxy-4-hydroxy-6-methyloxan-2-yl]oxy-4-(dimethylamino)-6-methyloxan-2-yl]oxy-2-ethyl-2,5,7,10-tetrahydroxy-6,11-dioxo-3,4-dihydro-1H-tetracene-1-carboxylate (CAS: 63710-10-1 and NSC 265211), nagalomycin C (NSC 265450), N, N-Dibenzyldaunorubicin (CAS: 70878-51-2 and NSC 268242), and pyrromycin (CAS: 668-17-7 and NSC 267229) (FIGS. 3C and 3D).

Note CAS refers to Chemical Abstracts Service registry number provided by the American Chemical society (www.cas.org). Note NSC refers to National Service Center numeric identifier for substances submitted to the National Cancer institute for testing and evaluation (cactus.nci.nih.gov/ncidb2.2/).

Treatments Utilizing Antagonists of HAT1

Various embodiments are directed to treatments of neoplasms and cancer utilizing antagonists of HAT1. It is now known that HAT1 acetylation increases EGF-dependent nutrient supply and promotes S-phase progression and cell proliferation, thus promoting cancerous growth. In addition, high expression of HAT1 within cancerous tissue associates with poor outcomes. Based on these findings, antagonists of HAT1 provide a means to treat cancer, especially cancers involving upregulation of EGF.

In many embodiments, medications are administered in a therapeutically effective amount as part of a course of treatment. As used in this context, to "treat" means to ameliorate at least one symptom of the disorder to be treated or to provide a beneficial physiological effect. For example, one such amelioration of a symptom could be reduction of neoplastic cells and/or tumor size.

A therapeutically effective amount can be an amount sufficient to prevent reduce, ameliorate or eliminate the symptoms of diseases or pathological conditions susceptible to such treatment, such as, for example, neoplasms, cancer, or other diseases that may be responsive to anthracycline treatment. In some embodiments, a therapeutically effective amount is an amount sufficient to reduce to induce toxicity in a neoplasm.

As described herein, various neoplasms and cancers can be treated with a HAT1 antagonist. HAT1 antagonists to be used in treatments include (but are not limited to) nogalarol, 3-[3,4-Dihydroxy-5-(hydroxymethyl)oxolan-2-yl]-6,7-dihydroxy-6-methyl-5,7-dihydroimidazo[1,2-a]purin-9-one, daunomycin 3-oxime hydrochloride, rhodomycin A, aclacinomycin A1, cinerubin B, Methyl (1R,2R,4S)-4-[5-[5-(4,5-dihydroxy-6-methyloxan-2-yl)oxy-4-hydroxy-6-methyloxan-2-yl]oxy-4-(dimethylamino)-6-methyloxan-2-yl]oxy-2-ethyl-2,5,7,10-tetrahydroxy-6,11-dioxo-3,4-dihydro-1H-tetracene-1-carboxylate, nagalomycin, N,N-Dibenzyldaunorubicin, and pyrromycin. In various embodiments, HAT1 inhibitors can be utilized in an adjuvant or a neoadjuvant treatment regime. An adjuvant treatment comprises utilizing anthracycline after surgical excision of a tumor. A neoadjuvant treatment comprises utilizing anthracycline prior to surgical intervention, which may reduce tumor size or improve tumor margins.

In several embodiments, any class of neoplasms can be treated, but especially cancers exhibiting abnormal EGF activity including (but not limited to) adrenocortical carcinoma, bladder urothelial carcinoma, chromophobe renal cell carcinoma, lower-grade glioma, liver hepatocellular carcinoma, lung adenocarcinoma, non-small cell lung cancer, breast cancer, colorectal cancer, pancreatic cancer and gliomas including low-grade glioma and glioblastoma multiforme. HAT1 antagonists may be administered intravenously, intra-arterially, or intravesically. The appropriate dosing of a HAT1 antagonist is often determined by body surface are and varies by neoplasm type.

A number of additional or alternative treatments and medications are available to treat neoplasms and cancers, such radiotherapy, chemotherapy, immunotherapy, and hormone treatments. Classes of anti-cancer or chemotherapeutic agents can include alkylating agents, platinum agents, taxanes, *vinca* agents, anti-estrogen drugs, aromatase inhibitors, ovarian suppression agents, endocrine/hormonal agents, bisphosphonate therapy agents and targeted biological therapy agents. Medications include (but are not limited to) cyclophosphamide, fluorouracil (or 5-fluorouracil or 5-FU), methotrexate, thiotepa, carboplatin, cisplatin, taxanes, paclitaxel, protein-bound paclitaxel, docetaxel, vinorelbine, tamoxifen, raloxifene, toremifene, fulvestrant, gemcitabine, irinotecan, ixabepilone, temozolomide, topotecan, vincristine, vinblastine, eribulin, mutamycin, capecitabine, capecitabine, anastrozole, exemestane, letrozole, leuprolide, abarelix, buserelin, goserelin, megestrol acetate, risedronate, pamidronate, ibandronate, alendronate, zoledronate, and tykerb. Accordingly, an individual may be treated, in accordance with various embodiments, by a single medication or a combination of medications described herein. For example, common treatment combination is cyclophosphamide, methotrexate, and 5-fluorouracil (CMF). Furthermore, several embodiments of treatments further incorporate immunotherapeutics, including denosumab, bevacizumab, cetuximab, trastuzumab, pertuzumab, alemtuzumab, ipilimumab, nivolumab, ofatumumab, panitumumab, and rituximab. Various embodiments include a prolonged hormone/endocrine therapy in which fulvestrant, anastrozole, exemestane, letrozole, and tamoxifen may be administered.

Dosing and therapeutic regimens can be administered appropriate to the neoplasm to be treated, as understood by those skilled in the art. For example, 5-FU can be administered intravenously at dosages between 25 mg/m$^2$ and 1000 mg/m$^2$. Methotrexate can be administered intravenously at dosages between 1 mg/m$^2$ and 500 mg/m$^2$.

EXEMPLARY EMBODIMENTS

The embodiments of the invention will be better understood with the several examples provided within. Many exemplary methods and results acetyltransferase assays are described. Validation results are also provided.

Example 1: HAT1 Modulator Assay

Figure 4:
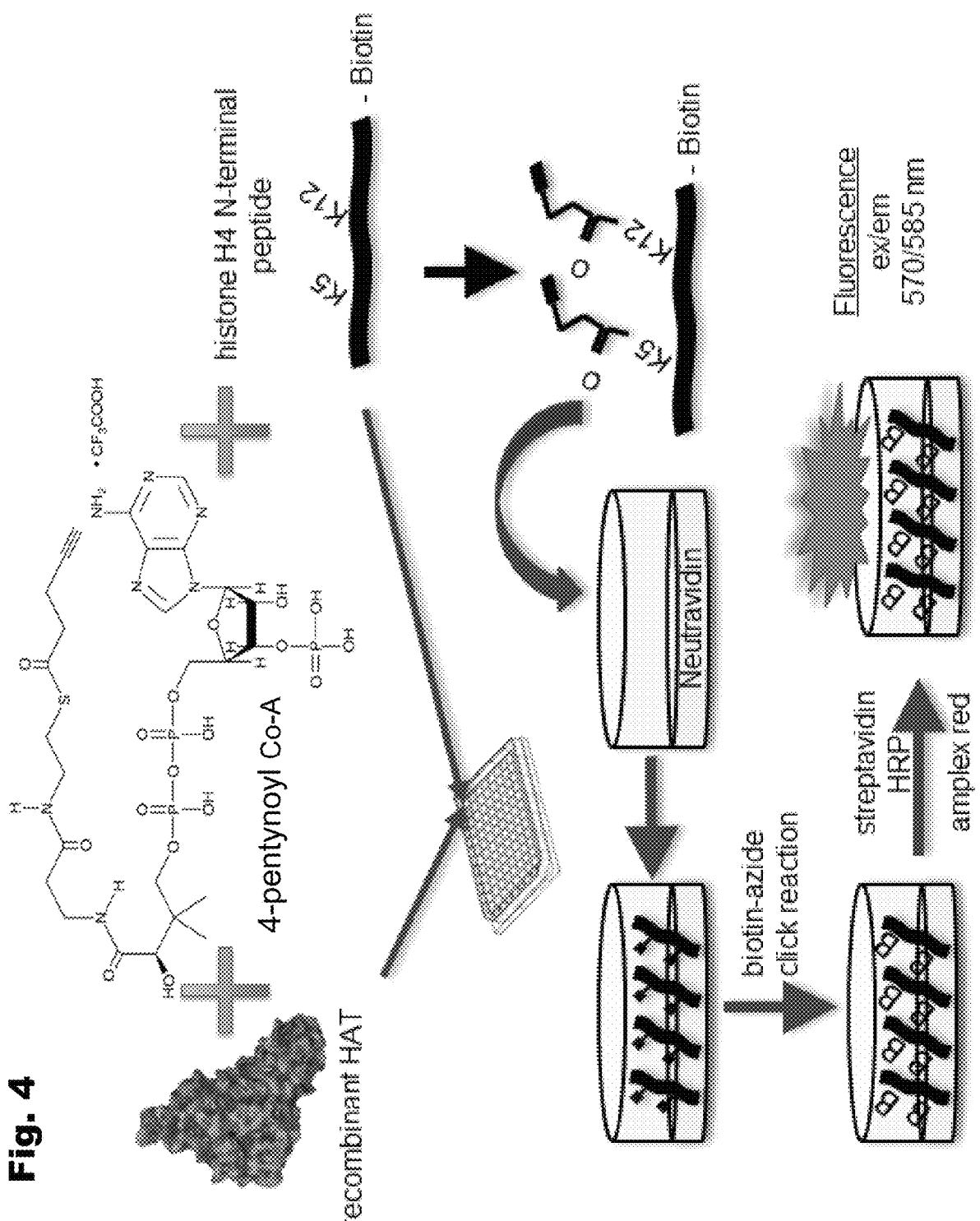
FIG. 4 provides an embodiment of a method to assay modulators of HAT1 utilizing 4-pentynoyl Co-A and click chemistry.

Provided in FIG. 4 is an exemplary embodiment of an experimental assay to identify modulators of HAT1. To begin the assay, a putative modulator is mixed with the substrate histone H4 N-terminal peptide, the acetyl-like donor 4-pentynonyl CoA, and recombinant HAT1. The H4 N-terminal peptide is the first 23 amino acids of H4 (SEQ. ID No. 1) with a biotin conjugated at the C-terminus of the peptide. Importantly, K5 and K12 of the H4 N-terminal peptide are available for di-acetylation. The 4-pentynoyl CoA is an acetyl CoA derivative having an alkyl extending from the acetyl group. The recombinant HAT1 is produced in human cells with a peptide tag DYKDDDDK (FLAG®), which is purified via immunoprecipitation.

Each reaction is carried out within a well of a 96-well plate for one hour at 37° C., resulting in pentynoylation of K5 and K12 of the substrate peptide. The reactions are transferred to a neutravidin-coated 96-well plate to capture the biotinylated peptide via a neutravidin-biotin interaction performed for one hour at room temperature. After washing the wells 3X with PBS-tween, the substrate peptides are exposed to biotinylated azide, which reacts with the pentynoyl groups in a copper (I) click chemistry reaction to further functionalize these appendages with biotin, which is performed at 37° C. for 1 hour. Substrates that were acetylated by HAT1 now have an available biotin extending from K5 and K12. After washing the wells 3X with PBS-tween, streptavidin-HRP is added to the well to bind to every available biotin for one hour at 37° C. After washing the wells 3X with PBS-tween, 10-Acetyl-3,7-dihydroxyphenoxazine (Amplex® Red ThermoFisher® Scientific, Waltham, MA) is added as a substrate of HRP and incubated for 30 minutes to produce a detectable fluorescence (570 nm excitation and 585 nm emission), which is measurable utilizing a plate reader.

Provided in FIG. 5 are few experimental results to enhance production and activity of recombinant HAT1. DYKDDDDK-tagged HAT1 was expressed in HEK-293f freestyle cells (ThermoFisher® Scientific) grown in suspension at 37° C. and 8% $CO_2$. As shown in the left panel of FIG. 5, co-expression of HAT1 with RBAP46 increased the production and activity of HAT1. As shown in the middle panel, various factors were added to the HEK-293f cells right after transfection with the HAT1 expression construct for 20 minutes to test their ability to increase HAT1 activation. Acetate (5 mM), forskolin (10 μM), orthovanadate (10 μM), and AICAR (10 μM) were tested. Forskolin provided the best results and thus utilized in recombinant HAT1 production.

The HAT1 enzymatic reaction conditions was also optimized, utilizing 0.1M EDTA, 0.1M DTT or both. As portrayed in the right panel of FIG. 5, 0.1M DTT provided the best activity and was utilized in the assay reaction.

Figure 6:
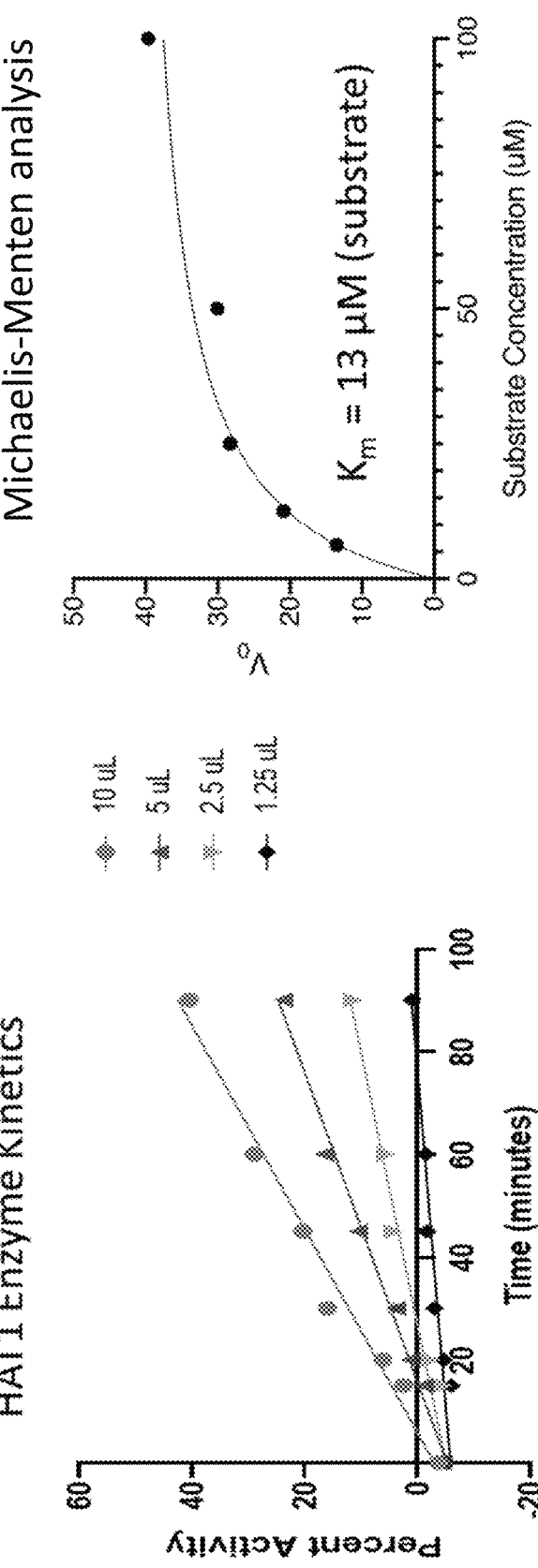
FIG. 6 provides data graphs of HAT1 enzyme kinetics and Michaelis-Menten analysis of recombinant HAT1 in an assay, utilized in various embodiments.

FIG. 6 provides HAT1 enzyme kinetics (left panel) and Michaelis-Menten analysis (right panel). To perform the enzyme kinetics, various amounts of input enzyme were tested in 20 uL reaction with the amount of activity measured over time. Based on these results, 10 uL of enzyme over 60 minutes was utilized in the assay. In the Michaelis-Menten analysis, H4 peptide substrate was varied to determine that the $K_m$ of HAT1 in these conditions is 13 μM. Assay reactions were run with 15 μM of substrate peptide.

To confirm that inhibition was measurable in the assay, two bisubstrate inhibitors were tested in the assay (FIGS. 7A and 7B). First, a bona fide inhibitor of HAT1 acetylation of H4: H4K12-Co A peptide (SEQ. ID No. 2) was utilized to measure inhibition of the assay, which did so with an IC50 of 1 μM (FIG. 7A). While this inhibitor can be used to validate the assay, it is not orally bioavailable or cell permeable and thus not a good candidate for treatments. In a second assay, lysyl CoA was tested, which is a known inhibitor of CBP/p300 acetyltransferase but not HAT1. The lysyl CoA did not inhibit HAT1 activity in the assay (FIG. 7B).

Figure 8:
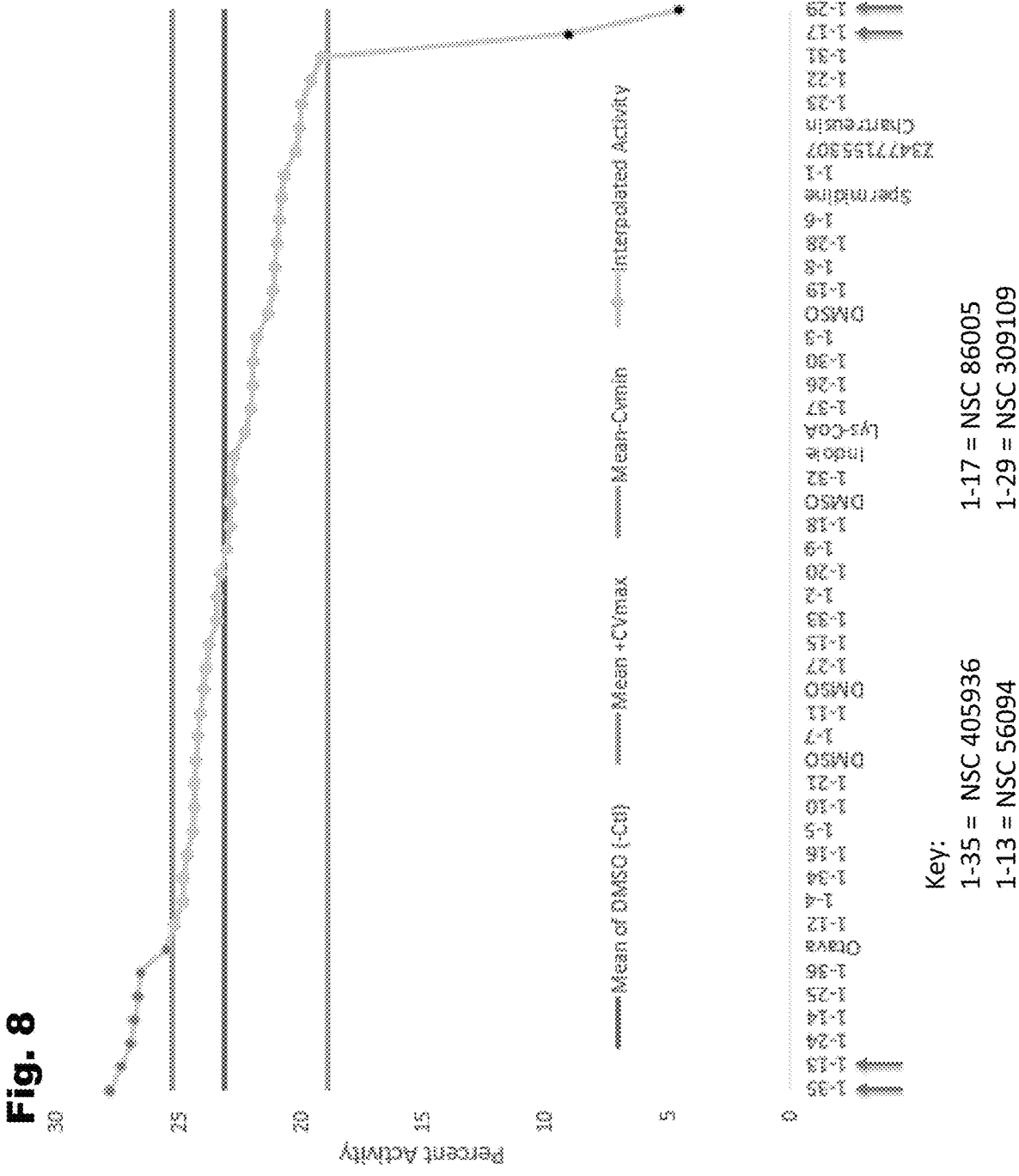
FIG. 8 provides a data graph of modulators assessed in a HAT1 assay, generated in accordance with various embodiments.

Fifty compounds were screened in the assay. Two compounds were found to be agonists: 2-(Hydroxymethyl)-6-[1,3,4-trihydroxy-1-(2-phenyltriazol-4-yl)butan-2-yl]oxyoxane-3,4,5-triol (NSC 405936) and 1-(1H-Benzimidazol-2-yl)hexane-1,2,3,4,5,6-hexol; 2,3-dihydroxybutanedioic acid (NSC 56094) (FIG. 8). Two compounds were found to be an antagonists: nogalarol (NSC 86005) and 3-[3,4-Dihydroxy-5-(hydroxymethyl)oxolan-2-yl]-6,7-dihydroxy-6-methyl-5,7-dihydroimidazo[1,2-a]purin-9-one (NSC 309109).

Figure 9:
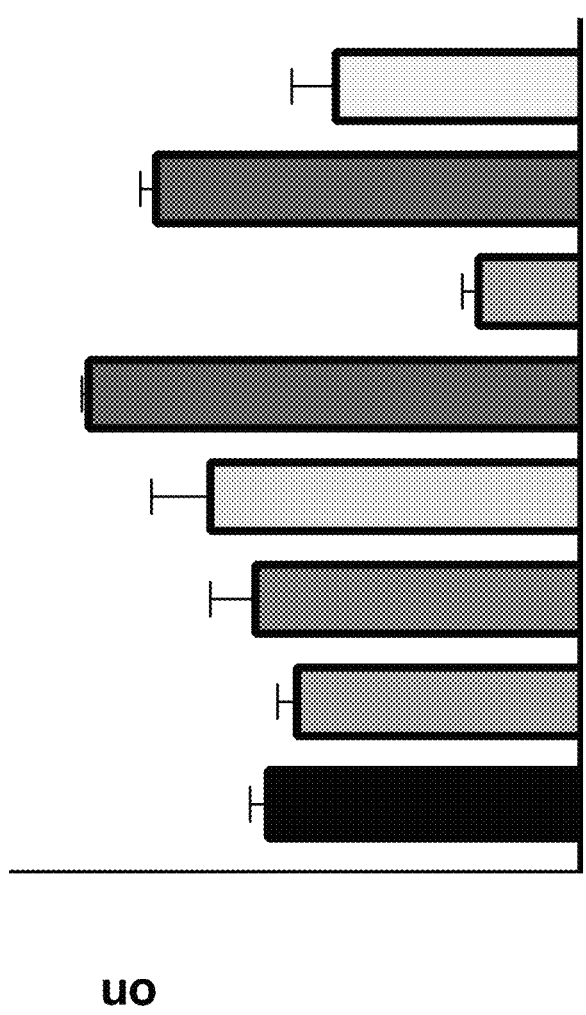
FIG. 9 provides a data graph of NSC 86005 analogs assessed in a HAT1 assay, generated in accordance with various embodiments.

To determine structure-activity relationship, several analogs of nogalarol were tested to determine their inhibition (FIG. 9). The analogs tested were daunomycin 3-oxime hydrochloride (NSC 143491), rhodomycin A (NSC 136044), aclacinomycin A1 (NSC 208734), cinerubin B (NSC 243023), Methyl (1R,2R,4S)-4-[5-[5-(4,5-dihydroxy-6-methyloxan-2-yl)oxy-4-hydroxy-6-methyloxan-2-yl]oxy-4-(dimethylamino)-6-methyloxan-2-yl]oxy-2-ethyl-2,5,7,10-tetrahydroxy-6,11-dioxo-3,4-dihydro-1H-tetracene-1-carboxylate (NSC 265211), nagalomycin C (NSC 265450), N,N-Dibenzyldaunorubicin (NSC 268242), and pyrromycin (NSC 267229). Each analog showed various ability to inhibit HAT1.

Figures 10, 11:
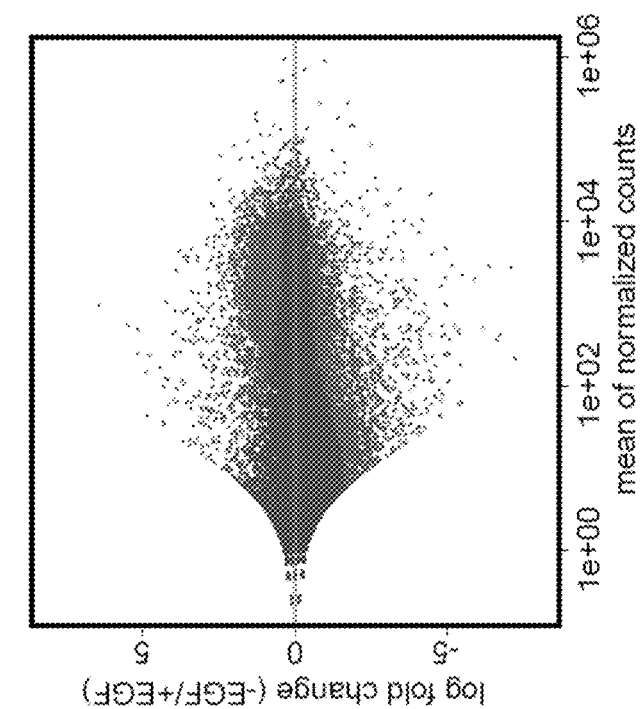
FIG. 10 provides growth curves of hTert-HME1 cells with and without EGF, utilized in various embodiments.
FIG. 11 provides gene expression profiling of hTert-HME1 cells with and without EGF, utilized in various embodiments.

Example 2: HAT1 Coordinates Histone Production and Acetylation Via H4 Promoter Binding HAT1 is an EGF-Stimulated Transcript Required for EGF-Dependent Proliferation Human mammary epithelial cells immortalized with telomerase (hTert-HME1) were dependent on epithelial growth factor (EGF) for log-phase cell division (FIG. 10). When EGF was removed from the culture medium cell division continued, but at a diminished rate (FIG. 10). To determine epigenetic regulators contributing EGF-dependent growth transcriptome analysis by RNA sequencing was performed after 2 passages (6 days) in either EGF-stimulated versus EGF-free media. Overall, 7117 genes were differentially expressed in the presence or absence of EGF (FIG. 11, FDR 0.1), of which 4313 were up-regulated and 2804 down-regulated upon EGF treatment.

Figure 12:
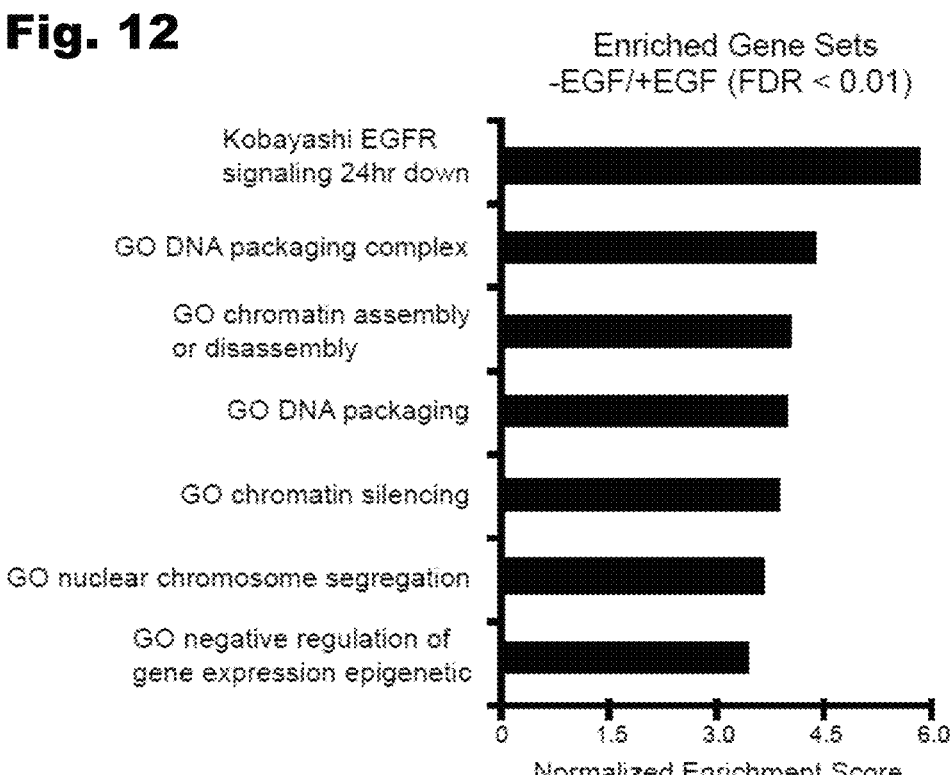
FIG. 12 provides gene set enrichment on differentially expressed genes identified in FIG. 11, utilized in various embodiments.
Figure 13:
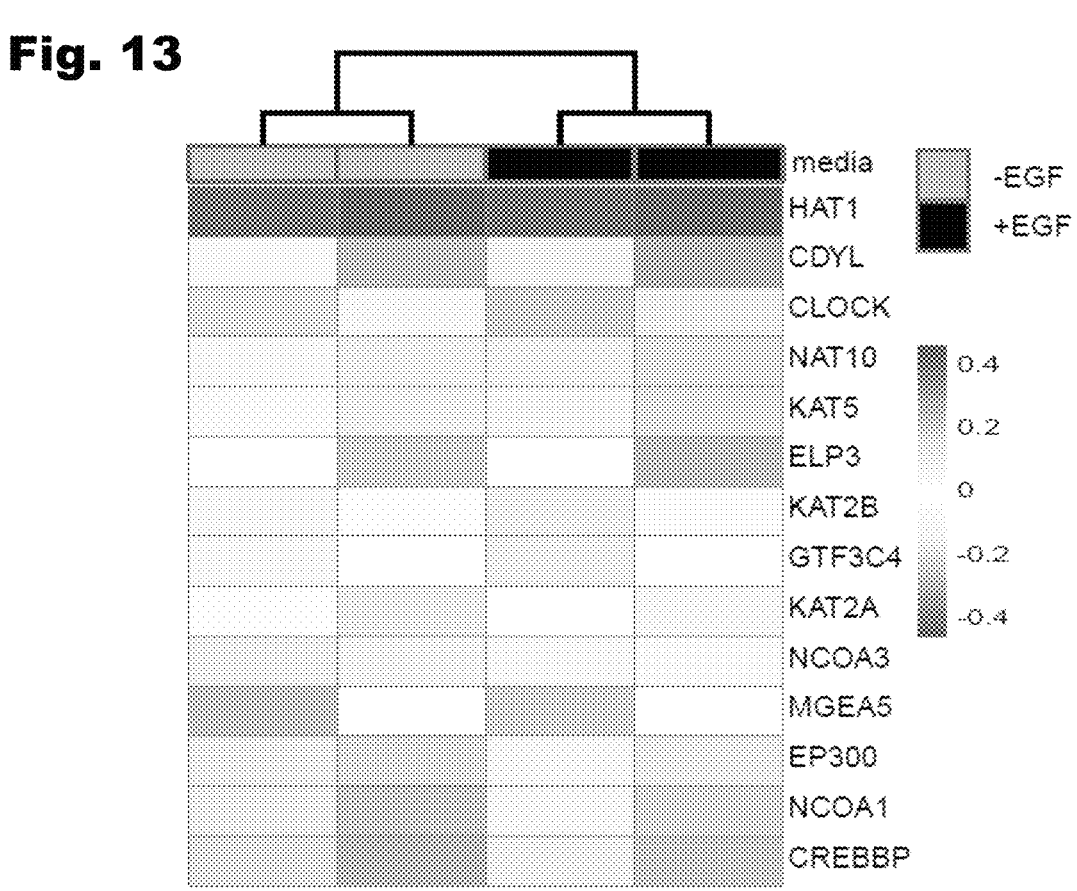
FIG. 13 provides gene expression value of histone acetyltransferases of hTert-HME1 cells with and without EGF, utilized in various embodiments.
Figure 14:
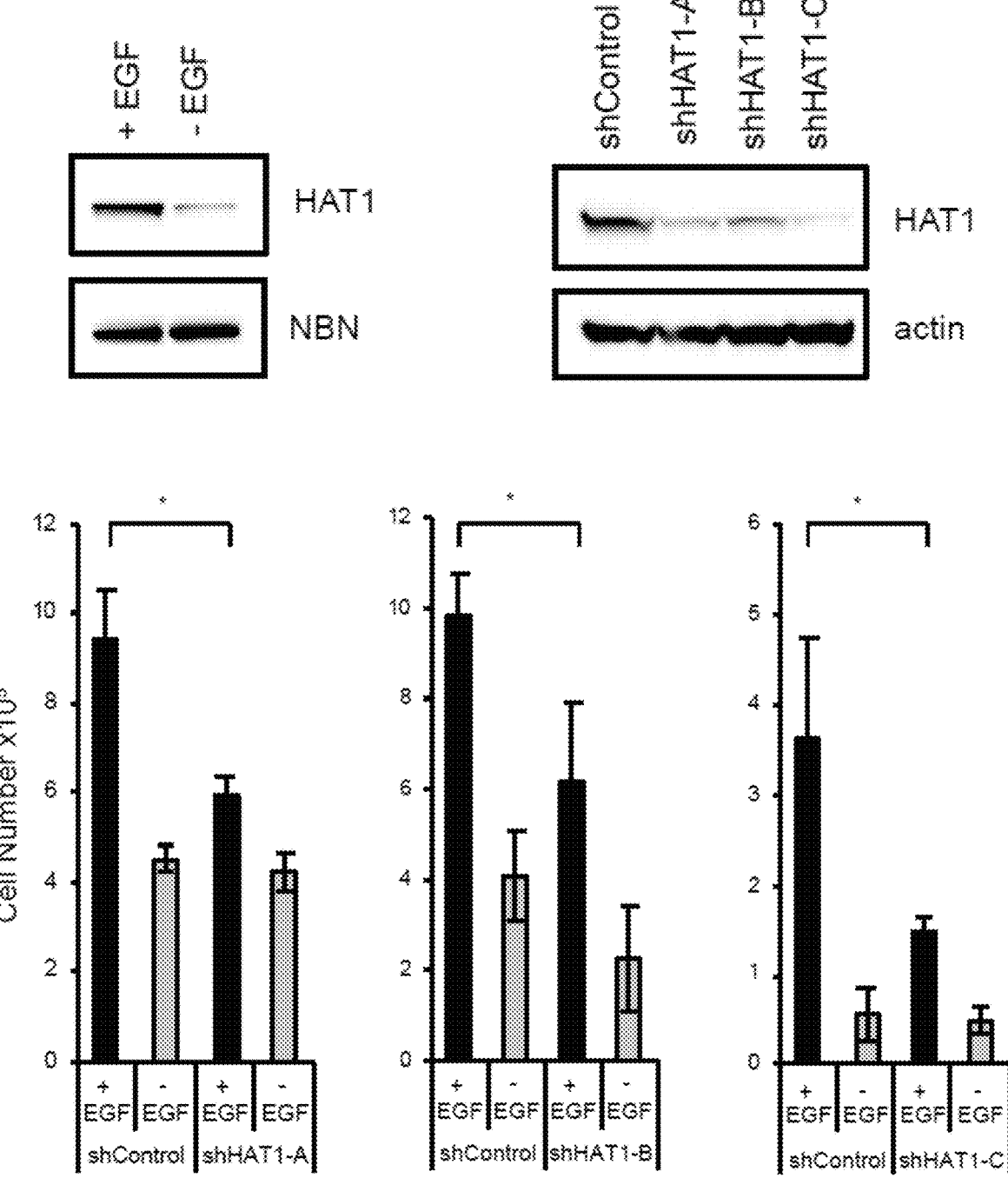
FIG. 14 provides data of the relationship between EGF and HAT1 in hTert-HME1 cells by varying EGF levels and HAT1 expression, utilized in various embodiments.

Gene set enrichment analysis performed on the differentially expressed genes revealed multiple gene sets involved in chromatin biology among the top candidates (FIG. 12). Epigenetic regulators were specifically focused on as a mechanism to understand the broad differences in gene expression observed. Gene ontology analysis identified 14 confirmed or putative genes that encoded proteins with HAT activity; these were selected for further analysis. Of these candidates, histone acetyltransferase 1 (HAT1) was the most strongly differentially expressed between +/−EGF conditions ($\log_2$ fold change 1.3; FDR<$1\times10^6$; FIG. 13). Immunoblotting confirmed that HAT1 protein levels were also stimulated by EGF and down-regulated in EGF-free conditions in an independent but similar cell line MCF10A (FIG. 14).

As HATs in general confer positive effects on gene expression it was tested whether HAT1 contributed to cell proliferation in EGF-stimulated conditions. Three independent shRNAs were used to reduce HAT1 protein levels in hTert-HME1 cells, compared to a control shRNA (FIG. 14). Each shRNA targeted to HAT1 diminished proliferation (mean 1.8+/−0.44-fold) in EGF-stimulated conditions, compared to control shRNA-treated cells (FIG. 14). In contrast, significant differences were not observed between HAT1 and control shRNAs in the EGF-free condition (FIG. 14). These data indicate that HAT1 provides a critical function in EGF-stimulated cell proliferation, but is not required for basal proliferation without EGF.

HAT1 Holoenzyme Binds Histone H4 Promoters

Figure 15:
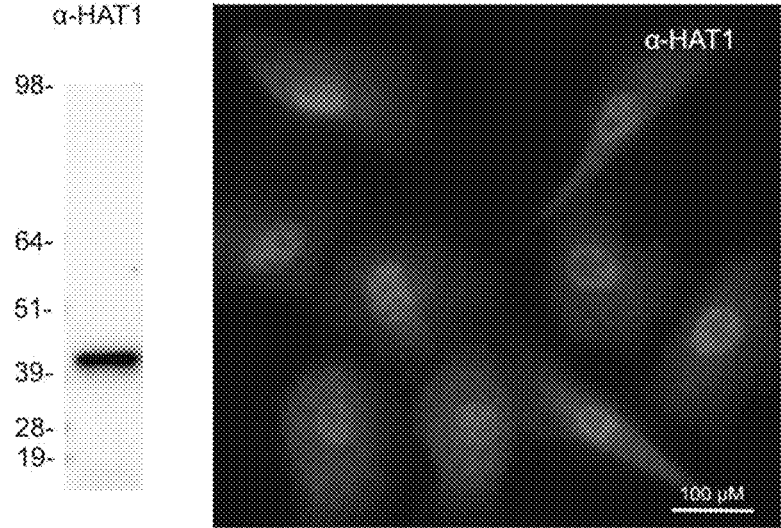
FIG. 15 provides microscopy images of immunostained cells to show expression location of HAT1, utilized in various embodiments.
Figure 16:
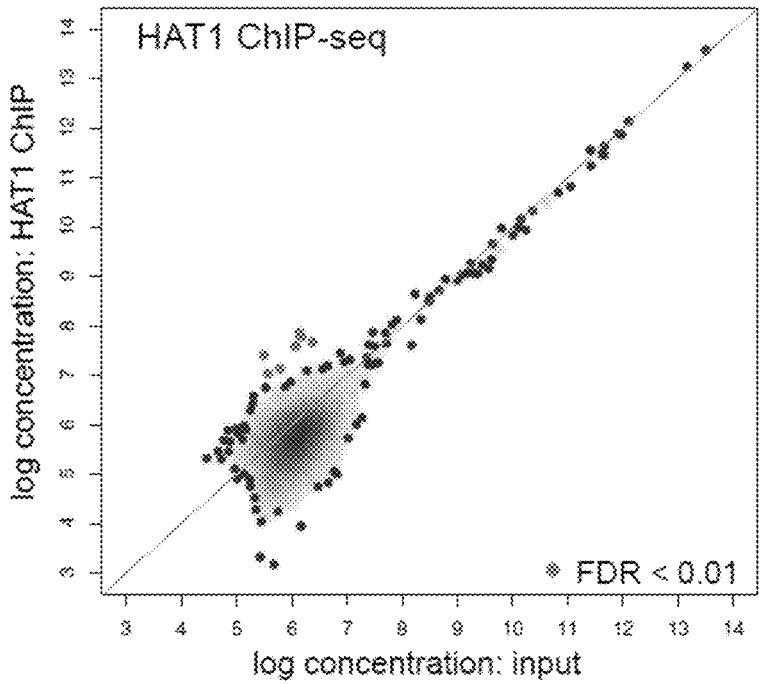
FIG. 16 provides binding ability of a HAT1 antibody of various chromatin compared to input in a ChIP-seq assay, utilized in various embodiments.
Figure 18:
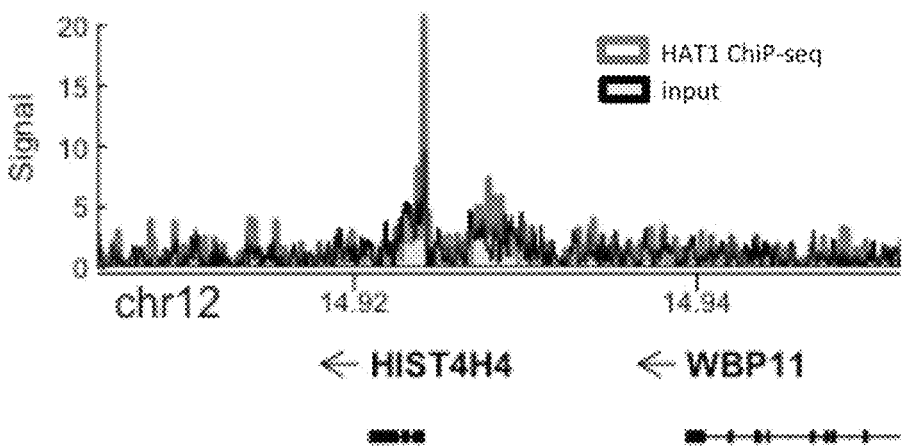
FIG. 18 provides ChIP-seq peaks of HAT1 at the Hist4H4 locus, utilized in various embodiments.
Figure 19:
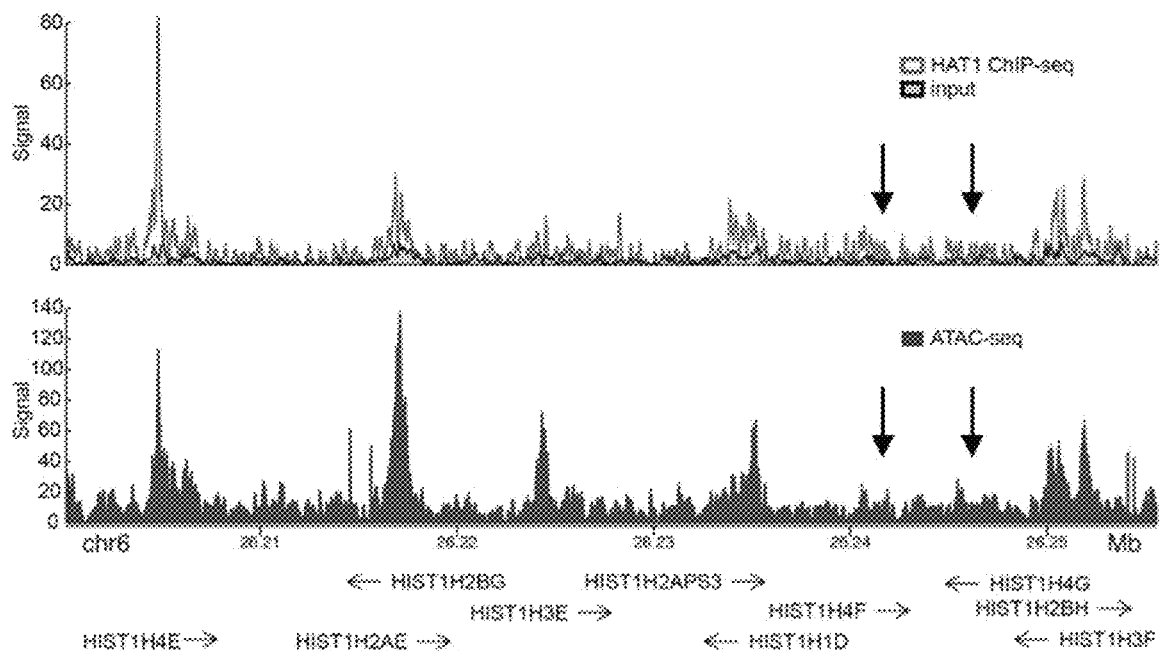
FIG. 19 provides ChIP-seq peaks of HAT1 at the Hist1 locus, utilized in various embodiments.

HAT1 is a cytoplasmic acetyl-transferase of newly synthesized histone H4, which it di-acetylates on lysines 5 and 12 (M. R. Parthun (2013) Biochimica et biophysica acta 1819, 256-263, the disclosure of which is incorporated herein by reference). It is subsequently imported into the nucleus together with the H3/H4 dimer and Rbap46/48 (K. M. Keck and L. F. Pemberton (2012) Biochimica et biophysica acta 1819, 277-289, the disclosure of which is incorporated herein by reference). In hTert-HME1 cells, immunofluorescence using specific antibodies showed strong nuclear localization for HAT1, but cytoplasmic localization was also observed (FIG. 15). HAT1 was assessed for chromatin-binding properties via a chromatin immunoprecipitation followed by high-throughput sequencing (ChIP-seq). Compared to input control, antibodies to HAT1 enriched only seven genomic loci (FIG. 16, B; FDR<0.01). Surprisingly, all of these loci mapped to a one megabase segment of chromosome 6, which is the Hist1 locus that encodes 35 replication-dependent histone genes. Examination of the location of the HAT1 ChIP-seq peaks showed that six were present within 400 bases of histone H4 gene transcription start sites (FIG. 17). One localized downstream of the Hist1H2BC/H2AC locus, consistent with a potential enhancer site. Visual inspection also revealed a HAT1 ChIP-seq signal at the Hist4H4 promoter on chromosome 12, but it did not pass statistical cut-off (FDR>0.05; FIG. 18). There was minimal HAT1 signal at Hist1H4F, Hist1H4G, Hist1H4J or Hist1H4K loci, which were weakly expressed and associated with a closed chromatin state in this cell line (FIG. 19, arrows; and data not shown). In contrast, there was difficulty mapping reads to the Hist2H4A and Hist2H4B loci, preventing assessment of HAT1 recruitment to these loci.

Figure 20:
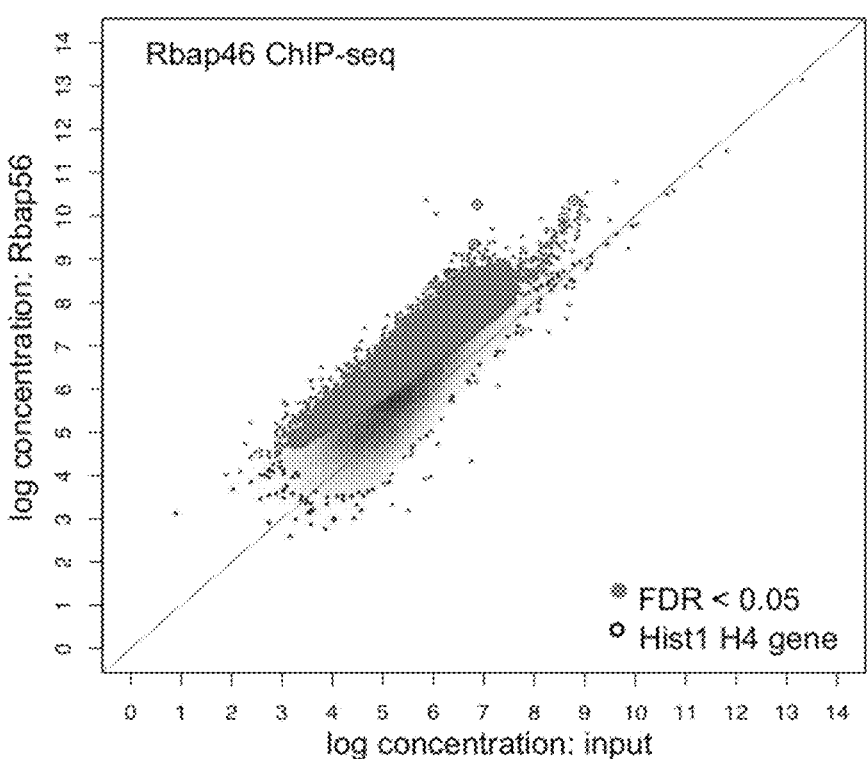
FIG. 20 provides binding ability of a Rbap46 antibody of various chromatin compared to input in a ChIP-seq assay, utilized in various embodiments.

As an independent confirmation that the HAT1 holoenzyme associates with histone H4 promoters, other proteins components of the HAT1 complex were examined. Rbap46 is a bona fide HAT1 interacting protein that also binds newly synthesized histone H4, likely presenting its N-terminus to HAT1 for acetylation. ChIP-seq using antibodies to Rbap46 identified a much broader chromatin binding profile (30475 loci, FDR<0.05; FIG. 20) compared to HAT1 ChIP-seq, consistent with its known roles in other chromatin remodeling complexes including NuRD. However, histone H4 gene promoters were among the most highly enriched loci (FIG. 20) and the Rbap46 ChIP-seq signal at the Hist1 locus overlapped tightly with the HAT1 ChIP-seq signal, showing specific enrichment at the H4 promoters (FIG. 17). Therefore, the HAT1 holoenzyme localizes specifically to histone H4 gene promoters.

Figure 21:
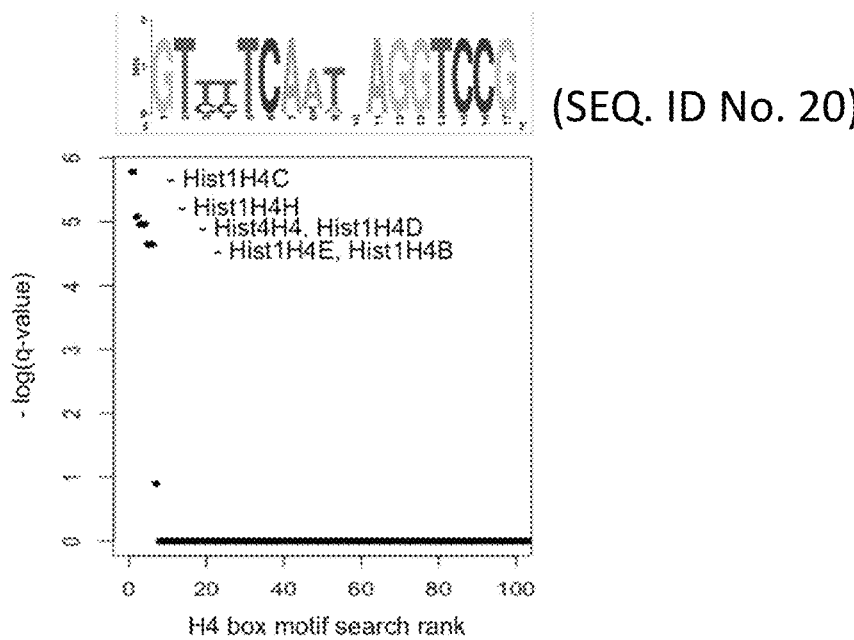
FIG. 21 provides a schematic of the H4-box identified in ChIP-seq results, utilized in various embodiments.

DNA sequences of the H4 promoters were examined to better understand the specific chromatin-binding pattern of the HAT1 holoenzyme complex. Sequence alignments of the H4 promoters identified a highly conserved genetic element of 17 base-pairs in length that is approximately 80 bases upstream of the ATG start codons and contained within the previously described H4 subtype specific consensus sequence that binds the H4 transcription factor Hinfp. This genetic element is referred to throughout as the +14 box' for ease of interpretation. A position weight matrix using the H4 box was used to query for similar motif elements in the accessible DNA elements of the hTert-HME1 cell line derived from ATAC-seq data (FIG. 21). This led to the identification of only H4 gene promoters (FDR<0.01) indicating that this motif is restricted to H4 gene promoters throughout the accessible genome. Luciferase assays were used to confirm that the H4 box was critical for transactivation of the H4 promoter. Whereas the wild-type Hist1H4E promoter produced robust Firefly luciferase activity, complete or partial deletions of the H4-box strongly diminished this activity (FIG. 22) when normalized to co-transfection of a control *Renilla* luciferase construct. Therefore, histone H4 promoters have a functional, unique DNA promoter element that may underlie the specific recruitment of HAT1 complexes to these loci.

HAT1 is Critical for Maintaining Levels of Newly-Synthesized H4

Figure 22:
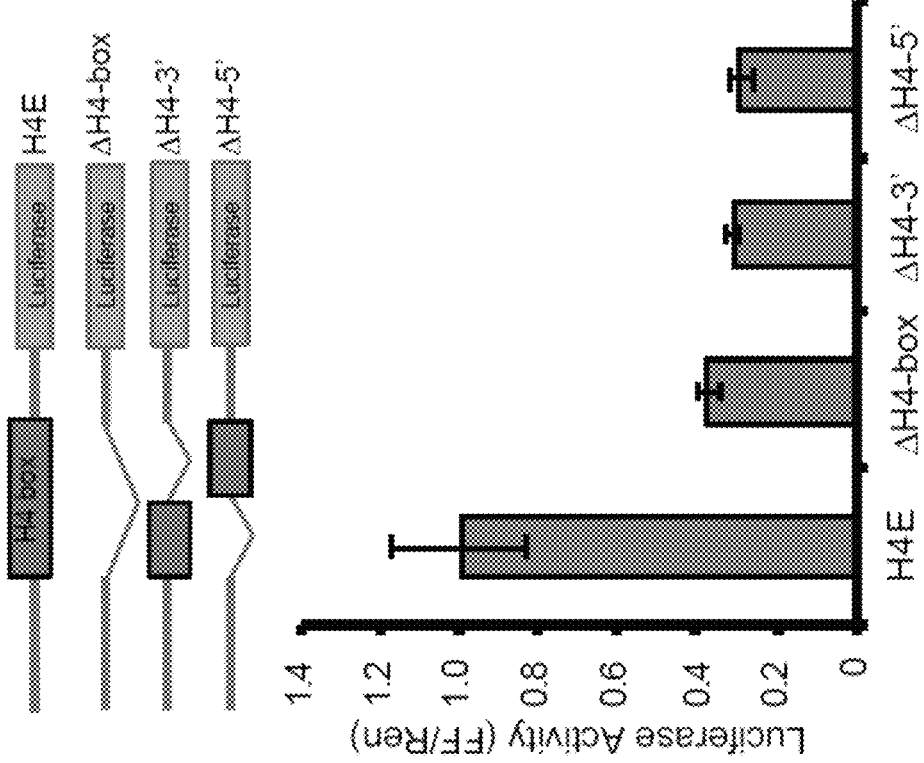
FIG. 22 provides luciferase expression results of the H4E promoter with and without the H4-box, utilized in various embodiments.
Figure 23:
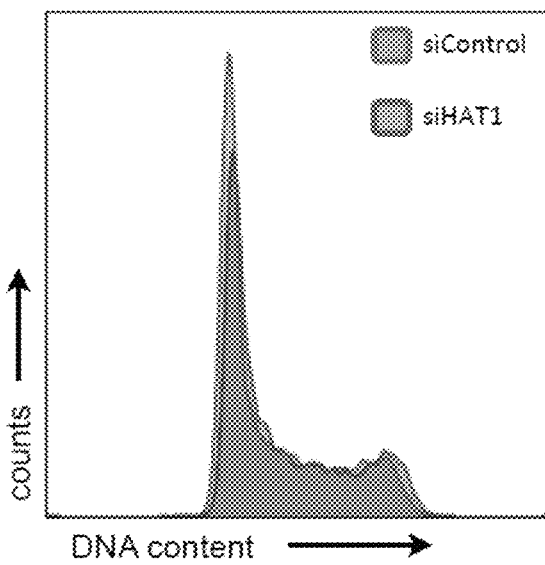
FIG. 23 provides a data graph on cell cycle analysis of 293T cells transfected with siRNAs for HAT1, utilized in various embodiments.

Given that the HAT1 holoenzyme complex was specifically recruited to H4 promoters, the possibility of HAT1 directly regulating H4 gene transcription was tested. Short-interfering RNAs (siRNAs) were used to deplete HAT1 protein levels from 293T cells followed by transfection of luciferase reporters. Luciferase reporters bearing the Hist1H4E wild-type reporter were sensitive to HAT1 depletion, but deletion of the H4-box diminished sensitivity to HAT1 levels (FIG. 22). Cell cycle analysis was performed to determine if this decrease in transcription activity was due to aberrant S phase progression. In cells depleted of HAT1 there was a modest accumulation of cells in G1 phase (5.2% increase) compared to control (FIG. 23). This small change in cell cycle profile could not account for the 40% decrease in luciferase activity seen. These data indicate that HAT1 binding to Hist1H4E promoters may have a specific stimulatory effect on H4 gene transcription.

Figure 24:
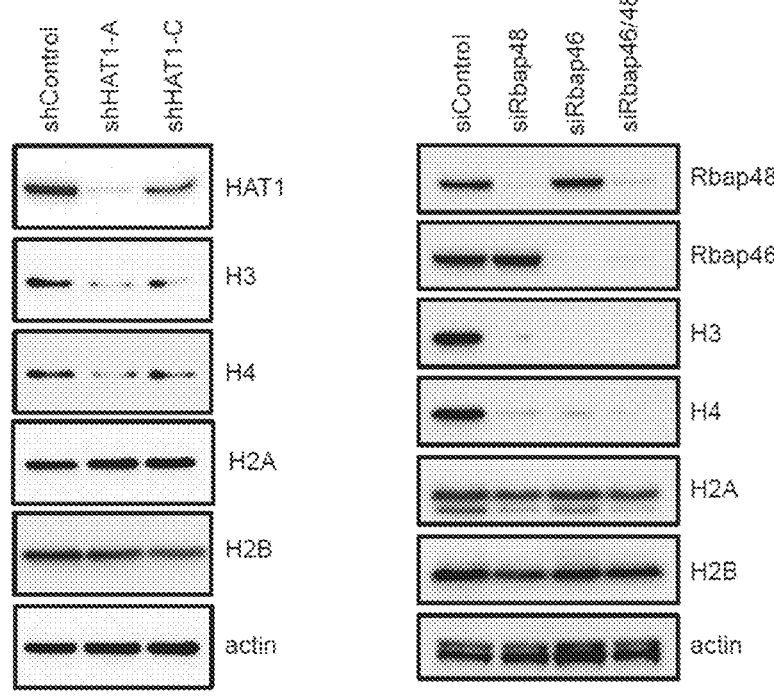
FIG. 24 provides immunoblots of hTert-HME1 cells transduced with shRNAs for HAT1, utilized in various embodiments.
Figure 25:
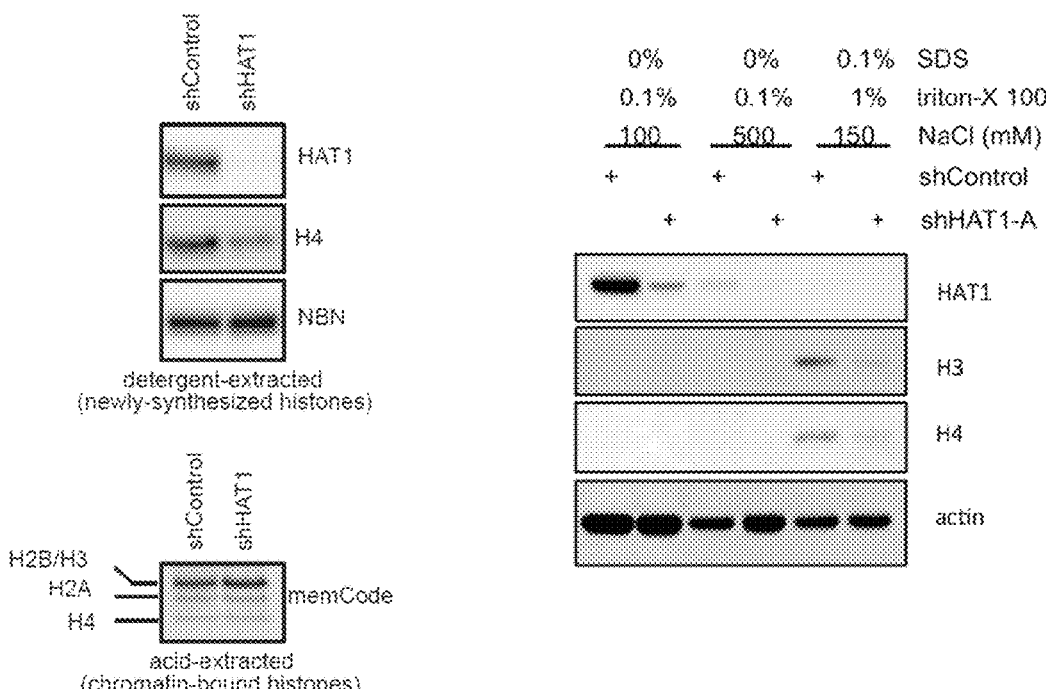
FIG. 25 provides immunoblots of newly synthesized and chromatin-bound histones from hTert-HME1 cells transduced with shRNAs for HAT1, utilized in various embodiments.

Acute infection of hTert-HME1 cells with lentiviral shRNAs targeting HAT1 led to substantial depletion of newly synthesized histone H3 and H4 levels, compared to control shRNAs, with no effect on H2A and H2B levels (FIG. 24), consistent with coordinated post-translation regulation of H3/H4 dimers (A. J. Cook, et al., (2011) Molecular cell 44, 918-927, the disclosure of which is incorporated herein by reference). This effect was also true for the HAT1 holoenzyme as siRNAs targeting Rbap46 or Rbap48 both caused decreased H3/H4 dimers without a significant change in H2A or H2B levels, compared to control siRNA (FIG. 24). Newly synthesized H3/H4 dimers, rather than nucleosomal H3/H4, appeared to be affected as determined by detergent and acid histone extraction, respectively (FIG. 25). Additional experiments confirmed these newly synthesized histones were highly sensitive to detergent extraction, as compared to salt extraction (FIG. 25). Thus, HAT1 promotes accumulation of newly synthesized histone H3/H4 dimers without affecting levels of histones embedded in nucleosomes, which could be attributed to a defect in H4 synthesis or the ability of nascent H3/H4 dimers to bind with histone chaperones.

HAT1 is Required for S Phase Entry and Progression

Figure 26:
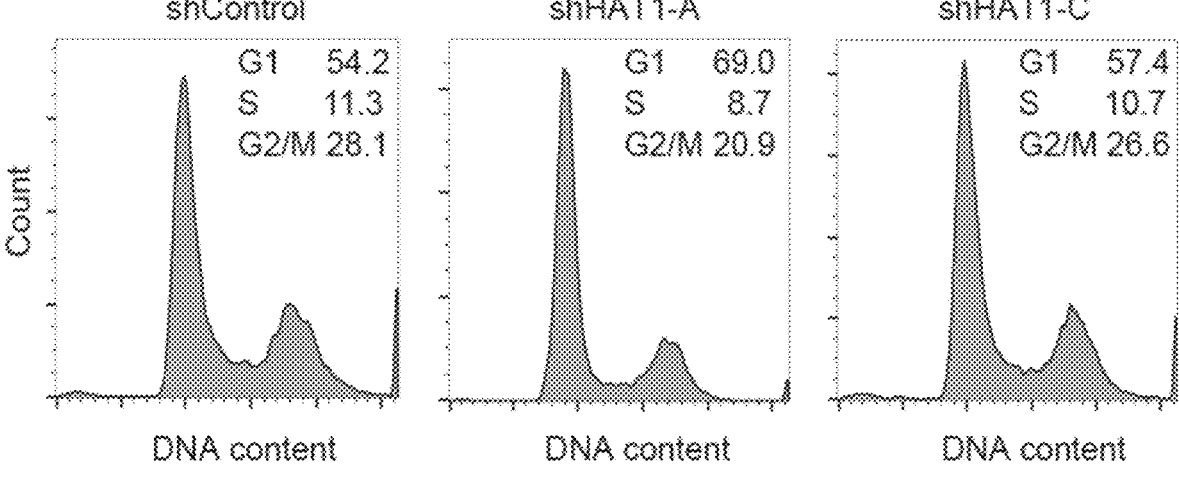
FIGS. 26 and 27 provide a data graphs on cell cycle analysis of hTert-HME1 cells transduced with shRNAs for HAT1, utilized in various embodiments.

Because the transcription of H4 genes is tightly coupled to S-phase, cell cycle analysis was performed after depletion of HAT1 with shRNAs in hTert-HME1 cells. A gene-dosage effect was identified whereby strong depletion of HAT1 (shHAT1-A; FIG. 24) caused a strong block to S-phase entry with accumulation of cells in G1 (FIG. 26), whereas a less robust depletion (shHAT1-C) caused more modest differences in the cell cycle profile, compared to control-treated cells. Therefore, HAT1 depletion caused both hTert-HME1 cells and 293T cells to accumulate in G1 phase, but the effect was more pronounced in hTert-HME1.

Figure 27:
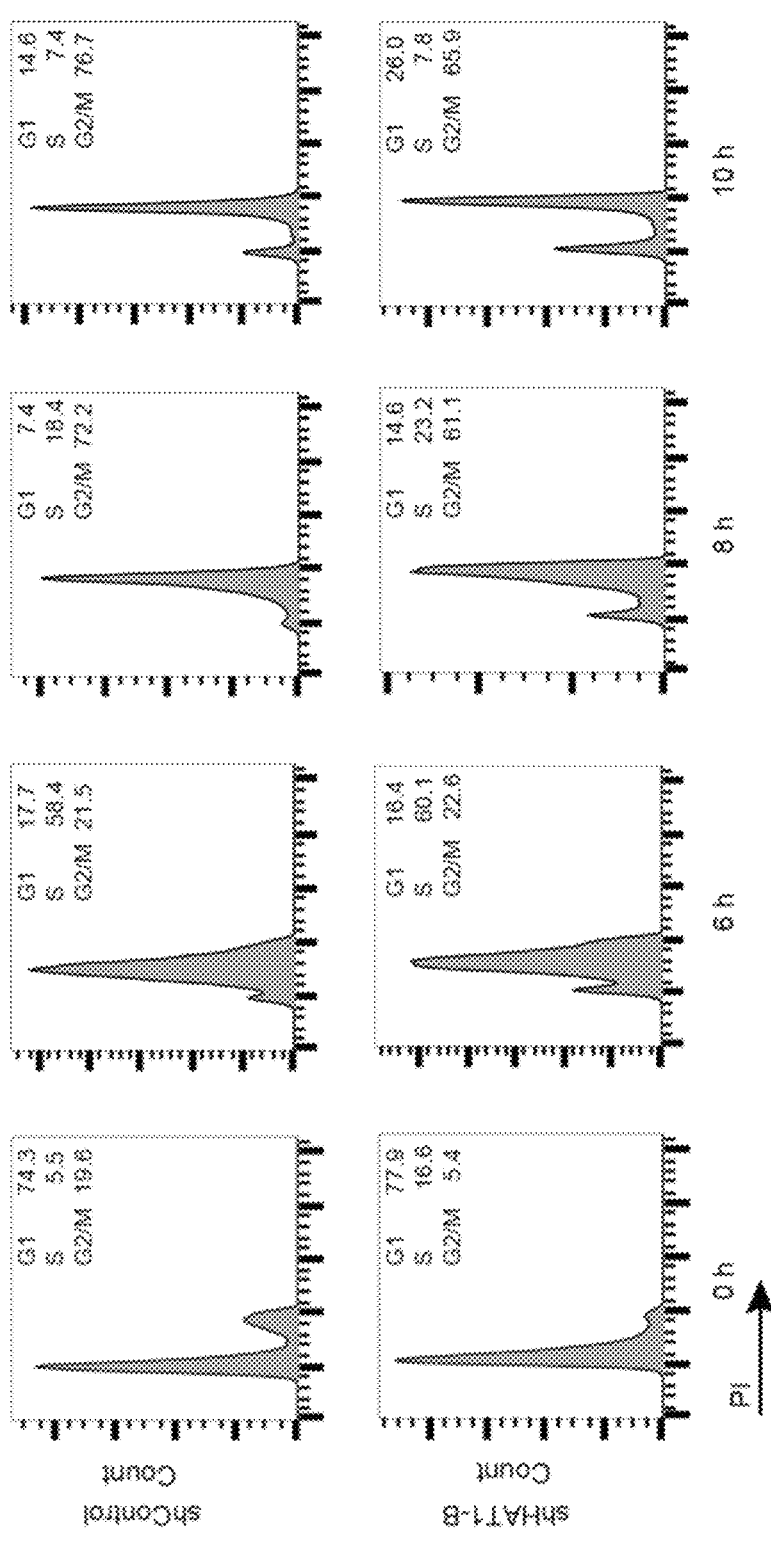
Figure 28:
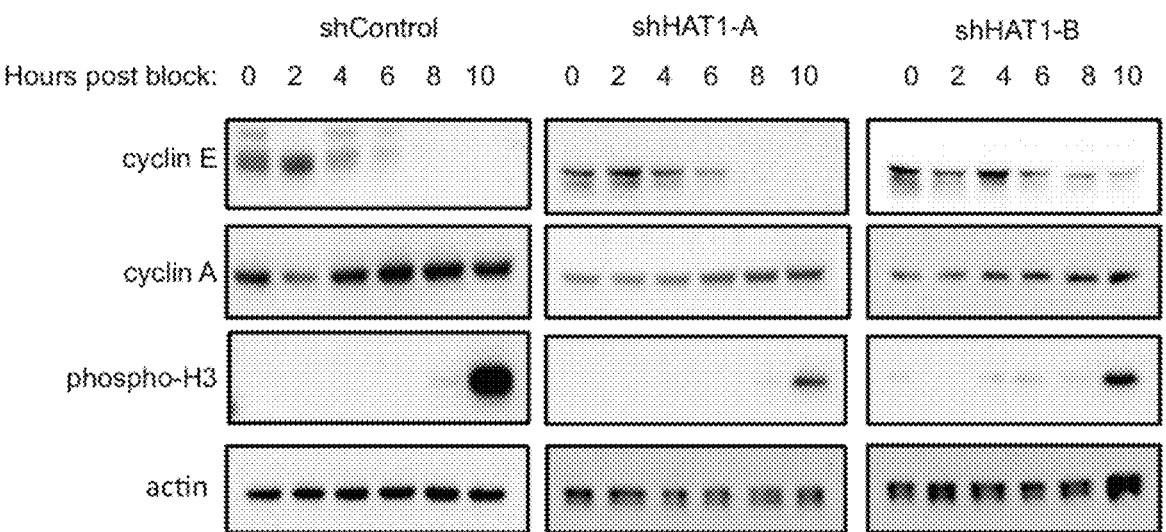
FIG. 28 provides immunoblots of cell cycle proteins in hTert-HME1 cells transduced with shRNAs for HAT1, utilized in various embodiments.

Replication-dependent histones are strongly induced during S-phase to support chromatin replication. To more precisely define the role of HAT1 in S-phase progression, double thymidine block was performed to arrest cells at the G1/S transition. After release from double-thymidine block cell cycle status was monitored by flow cytometry and immunoblots for cyclin A, E and phospho-histone H3, markers of G1, S and M phase, respectively (FIGS. 27 and 28). A similar percentage of control and HAT1-depleted cells arrested at the G1/S transition by double-thymidine block. However, the number of cells remaining in S-phase at 8 hours after release from block was increased in the HAT1-depleted cells compared to control (23.2% HAT1-depleted versus 18.4% control), consistent with delayed S-phase progression. Also, a greater percentage remained in G1 at 8 and 10 hours after release from the block, compared to control cells. Therefore, HAT1-depleted cells have less propensity to enter S phase or proceed more slowly through S phase compared to control cells.

Figure 29:
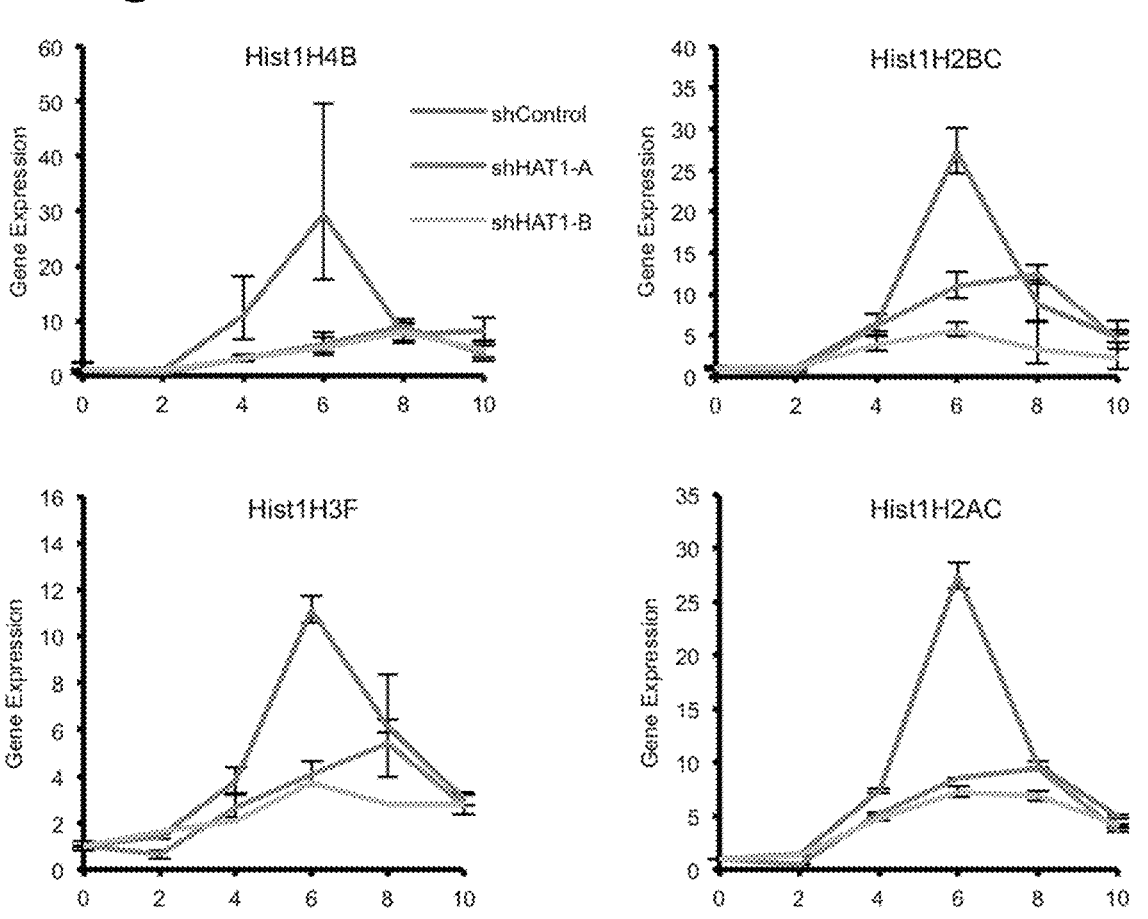
FIG. 29 provides expression levels of histone gene transcripts in hTert-HME1 cells transduced with shRNAs for HAT1, utilized in various embodiments.

A similar double-thymidine block and release was used to examine histone mRNA transcript levels during S-phase progression. Consistent with the block in S-phase progression observed, levels of all tested replication-dependent histone transcripts were diminished in HAT1-depleted cells (FIG. 29). This likely reflects coordinated post-transcriptional effects mediated by common 3' ends shared by all replication-dependent histone mRNAs.

HAT1-Stimulated Acetyl Groups Drive Transcription Via a H4 Promoter Element

Figure 31:
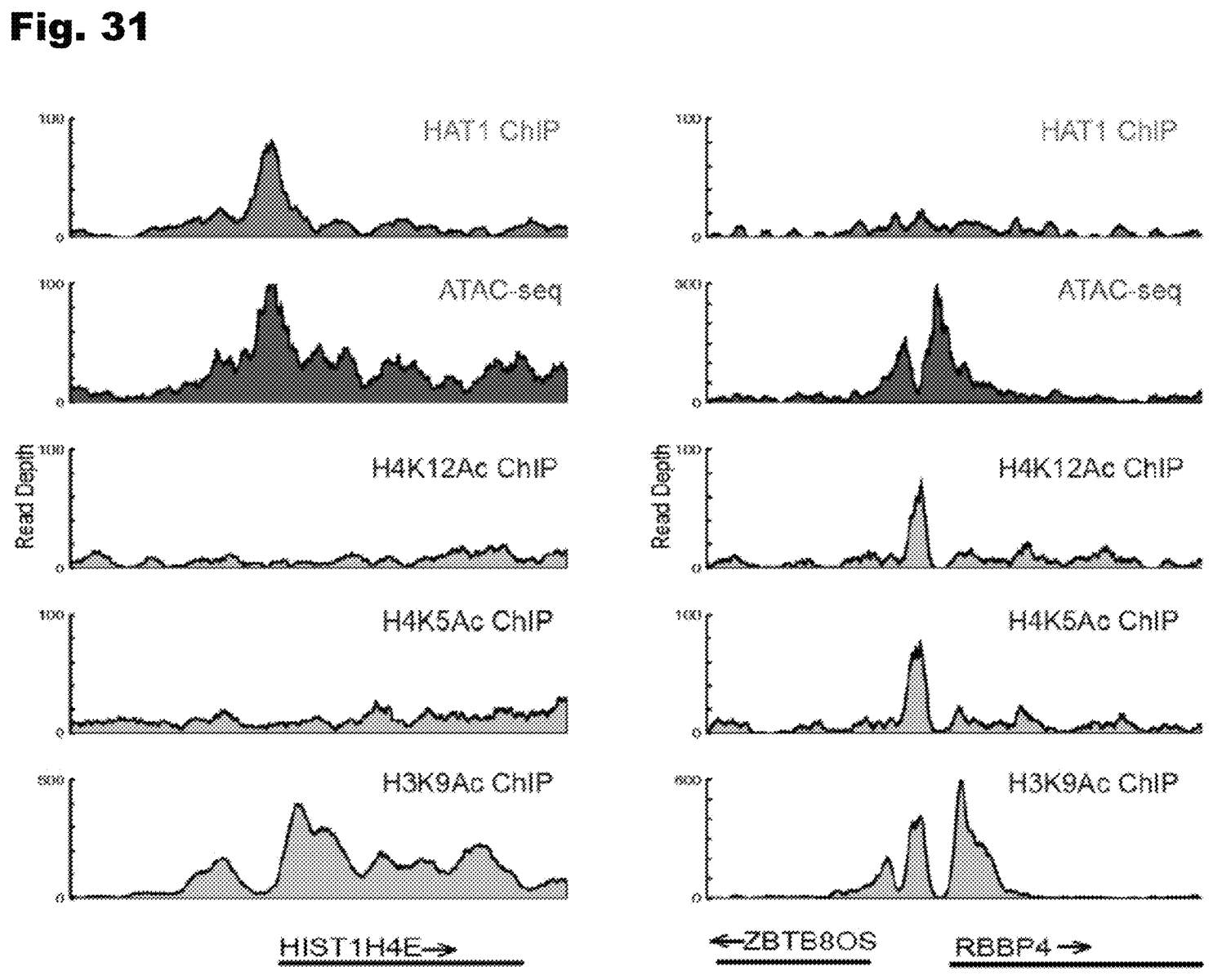

To better understand how HAT1 affects transcription of histone genes, the chromatin state of the Hist1 locus was examined by mapping of the HAT1-dependent histone acetylation sites (H4 lysines 5 and 12) by ChIP-seq in six cell lines (3 shControl and 3 shHAT1 treated; FIG. 30). ChIP-seq for the HAT1-dependent H4K12Ac and H4K5Ac marks identified 2590+/−3163 and 14012+/−9599 (mean+/−SD; FDR<0.01) peaks, respectively. However, there was no significant alteration in genome-wide H4K12Ac or H4K5Ac ChIP-seq signal between control and HAT1-depleted cell lines (FIG. 30). This was confirmed by immunoblots, which showed maintained H4K5 and H4K12 acetylation on nucleosomal histones after acid extraction, despite loss of H4K5 and H4K12 acetylation on newly synthesized H4 caused by HAT1 depletion (FIG. 30). This is consistent with the reported high acetyltransferase activity of HAT1 towards free H3/H4 dimers, but lack of acetyltransferase activity for nucleosomal H4 M. R. Parthun, J. Widom, and D. E. Gottschling, (1996) Cell 87, 85-94, the disclosure of which is incorporated herein by reference). Furthermore, there was no enrichment for H4K12Ac or H4K5Ac ChIP-seq signal at histone H4 promoters, despite identification of these marks at promoters elsewhere in the genome (representative examples of the Hist1H4E and ZBTB8OS/RBBP4 loci are shown in FIG. 31). Therefore, it is unlikely that HAT1-induced acetylation of nucleosomal H4 at H4 promoters affects transcription from these promoters, however HAT1 may have other acetylation targets.

As the HAT1-dependent histone modifications were not detected at the H4 promoters, it was next tested if the acetyltransferase activity was important for cell proliferation. The HAT1-depleted cell lines were rescued with cDNAs encoding either wild-type HAT1 or HAT1 with an E276Q mutation that has been shown to impair acetyltransferase function H. Wu, et al., (2012) Proceedings of the National Academy of Sciences of the United States of America 109, 8925-8930, the disclosure of which is incorporated herein by reference). The HAT1 cDNAs carried silent mutations to disrupt the shRNA target site to allow expression after depletion of endogenous HAT1. Whereas wild-type HAT1 rescued proliferation of HAT1-depleted cells, the HAT1-E276Q mutant did not (FIG. 32). This confirmed that the catalytic activity of HAT1 is critical to its role in proliferation.

Because the acetyltransferase function of HAT1 was required to support proliferation it was tested whether exogenous acetate, the product of histone de-acetylation, could rescue histone H4 levels. Cells treated with control or HAT1-targeted shRNAs were cultured in the presence or absence of 5 mM sodium acetate. Exogenous acetate supplementation rescued histone H4 protein levels after HAT1 depletion and also increased H4 protein in control cells (FIG. 33). Thus, although nucleosomal H4K5Ac and H4K12Ac are not associated with H4 promoters, free acetate is sufficient to boost H4 levels in the absence of HAT1. Acetate did not rescue acetylation of the HAT1-dependent histone marks H4 lysine 5 or 12 (FIG. 33) indicating that acetate functioned downstream of HAT1 catalytic activity. Also, acetate supplementation was not sufficient to rescue proliferation or S-phase progression in the absence of HAT1 (data not shown). Therefore, HAT1 may contribute other essential functions for cell division beyond H4 stimulation. Taken together, these results suggest that acetate is likely regenerated to acetyl-Co-A and utilized to stimulate increased H4 protein levels, a process to which HAT1 may contribute through promoter binding.

Figure 34:
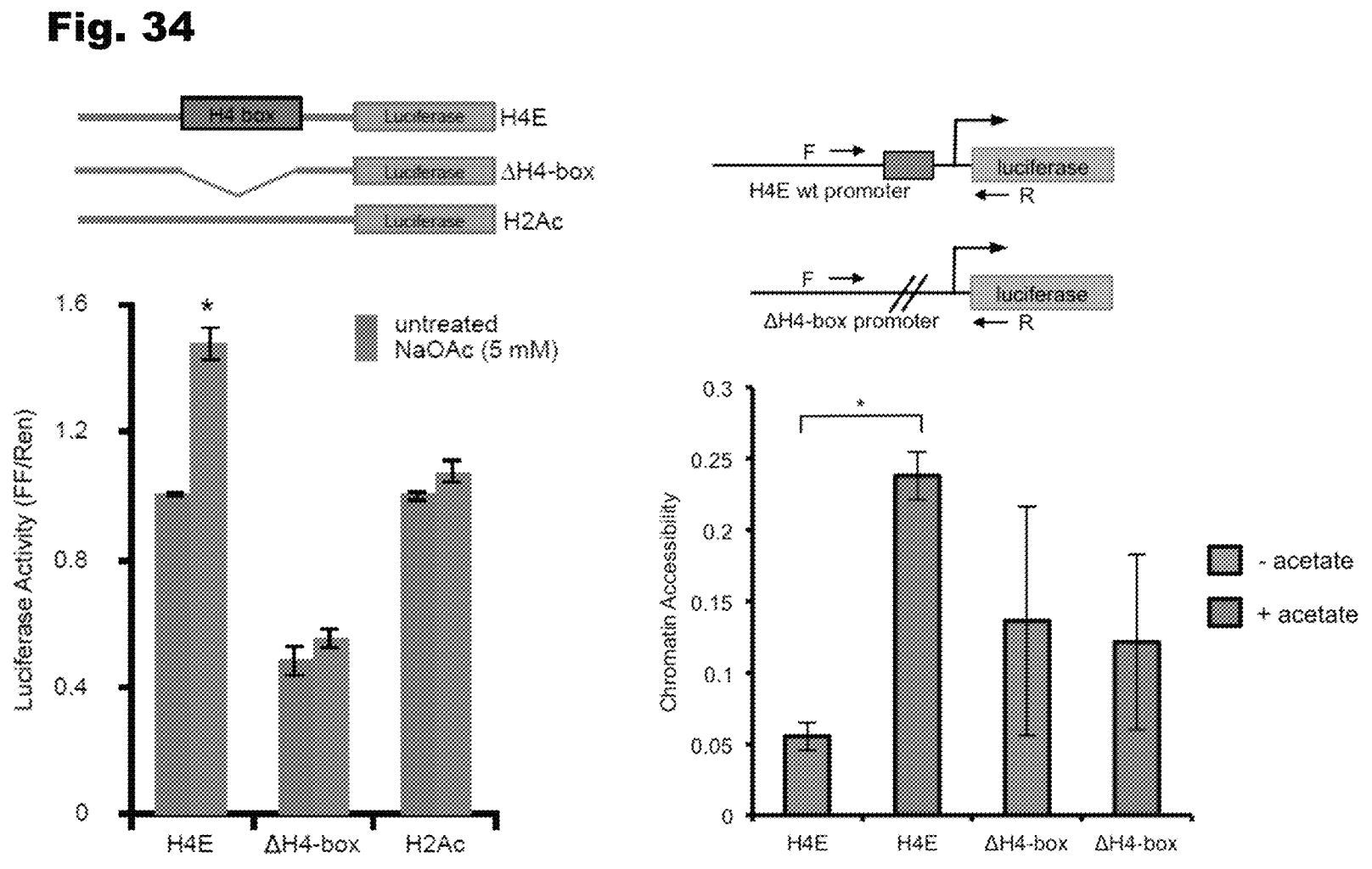

The Hist1H4E promoter fused upstream of firefly luciferase led to robust induction of luciferase activity when transfected to 293T cells, an effect that was further stimulated by treatment with exogenous sodium acetate (FIG. 34). In contrast, when the H4-box was deleted from the Hist1H4E promoter (ΔH-box), there was diminished luciferase activity compared to the wild-type promoter and it was no longer responsive to acetate supplementation (FIG. 34). As a control, the Hist1H2Ac promoter, which does not contain an H4-box, was not acetate sensitive. Further analysis of chromatin accessibility at the reporter showed that the H4-box conferred increased chromatin accessibility after acetate treatment (FIG. 34), an effect that was not evident if the H4-box was deleted. Therefore, histone H4 promoters are acetate sensitive and this property requires the H4-box.

Figures 35, 36:
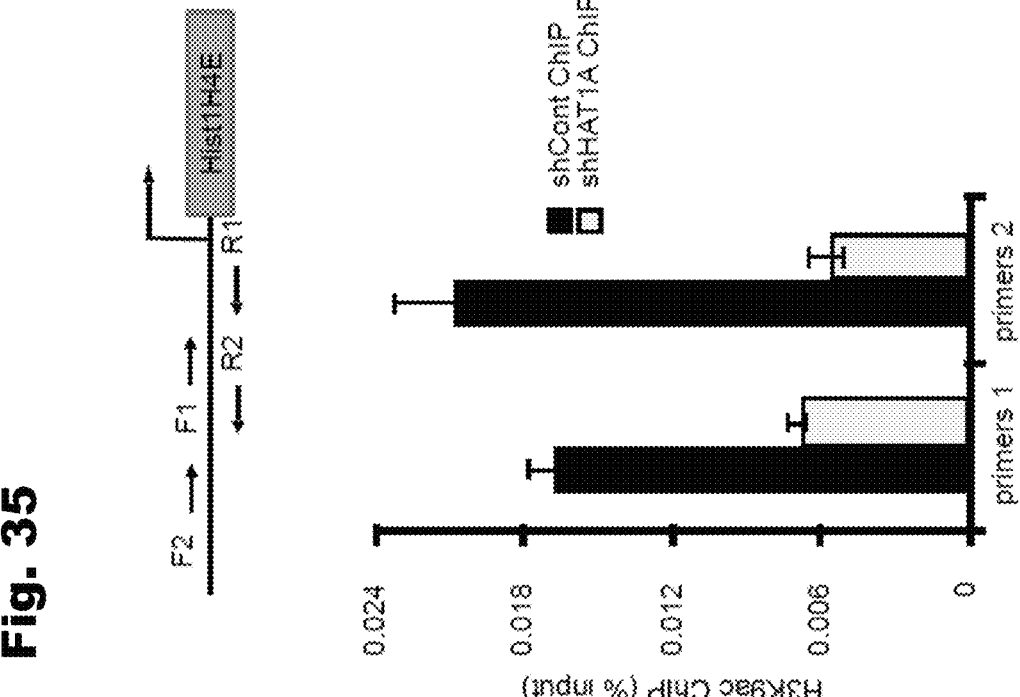
FIG. 35 provides data graphs of ChIP-qPCR of the HIST1H4E promoter utilizing antibodies to H3K9Ac in hTert-HME1 cells transduced with shRNAs for HAT1, utilized in various embodiments.
FIG. 36 provides binding ability of a H3K9ac antibody of various chromatin compared to input in a ChIP-seq assay in hTert-HME1 cells transduced with shRNAs for HAT1, utilized in various embodiments.

Acetate supplementation has previously been described to stimulate acetylation of lysine residues on histone H3. This motivated an assessment for changes in histone H3 lysine acetylation at histone H4 promoters. ChIP-qPCR identified that depletion of HAT1 led to a loss of H3 lysine 9 acetylation at the endogenous promoter of the Hist1H4E gene (FIG. 35). This suggests that HAT1 stimulates histone H3 lysine 9 acetylation at H4 promoters, an effect that may stimulate increased chromatin accessibility.

HAT1 is Required for Locus-Specific Histone H3 Acetylation

The identification of a defect in histone H3 lysine 9 acetylation at the Hist1H4E promoter motivated a more careful study of global histone acetylation after HAT1 depletion. ChIP-seq was performed for H3 lysine 9 acetylation in the six cell lines with stable HAT1 depletion and controls (FIG. 30). This led to identification of 793 sites (FDR<0.05) with decreased histone H3 lysine 9 acetylation in cell lines with stable HAT1 depletion compared to control cells (FIG. 36). This indicates that HAT1 is required to maintain H3 lysine 9 acetylation levels at an array of genomic sites.

Figure 37:
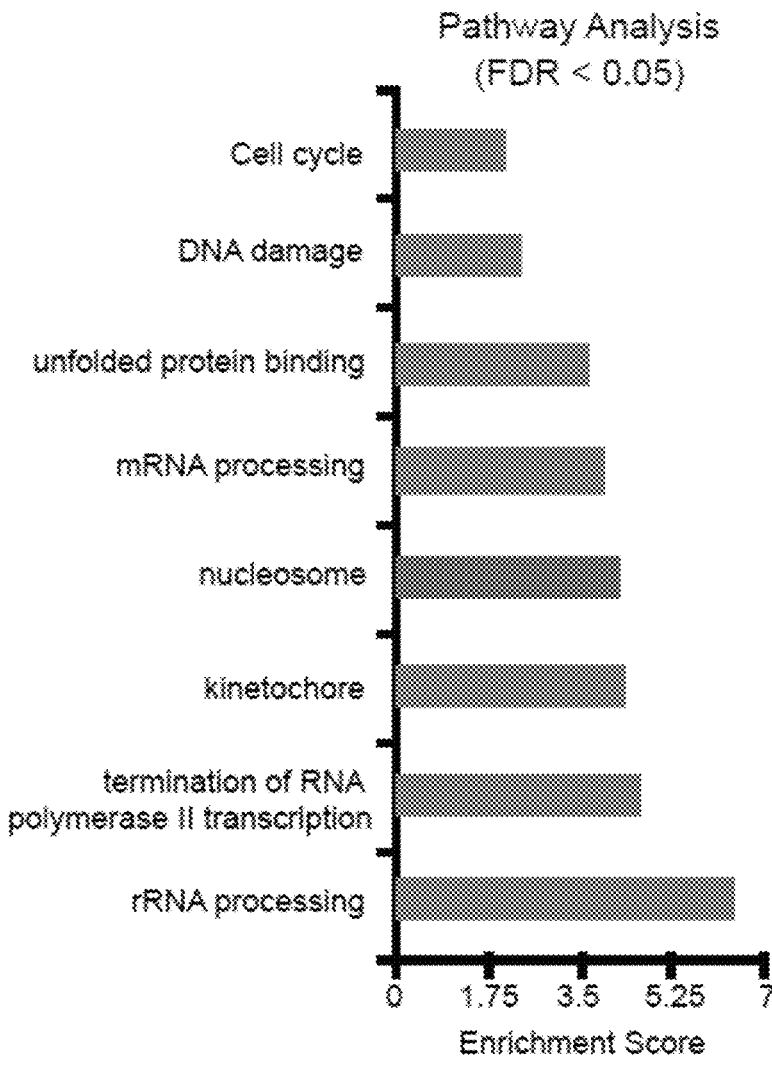
FIG. 37 provides path analysis of genes linked to altered H3K9 acetylation in hTert-HME1 cells transduced with shRNAs for HAT1, utilized in various embodiments.
Figure 38:
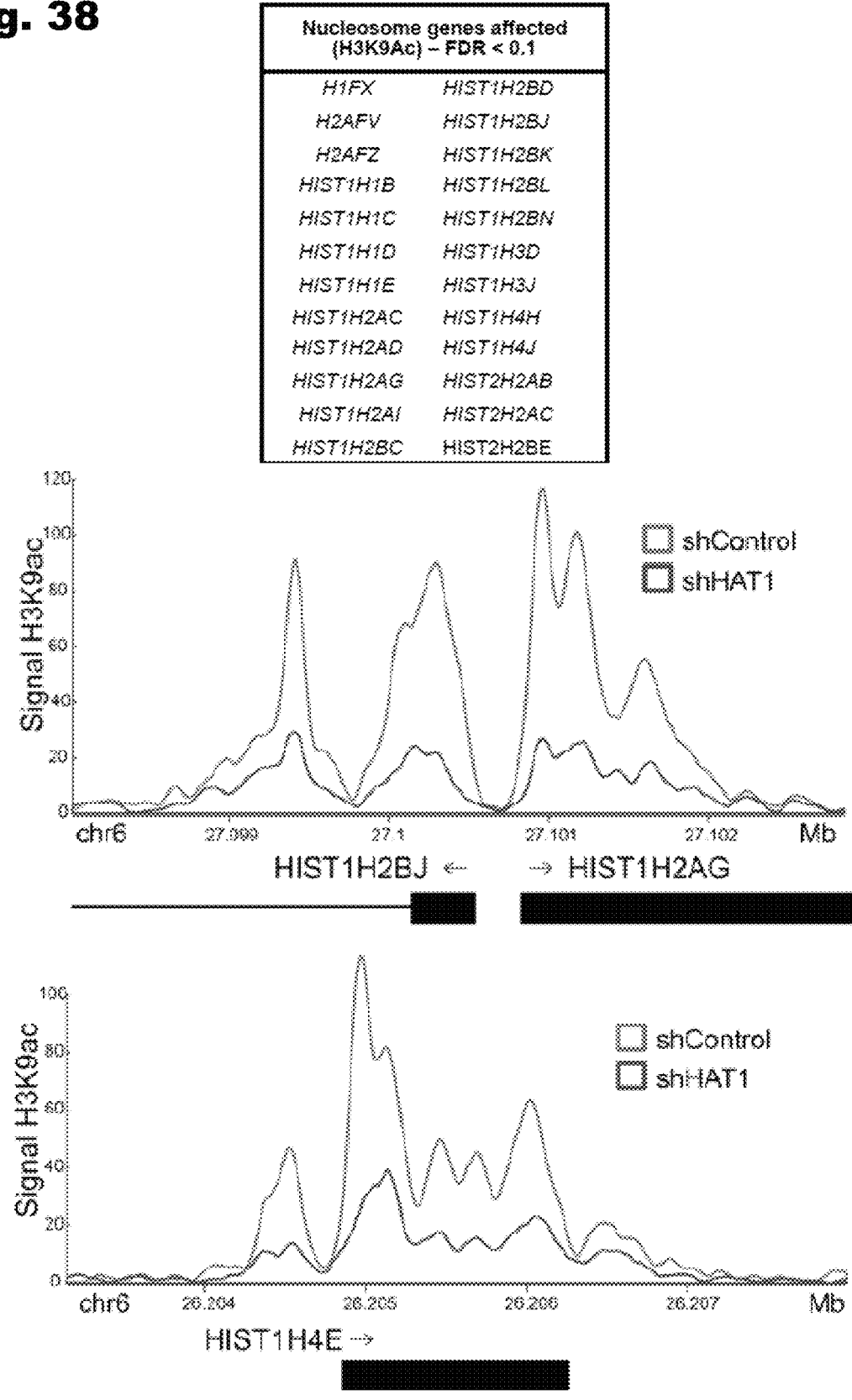
FIG. 38 provides nucleosome genes affected by altered H3K9 acetylation in hTert-HME1 cells transduced with shRNAs for HAT1, utilized in various embodiments.

Next, pathway analysis was performed on the genes that had a H3 lysine 9 acetylation defect. This revealed a number of pathways associated with cell proliferation including cell cycle, DNA damage, RNA processing, nucleosome and kinetochore (FIG. 37), suggesting that this acetylation defect could contribute to delayed growth and S phase progression in HAT1-depleted cells. Further examination of the genes in the 'nucleosome' pathway showed that many replication-dependent histone genes were affected including H4 genes, as well as genes for H1, H2A, H2B and H3 (FIG. 38). Therefore, multiple genes contributing to cell proliferation have diminished H3 lysine 9 acetylation after HAT1 depletion.

Figure 39:
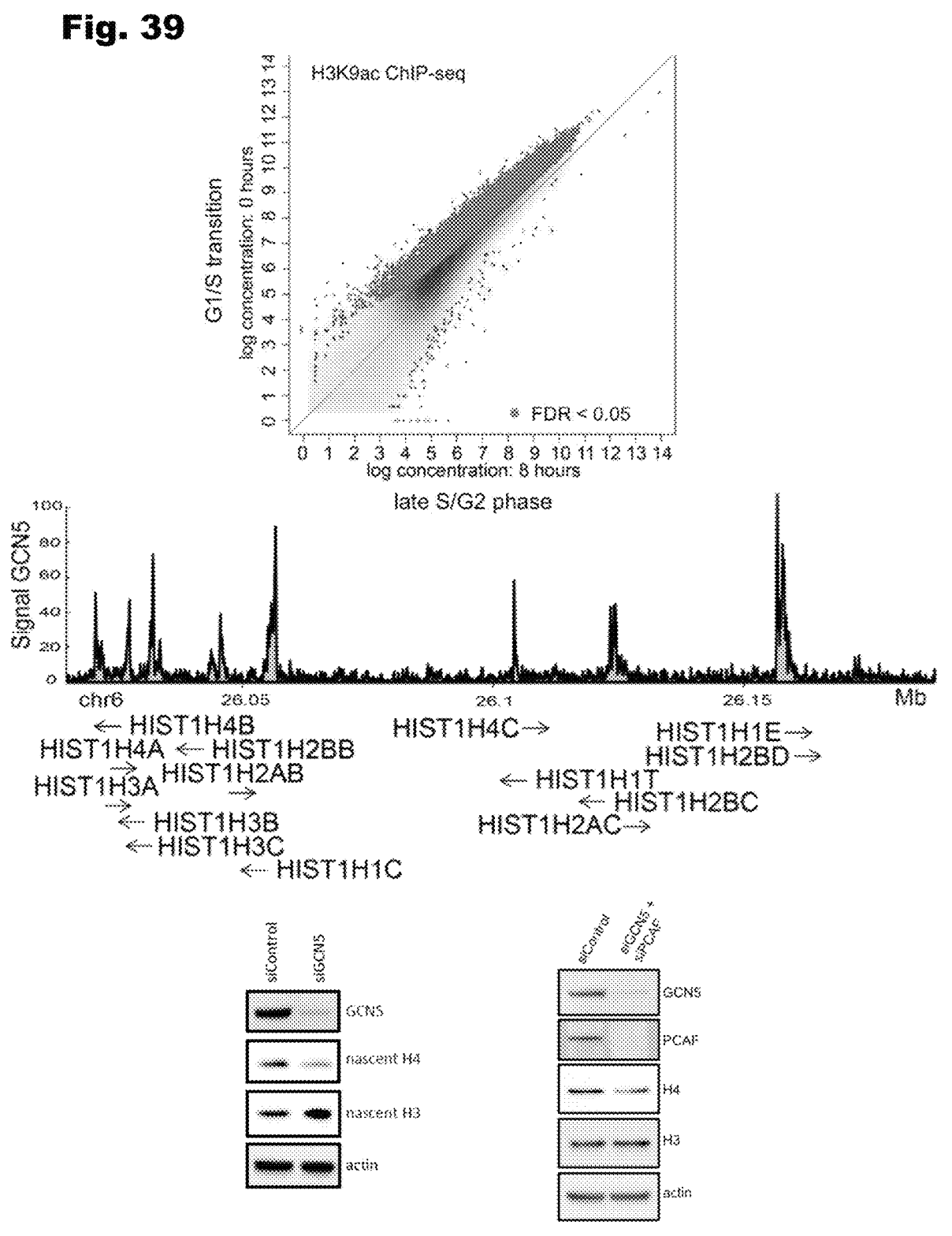

Next, to determine whether the H3 lysine 9 acetylation defect in HAT1-depleted cell lines was a primary defect or secondary to aberrant cell cycle progression, global H3 lysine 9 acetylation ChIP-seq were compared profiles between hTert-HME1 cells synchronized at the G1/S transition (early S phase) with cells synchronized in late S/G2. Overall, there were 24,937 differential H3 lysine 9 loci identified (FDR<0.05; FIG. 39), of which the vast majority (24,827) had increased signal at the G1/S transition (early S) compared to late-S/G2 phase. This is consistent with previous studies showing that histone H3 lysine 9 acetylation builds during G1 phase and diminishes during and after S-phase. Therefore, the observed HAT1-dependent decrease in H3 lysine 9 acetylation is unlikely to be secondary to a decrease proportion of HAT1-depleted cells in G2/M phase compared to control cells, but these data do not exclude a role for HAT1 in promoting G1/S transition, which could also lead to H3 lysine 9 acetylation.

As HAT1 does not acetylate H3 lysine 9 nor does it bind to the vast majority of genomic sites with diminished H3 lysine 9 acetylation it was hypothesized that a dedicated H3 lysine 9 acetyltransferase may be responsible for H3 lysine 9 acetylation downstream of HAT1 activity. Examination of published ENCODE ChIP-seq data for H3 lysine 9 acetyltransferases showed that GCN5/KAT2A had extensive binding throughout the Hist1 locus (FIG. 39). Therefore, HAT1- mediated acetylation of nascent histones may feed acetyl groups to GCN5 via de-acetylation of deposited nascent histones and regeneration of acetyl-Co-A by ACSS2. Indeed, depletion of GCN5/KAT2A led to reduction of nascent histone H4 levels, compared to control siRNA treatment (FIG. 39), confirming that other histone acetyltransferases may work downstream of HAT1 to promote gene expression. A similar effect was seen when pools of siRNAs were used to deplete both GCN5 and the related acetyltransferase PCAF/KAT2B (FIG. 39). GCN5 depletion did not cause diminished nascent H3 protein levels (FIG. 39), indicating the H4 genes may be more sensitive to H3 lysine 9 acetylation status compared to other genes.

Elevated HAT1 Levels are Associated with Poor Outcomes in Malignancies

Figure 40:
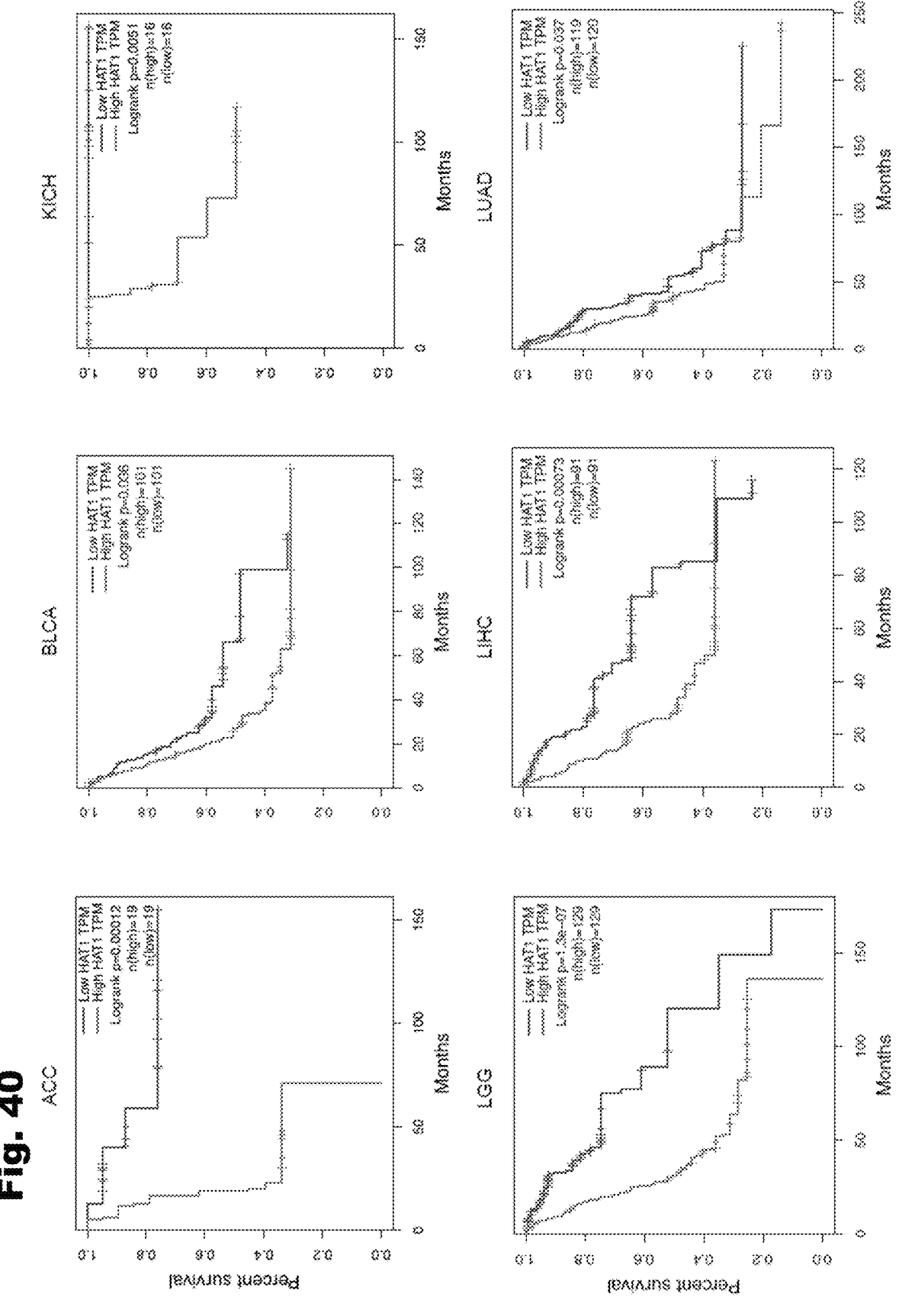
FIG. 40 provides Kaplan-Meier survival plots of various cancers stratified by HAT1 expression levels, utilized in various embodiments.

The above data indicate that HAT1 is a positive regulator of EGF-dependent proliferation through its ability to stimulate histone acetylation and S-phase progression. Furthermore, growth factor signaling pathways are common driver mutations in human malignancy. This led to the hypothesis that HAT1 expression could be an important dependency of cell proliferation in human cancers. To determine whether HAT1 expression is associated with human cancer outcomes, overall survival was stratified by HAT1 expression levels in all tumor subsets in the available TCGA data. This led to the identification of six solid tumor subtypes (ACC, BLCA, KICH, LGG, LIHC, LUAD) wherein high HAT1 levels (upper quartile of expression) were significantly associated with inferior survival outcomes, compared to the low HAT1 expressing tumors (lowest quartile of expression; FIG. 40). Therefore, HAT1 expression level may be an important predictor of patient outcomes in various human malignancies.

Figure 41:
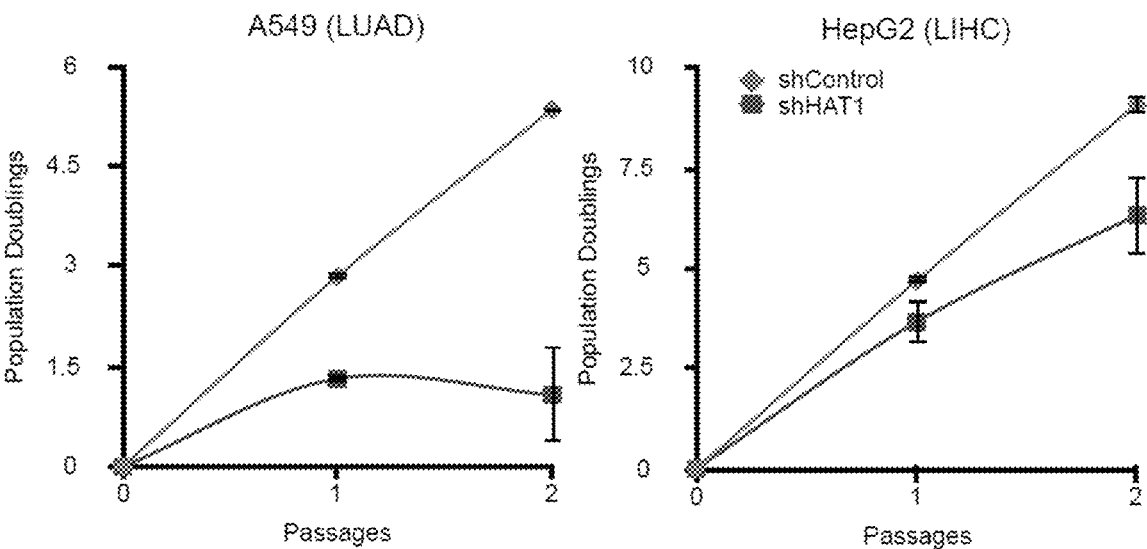
FIG. 41 provides growth curves of two cancer cell lines transduced with shRNAs for HAT1, utilized in various embodiments.
Figure 42:
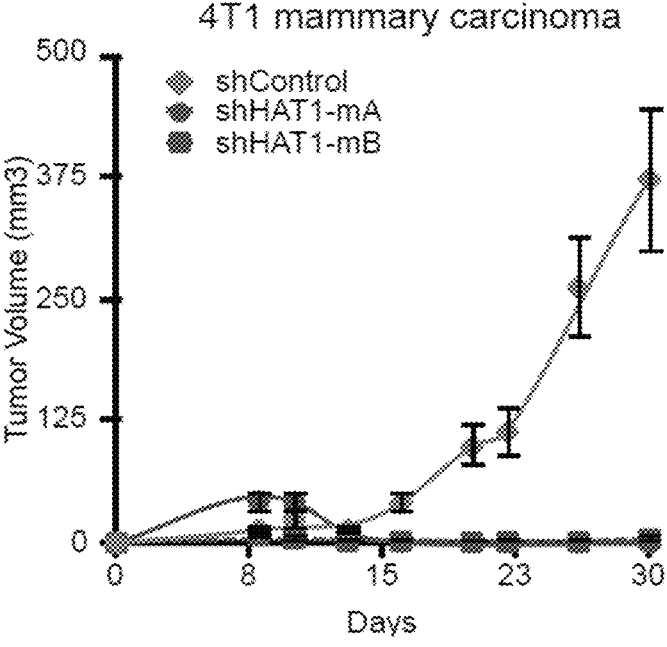
FIG. 42 provides growth curves of 4T1 mammary carcinoma tumors transduced with shRNAs for HAT1 and grafted into bilateral mammary fat pads of mice, utilized in various embodiments.

To confirm that HAT1 expression is important for human cancer cell proliferation, cell lines derived from LUAD and LIHC tumor types were treated control or HAT1 shRNAs. Depletion of HAT1 was associated with diminished proliferation in both A549 (LUAD) and HepG2 (LIHC) cancer cell lines (FIG. 41). This suggests that HAT1 expression may be critical to support cancer cell proliferation in these cancer subtypes. In addition, HAT1 depletion impaired tumor formation in vivo as mice orthotopically injected with 4T1 mammary carcinoma cell lines with two independent shRNAs targeting HAT1 failed to form tumors, whereas the control shRNA-expressing 4T1 cells formed tumors robustly (FIG. 42). Therefore, HAT1 expression engenders cancer cell proliferation and tumor formation.

Figure 43:
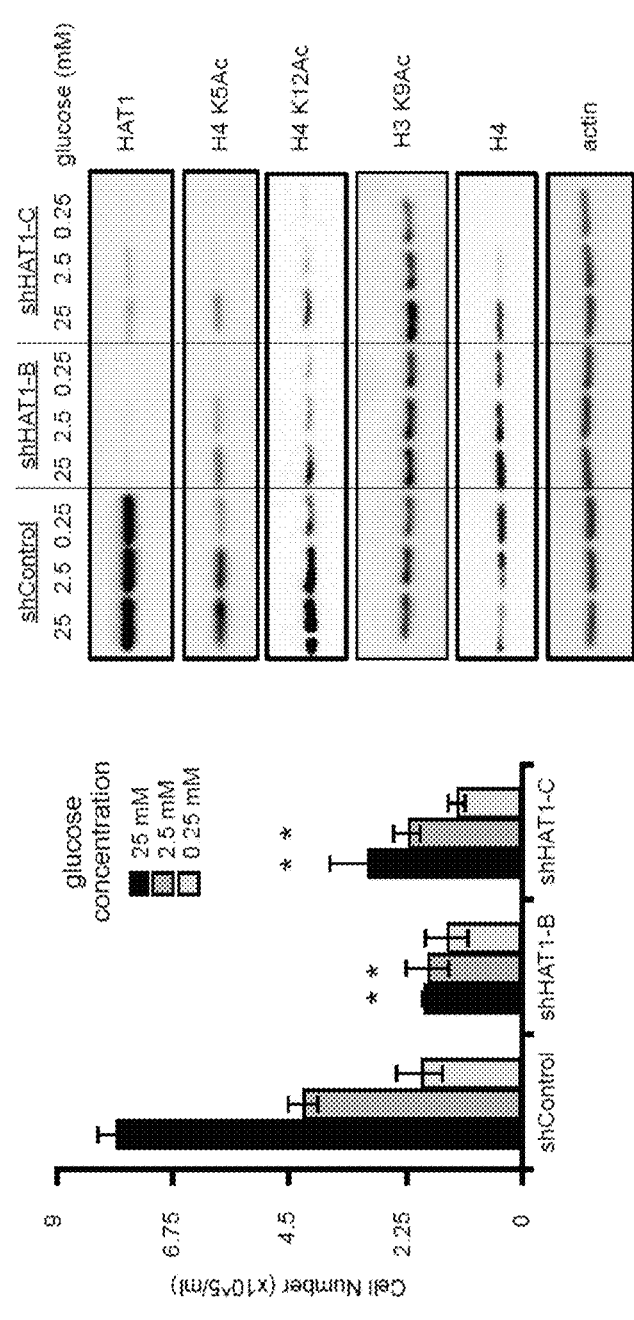
FIG. 43 provides data graphs and immunoblots of hTert-HME1 cells transduced with shRNAs for HAT1 and treated with various concentration of glucose, utilized in various embodiments.

Malignant cells that outgrow their local blood supply can experience nutrient limitation and metabolic stress. Glucose metabolism is a major anabolic pathway of proliferating cancer cells. To assess whether HAT1 contributed to glucose-dependent proliferation, cells were grown in varying levels of glucose-containing media. Cells with stable HAT1 depletion proliferated at a slower rate compared to control cells in both glucose-replete (25 mM) and glucose-limited (2.5 mM) conditions (FIG. 43), whereas more profound glucose limitation equally impaired proliferation regardless of HAT1 levels. In addition, the HAT1-dependent acetylation marks on free H4 (H4K5 and H4K12) were strongly dependent on adequate glucose levels, and further reduced by HAT1 depletion (FIG. 43). In contrast, the nucleosomal acetylation site on H3 lysine 9 was less sensitive to glucose limitation. These data indicate that HAT1 may support glucose-dependent proliferation through acetylation of free histone H4.

In contrast to the acute depletion of HAT1, which causes significant loss of histone H3/H4 dimers (FIG. 24), stable cell lines with HAT1 depletion have normal H4 protein levels (FIG. 43). However, upon glucose limitation, cells with HAT1 depletion did not maintain free H4 levels compared to control cells (FIG. 43). Acetyl-Co-A can be generated from other nutrients including glutamine during periods of glucose withdrawal. Indeed, combined reduction of glucose and glutamine caused diminished nascent H4 levels in wild-type hTert-HME1 cells, an effect that can be partially rescued by pyruvate (FIG. 43), confirming that other sources of nutrients can compensate for glucose deficiency in this cell type.

To determine whether glucose stimulated nascent H4 production at the level of the histone H4 promoter luciferase assays were performed. This Hist1H4E promoter required glucose for full transcriptional activity (FIG. 44). This effect depended on the presence of the H4-box because a Hist1H4E promoter luciferase construct with the H4-box deleted had decreased transcriptional activity and was no longer sensitive to glucose levels (FIG. 44). In addition, ChIP-qPCR showed that H3 lysine 9 promoter acetylation of the Hist1H4C gene was sensitive to glucose levels (FIG. 44). Taken together, these data suggest that H4 promoters are glucose sensitive and that HAT1 is required to maintain nascent histone H4 levels under conditions of glucose limitation, an effect which may depend both on the ability of HAT1 to acetylate nascent H4 and the ability of HAT1 to bind H4 promoters.

Methods

Cell Lines: Female human cell lines MCF10A and hTert-HME1 were obtained from ATCC® and were maintained in mammary epithelial cell growth medium (MEGM® Lonza®) in a humidified incubator at 37° C., with 5% CO2. Glucose-free media was prepared with RPMI-glucose formulation with addition of the MEGM® growth factors. HepG2 and A549 cell lines were obtained from the ENCODE consortium and maintained in MEM and F-12K medias, respectively, supplemented with 10% FBS and 1% penicillin: streptomycin.

Transfection, cell assays: siRNA transfection was performed with 30 microliters of lipid complexes (Lipofectamine® RNAiMAX® Invitrogen®), 3 mL OptiMEM® media, 18 picomoles of siRNA and 5E5-1E6 cells in 10 cm plates. Cell proliferation was measured with a Biorad® TC 10 with trypan blue. Population doublings were calculated using the formula: PD=3.32 (log (counted)−log (plated)), where PD=population doublings, counted=number of cells counted, plated=number of cells plated. For luciferase assays, 500 bp of promoter sequence was cloned into the pGL4.23 vector (Promega®) and constructs were transfected to 293T cells with the X-tremeGENE™ 9 reagent (Roche®). One tenth mass equivalent of pRL-TK plasmid was co-transfected. Luciferase activity was measured with Dual-Luciferase Reporter System (cat #E1910; Promega®) 24 hours after transfection. Double-thymidine block was performed by addition of 2 mM thymidine for 18 hours, followed by 9 hour wash-out with fresh media, then a second block with thymidine (2 mM) for 15 hours, then wash-out and release in the G1/S.

RNAi and cDNAs: HAT1 shRNAs were purchased from OriGene® with the following sequences:

```
                                       (SEQ. ID No. 3)
A)  GATGGCACTACTTTCTAGTATTTGAGAAG;

(SEQ. ID No. 4)
B)  AAGGATGGAGCTACGCTCTTTGCGACCGT;

(SEQ. ID No. 5)
C)  TCCTACAGTTCTTGATATTACAGCGGAAG.
```

The HAT1 cDNA was purchased from OriGene® (catalog #RC209571L1) and the 5' end was extended by a Gibson assembly reaction to add the additional 255 nucleotides to obtain a full-length clone. Mutagenesis of this cDNA was performed with the QuikChange® II Site-Directed Mutagenesis kit with the following primers to make the D276Q acetylation-dead form:

```
                                       (SEQ. ID No. 6)
CAGTTCTTGATATTACAGCGCAAGATCCATCCAAAAGCTAT, (SEQ. ID No. 7)
ATAGCTTTTGGATGGATCTTGCGCTGTAATATCAAGAACTG.
```

To mutate the shRNA-C target site mutagenesis was performed with the following primers:

```
                                       (SEQ. ID No. 8)
GGTCGCAAAGAGCGTAGCTCCGTCTTTGTTGTATTTCTCAAATACTAGA

AAGTAGTGCCATCTTTCATC, (SEQ. ID No. 9)
GATGAAAGATGGCACTACTTTCTAGTATTTGAGAAATACAACAAAGACG

GAGCTACGCTCTTTGCGACC.
```

SILENCER® select (Ambion®) siRNAs were purchased from Life Technologies® (Fisher®). siRNA sequences:

```
                                       (SEQ. ID No. 10)
KAT2B:  GGUACUACGUGUCUAAGAAtt (SEQ. ID No. 11)
KAT2B:  GGUGGUAUCUGUUUCCGUAtt (SEQ. ID No. 12)
KAT2A:  CCAUUUGAGAAACCUAAUAtt (SEQ. ID No. 13)
KAT2A:  AAUGGAACCUGUAAGUGUAtt (SEQ. ID No. 14)
HAT1:  GCAACACGCUAGAAGGGUUtt
```

Mouse tumor studies: The 4T1 mammary carcinoma cell line was infected with lentiviral control or HAT1-targeted shRNAs (mA-GAAGCTACAGACTGGATATTA (SEQ. ID No. 15); mB-GAAGATCTTGCTGTACTATAT (SEQ. ID No. 16)) in the pLKO-puro-IPTG-3xLacO vector (Sigma-Aldrich®) then selected in puromycin and single cell clones were obtained by limiting dilution. To minimize clonal variation, two independent cell line clones from each shRNA were mixed in 1:1 ratio prior to injection of 50,000 cells to bilateral mammary fat pads of 4-6 week-old female Balb/c mice. At day 1 after cell injection 20 mM IPTG was added to the water bottles of all cages to induce shRNA expression and water was changed once a week with repeat addition of IPTG. Tumor size was measured by calipers.

Immunoblots, qRT-PCR: Protein extracts were made in RIPA buffer and quantitated by BCA assay and diluted to equal concentrations. Polyacrylamide gel electrophoresis was performed on NuPAGE® Novex® gradient gels (Thermo Fisher®) followed by wet transfer to nitrocellulose membranes. Blocking was briefly performed with 5% non-fat milk and primary antibody was incubated overnight at 4° C., then with HRP-conjugated secondary antibody (Cell Signaling®) at room temperature for 1 hour followed by washing, then developed with ECL pico or femto (Thermo Fisher®). For gene expression assays total RNA was isolated with AllPrep® (Qiagen®) Dnase treated, then reverse-transcribed with Superscript III (Invitrogen). qPCR was performed with 2× KAPA SYBR FAST Master Mix® on a Quant Studio 6 Flex® (Applied Biosystems®).

ChIP-seq: Log-phase growth cells were crosslinked in 1% formaldehyde at a density of 5×105 cells per milliliter for 10 minutes at room temperature, then quenched with 125 mM glycine for 5 minutes, washed in PBS and snap frozen. Cells were then thawed and nuclei isolated by permeabilization with 2-[4-(2,4,4-trimethylpentan-2-yl)phenoxylethanol (Triton X-100®) followed by washing in a low detergent buffer. Then RIPA was added and sonication was performed by Branson Bransonic® sonicator (3 pulses of 30 seconds each with power output 4 W), followed by 14 cycles of sonication on the Bioruptor® Pico sonicator. Chromatin extracts were then cleared by centrifugation and immunoprecipitation was performed with antibodies and protein A/G agarose beads overnight. The next day the beads were extensively washed with RIPA, then PBS, then resuspended in TE with 1% SDS and crosslinks were reversed overnight at 65 degrees Celsius. The next day RNase A treatment and proteinase K treatment were performed, followed by recovery of DNA with the Qiaquick® spin columns. High throughput sequencing libraries were then constructed by A tailing, adapter ligation and 10-15 cycles of PCR followed by library purification, removal of PCR primer-dimers and high-throughput sequencing by HiSeq 4000®. Antibodies for ChIP-seq: Rbap46 (V415) from Cell Signaling® (cat #6882); HAT1 from Abcam® (cat #ab194296); Histone H4 acetyl K12 from Abcam® (cat #ab46983); acetyl-Histone H4 (Lys5) from Millipore® (ca #07-327).

Chromatin accessibility: A modified form of the published ATAC-seq protocol (J. D. Buenrostro, et al., (2013) Nature methods 10, 1213-1218, the disclosure of which is incorporated herein by reference) was used to assess chromatin accessibility on the luciferase reporter with specific primers (CAACACACCAACGAAAATAGCC (SEQ. ID No. 17), CGCTCGTTGTAGATGTCGTTAG (SEQ. ID No. 18)). Cells were counted and 50,000 cells were used for nuclei isolation then transposition reaction with the Tn5 transposase (Illumina®). Isolated DNA was then size purified by agarose electrophoresis to recover DNA of size 75-500 bp. Then qPCR was performed with the indicated primers.

ChIP-seq and ATAC-seq peak calling and analysis: Paired-end 100 bp reads were trimmed with cutadapt version 1.8.1 with flags -u -50 -U -50 -a CTGTCTCTTATACA-CATCTCCGAGCCCACGAGAC (SEQ. ID No. 19) -A CTGTCTCTTATACACATCTGACGCTGCCGACGA (SEQ. ID No. 20)-O 5 -m 30 -q 15. Bowtie (B. Langmead, et al., (2009) Genome biology 10, R25, the disclosure of which is incorporated herein by reference) version 1.1.1 was used to align trimmed reads to hg19 with flags -q --phred33-quals -X 2000 -m 1 --fr -p 8 -S --chunkmbs 400, followed by samtools sort command. Duplicates were marked with Picard-tools version 1.92, then samtools view with flags-b-f 1 -F12 -L were used to filter mitochondrial mapping reads with a bed file containing all chromosomes except chrM. SPP/phantom P. V. Kharchenko, M. Y. Tostorukov, and P. J. Park, (2008) Nature biotechnology 26, 1351-1359; and S. G. Landt, et al., (2012) Genome research 22, 1813-1831; the disclosures of which are each incorporated herein by reference) was run to obtain the fragment length with maximum strand cross-correlation. MACS2 (Y. Zhang, et al., (2008) Genome biology 9, R137, the disclosure of which is incorporated herein by reference) callpeak function was then performed with flags -q 0.05 -nomodel -extsize=1/2 fragment length obtained from SPP. The program align2rawsignal (ENCODE Project Consortium (2012) Nature 489, 57-74, the disclosure of which is incorporated herein by reference) (Kundaje) was used to create genome-wide signal coverage tracks with normalization to account for depth of sequencing and read mappability with flags kernel (k)=epanechnikov, fragment length (1)=150 (ATAC-seq) or (1)=1/2 fragment length from SPP for ChIP-seq, smoothing window (w)=150, normFlag(n)=5, mapFilter (f)=0. Further peak calling was performed with DiffBind (C. S. Ross, et al., (2012) Nature 481, 389-393; and R. Stark (2011) (http://bioconductor.org/packages/release/bioc/vignettes/DiffBind/inst/doc/DiffBind.pdf); the disclosures of which are each incorporated herein by reference) with summits=250 paramter contrasting ChIP-antibody to input control to obtain final enriched peak counts.

TCGA gene expression analysis: Exploratory analysis and generation of survival plots and statistics was performed with the GEPIA resource (Z. Tang, et al., (2017) Nucleic acids research 45, W98-W102, the disclosure of which is incorporated herein by reference).

DOCTRINE OF EQUIVALENTS

While the above description contains many specific embodiments of the invention, these should not be construed as limitations on the scope of the invention, but rather as an example of one embodiment thereof. Accordingly, the scope of the invention should be determined not by the embodiments illustrated, but by the appended claims and their equivalents.

What is claimed is:

1. A method to identify modulators of histone acetyltransferase 1 activity, comprising:

providing a substrate in a solution within a well, wherein the substrate is a peptide comprising a natural substrate of histone acetyltransferase 1, wherein the substrate is fixed to a surface of the well;

adding to the solution a histone acetyltransferase 1, a donor molecule, and a modulator, wherein the donor molecule comprises a coenzyme A structure with an acetyl-like group, wherein the acetyl-like group comprises a carbonyl group and an alkyl extending from the carbonyl group, wherein the alkyl comprises a terminal alkyne, wherein the histone acetyltransferase 1 is extracellular and is capable of transferring the acetyl-like group of the donor molecule onto the substrate, wherein the modulator is a compound being assessed for its ability to modulate the transfer of the acetyl-like group onto the substrate;

removing the histone acetyltransferase 1, the donor molecule, and the modulator from the solution, wherein the substrate remains fixed to the surface of the well;

adding to the solution biotin-azide, wherein the azide group is configured to conjugate to the alkyne of the acetyl-like group to yield a biotin extending from the substrate via a transferred acetyl-like group;

removing unconjugated biotin-azide from the solution, wherein the substrate remains fixed to the surface of the well;

adding to the solution a reporter molecule conjugated with streptavidin, wherein the reporter molecule is configured to bind to the biotin extending from the substrate;

removing unbound reporter molecule from the solution, wherein the substrate remains fixed to the surface of the well; and measuring signal of the reporter molecule bound to the substrate.

2. The method of claim 1, wherein the histone acetyltransferase 1 is a recombinant histone acetyltransferase 1.

3. The method of claim 1, wherein the substrate is an n-terminal peptide of histone H4.

4. The method of claim 3, wherein the n-terminal peptide of histone H4 has a sequence consisting of SEQ ID No. 1.

5. The method of claim 3, wherein the n-terminal peptide of histone H4 is provided at 15 μM.

6. The method of claim 1, wherein the donor molecule is 4-pentynoyl Co-A.

7. The method of claim 1, wherein the reporter molecule is selected from the group consisting of a fluorophore, a radioisotope, an enzyme, and an antigen binding molecule.

8. The method of claim 1, wherein the reporter molecule is horse radish peroxidase (HRP) and a HRP substrate is utilized to visualize HRP activity.

9. The method of claim 8, wherein the HRP substrate is 10-Acetyl-3,7-dihydroxyphenoxazine.

10. The method of claim 1, wherein the histone acetyltransferase 1 is a recombinant histone acetyltransferase 1, the substrate is an n-terminal peptide of histone H4, the donor molecule is 4-pentynoyl Co-A, the reporter molecule is horse radish peroxidase (HRP) and 10-Acetyl-3,7-dihydroxyphenoxazine is used as a HRP substrate to visualize HRP activity.

11. The method of claim 2, further comprising producing the recombinant histone acetyltransferase 1 in a human cell line.

12. The method of claim 11, wherein the human cell line is HEK-293f.

13. The method of claim 11, wherein producing the recombinant histone acetyltransferase 1 further comprises co-expressing the recombinant histone acetyltransferase 1 with a recombinant RBAP46 within the human cell line.

14. The method of claim 11, wherein producing the recombinant histone acetyltransferase 1 further comprises adding one or more factors to the human cell line, wherein the one or more factors are selected from the group consisting of acetate, forskolin, orthovanadate, and AICAR.

15. The method of claim 1, further comprising adding one or more reagents to the solution to promote the transfer of the acetyl-like group onto the substrate, wherein the one or more reagents are selected from the group consisting of EDTA and DTT.

16. The method of claim 1, wherein the modulator is an agonist of histone acetyltransferase 1, wherein the agonist is selected from the group consisting of 2-(Hydroxymethyl)-6-[1,3,4-trihydroxy-1-(2-phenyltriazol-4-yl)butan-2-yl]oxyoxane-3,4,5-triol and 1-(1H-Benzimidazol-2-yl)hexane-1,2,3,4,5,6-hexol;2,3-dihydroxybutanedioic acid.

17. The method of claim 1, wherein the modulator is an antagonist of histone acetyltransferase 1, wherein the antagonist is selected from the group consisting of nogalarol, 3-[3,4-Dihydroxy-5-(hydroxymethyl)oxolan-2-yl]-6,7-dihydroxy-6-methyl-5,7-dihydroimidazo[1,2-a]purin-9-one, daunomycin 3-oxime hydrochloride, rhodomycin A, aclacinomycin A1, cinerubin B, Methyl (1R,2R,4S)-4-[5-[5-(4,5-dihydroxy-6-methyloxan-2-yl)oxy-4-hydroxy-6-methyl-oxan-2-yl]oxy-4-(dimethylamino)-6-methyloxan-2-yl]oxy-2-ethyl-2,5,7,10-tetrahydroxy-6,11-dioxo-3,4-dihydro-1H-tetracene-1-carboxylate, nagalomycin C, N,N-Dibenzyldaunorubicin, and pyrromycin.

* * * * *